US011708328B2

(12) United States Patent
Lee et al.

(10) Patent No.: US 11,708,328 B2
(45) **Date of Patent: *Jul. 25, 2023**

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Su-Hyun Lee, Gyeonggi-do (KR); Hyo-Soon Park, Gyeonggi-do (KR); Tae-Jun Han, Gyeonggi-do (KR); Bitnari Kim, Gyeonggi-do (KR)

(73) Assignee: Rohm and Haas Electronic Materials Korea Ltd.

(*) Notice: Subject to any disclaimer, the term of this patent is extended or adjusted under 35 U.S.C. 154(b) by 414 days.

This patent is subject to a terminal disclaimer.

(21) Appl. No.: 16/641,286

(22) PCT Filed: Aug. 23, 2018

(86) PCT No.: PCT/KR2018/009694

§ 371 (c)(1),
(2) Date: Feb. 24, 2020

(87) PCT Pub. No.: WO2019/066260

PCT Pub. Date: Apr. 4, 2019

(65) Prior Publication Data

US 2020/0207713 A1 Jul. 2, 2020

(30) Foreign Application Priority Data

Sep. 26, 2017 (KR) ........................ 10-2017-0124011

(51) Int. Cl.

| | |
|---|---|
| ***C07D 209/80*** | (2006.01) |
| ***C07D 307/93*** | (2006.01) |
| ***C07D 333/80*** | (2006.01) |
| ***C07D 401/04*** | (2006.01) |
| ***C07D 401/14*** | (2006.01) |
| ***C07D 403/04*** | (2006.01) |
| ***C07D 403/10*** | (2006.01) |
| ***C07D 405/04*** | (2006.01) |
| ***C07D 405/10*** | (2006.01) |
| ***C07D 409/04*** | (2006.01) |
| ***C07D 409/10*** | (2006.01) |
| ***C07D 471/04*** | (2006.01) |
| ***C07D 487/04*** | (2006.01) |
| ***C07D 491/048*** | (2006.01) |
| ***C07D 495/04*** | (2006.01) |
| ***H01L 51/00*** | (2006.01) |

(52) U.S. Cl.

CPC ......... *C07D 209/80* (2013.01); *C07D 307/93* (2013.01); *C07D 333/80* (2013.01); *C07D 401/04* (2013.01); *C07D 401/14* (2013.01); *C07D 403/04* (2013.01); *C07D 403/10* (2013.01); *C07D 405/04* (2013.01); *C07D 405/10* (2013.01); *C07D 409/04* (2013.01); *C07D 409/10* (2013.01); *C07D 471/04* (2013.01); *C07D 487/04* (2013.01); *C07D 491/048* (2013.01); *C07D 495/04* (2013.01); *H01L 51/006* (2013.01); *H01L 51/0052* (2013.01); *H01L 51/0065* (2013.01); *H01L 51/0067* (2013.01); *H01L 51/0068* (2013.01)

(58) Field of Classification Search

CPC .......................... C07D 209/80; H01L 51/0052

See application file for complete search history.

(56) References Cited

U.S. PATENT DOCUMENTS

| | | | | |
|---|---|---|---|---|
| 9,997,723 | B2 | 6/2018 | Kang et al. | |
| 11,008,280 | B2 * | 5/2021 | Mun | C07D 405/04 |
| 11,283,028 | B2 * | 3/2022 | Lee | H01L 51/0052 |
| 2015/0307514 | A1 | 10/2015 | Park et al. | |
| 2018/0123051 | A1 | 5/2018 | Lee et al. | |
| 2019/0019962 | A1 | 1/2019 | Mun et al. | |
| 2019/0097138 | A1 | 3/2019 | Lee et al. | |
| 2019/0300535 | A1 | 10/2019 | Mun et al. | |
| 2020/0212310 | A1 | 7/2020 | Kim et al. | |

FOREIGN PATENT DOCUMENTS

| | | | |
|---|---|---|---|
| KR | 20130083817 | A | 7/2013 |
| KR | 20140111719 | A | 9/2014 |
| KR | 20140136722 | A | 12/2014 |
| KR | 101627750 | B | 6/2016 |
| KR | 20180020522 | A | 2/2018 |

OTHER PUBLICATIONS

Lee et al (2017): STN International (Columbus, Ohio), CAPLUS database, Accession No. 2017: 1526973.*

Park et al (2017): STN International (Columbus, Ohio), CAPLUS database, Accession No. 2015: 1733845.*

Search Report from KIPO for Korean application No. 2017-0124011; dated Sep. 26, 2017.

* cited by examiner

*Primary Examiner* — Golam M Shameem

(74) *Attorney, Agent, or Firm* — G. Creston Campbell

(57) ABSTRACT

The present disclosure relates to an organic electroluminescent compound and an organic electroluminescent device comprising the same. By comprising the organic electroluminescent compound of the present disclosure, it is possible to provide an organic electroluminescent device having low driving voltage and/or improved lifespan properties.

6 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

In 1987, Tang et al. of Eastman Kodak first developed a small molecule green organic electroluminescent device (OLED) of TPD/A1q3 bilayer consisting of a light-emitting layer and a charge transport layer. Since then, the research on an OLED has been rapidly carried out, and it has been commercialized. An OLED changes electric energy into light by applying electricity to an organic light-emitting material, and commonly comprises an anode, a cathode, and an organic layer formed between the two electrodes. The organic layer of the OLED may comprise a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc., if necessary. The materials used in the organic layer can be classified into a hole injection material, a hole transport material, a hole auxiliary material, a light-emitting auxiliary material, an electron blocking material, a light-emitting material, an electron buffer material, a hole blocking material, an electron transport material, an electron injection material, etc., depending on functions.

The most important factor determining luminous efficiency in an OLED is light-emitting materials. The light-emitting materials are required to have the high quantum efficiency, high movement degree of an electron and a hole, and uniformality and stability of the formed light-emitting material layer. The light-emitting material is classified into blue, green, and red light-emitting materials according to the light-emitting color, and further includes yellow or orange light-emitting materials. Furthermore, the light-emitting material is classified into a host material and a dopant material in a functional aspect. Recently, an urgent task is the development of an OLED having high efficiency and long lifespan. In particular, the development of highly excellent light-emitting material over conventional materials is urgently required, considering the EL properties necessary for medium- and large-sized OLED panels. For this, preferably, as a solvent in a solid state and an energy transmitter, a host material should have high purity and a suitable molecular weight in order to be deposited under vacuum. Furthermore, a host material is required to have high glass transition temperature and pyrolysis temperature to achieve thermal stability, high electrochemical stability to achieve a long lifespan, easy formability of an amorphous thin film, good adhesion with adjacent layers, and no movement between layers.

Korean Patent No. 1627750 discloses a benzo[a]indolo[3,2-c]carbazole structure, and Korean Patent Application Laid-Open No. 2015-135109 discloses a dibenzocarbazole linked with a heteroaryl moiety such as quinazoline or quinoxaline via a single bond or linker. However, the above documents do not specifically disclose the structure in which residues of the backbone are further fused. The development for improving the performance of an OLED is still required.

DISCLOSURE OF INVENTION

Technical Problem

The objective of the present disclosure is to provide an organic electroluminescent compound effective for producing an organic electroluminescent device having low driving voltage and/or improved lifespan properties.

Solution to Problem

The present inventors found that that the above objective can be achieved by an organic electroluminescent compound represented by the following formula 1:

(1)

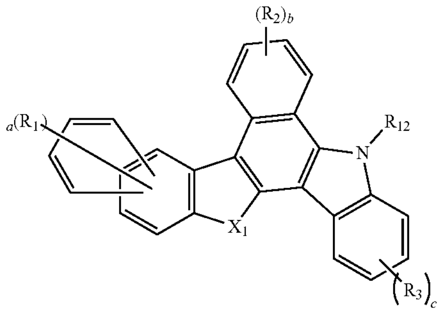

wherein $X_1$ represents $NR_{11}$, O, S, or $CR_{21}R_{22}$;

$R_{11}$ and $R_{12}$, each independently, are represented by -L-Ar;

Ar, and $R_1$ to $R_3$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a substituted or unsubstituted (3- to 30-membered) mono- or polycyclic ring;

L represents a single bond, a substituted or unsubstituted (C1-C30)alkylene, a substituted or unsubstituted (C6-C30) arylene, a substituted or unsubstituted (3- to 30-membered) heteroarylene, or a substituted or unsubstituted (C3-C30) cycloalkylene; with a proviso that if Ar represents hydrogen, L represents a single bond;

$R_{21}$ and $R_{22}$, each independently, represent a substituted or unsubstituted (C1-C30)alkyl, or a substituted or unsubstituted (C6-C30)aryl; or may be linked to an adjacent substituent to form a spirofluorene form; and a represents an integer of 1 to 6, b and c, each independently, represent an integer of 1 to 4, where if a to c, each independently, are an integer of 2 or more, each of $R_1$ to $R_3$ may be the same or different.

Advantageous Effects of Invention

The organic electroluminescent compound according to the present disclosure can provide an organic electroluminescent device having low driving voltage and/or improved lifespan properties.

MODE FOR THE INVENTION

Hereinafter, the present disclosure will be described in detail. However, the following description is intended to explain the invention, and is not meant in any way to restrict the scope of the invention.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material layer (containing host and dopant materials), an electron buffer material, a hole blocking material, an electron transport material, an electron injection material, etc.

Hereinafter, the compound represented by formula 1 will be described in more detail.

In formula 1, $X_1$ represents $NR_{11}$, O, S, or $CR_{21}R_{22}$; and $R_{11}$ and $R_{12}$, each independently, are represented by -L-Ar;

L represents a single bond, a substituted or unsubstituted (C1-C30)alkyl(ene), a substituted or unsubstituted (C6-C30) aryl(ene), a substituted or unsubstituted (3- to 30-membered)heteroaryl(ene), or a substituted or unsubstituted (C3-C30)cycloalkyl(ene); with a proviso that if Ar represents hydrogen, L represents a single bond. As one embodiment, L represents a single bond, a substituted or unsubstituted (C6-C25)aryl(ene), or a substituted or unsubstituted (5- to 25-membered)heteroaryl(ene). As another embodiment, L represents a single bond, an unsubstituted (C6-C18)arylene, or an unsubstituted (5- to 18-membered)heteroarylene. For example, L may represent a single bond, an unsubstituted phenylene, an unsubstituted pyridylene, an unsubstituted pyrimidinylene, an unsubstituted quinazolinylene, an unsubstituted quinoxalinylene, an unsubstituted carbazolylene, an unsubstituted benzofuropyrimidinylene, or an unsubstituted benzothiopyrimidinylene.

In formula 1, $R_1$ to $R_3$, and Ar, each independently, represent hydrogen, deuterium, a halogen, a cyano, a substituted or unsubstituted (C1-C30)alkyl, a substituted or unsubstituted (C2-C30)alkenyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30) alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30) arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a substituted or unsubstituted (3- to 30-membered) mono- or polycyclic ring.

As one embodiment, Ar represents hydrogen, a (C6-C25) aryl unsubstituted or substituted with a (C1-C30)alkyl or a cyano, a (5- to 25-membered)heteroaryl unsubstituted or substituted with a (C6-C25)aryl, or an unsubstituted di(C6-C18)arylamino. As another embodiment, Ar represents a (C6-C18)aryl unsubstituted or substituted with a (C1-$C_6$) alkyl or a cyano, a (5- to 20-membered)heteroaryl unsubstituted or substituted with a (C6-C18)aryl, or an unsubstituted di(C6-C18)arylamino. For example, Ar may represent a phenyl unsubstituted or substituted with a cyano; naphthylphenyl; naphthyl; biphenyl; dimethylfluorenyl; phenanthrenyl; dimethylbenzofluorenyl; triphenylenyl; terphenyl; diphenyltriazinyl; phenylbiphenyltriazinyl; dibenzofuranyl; dibenzothiophenyl; phenylcarbazolyl; diphenylquinazolinyl; diphenylquinoxalinyl; or diphenylamino.

As one embodiment, $R_1$ to $R_3$, each independently, represent hydrogen, or a substituted or unsubstituted (C6-C25) aryl; or may be linked to an adjacent substituent to form a substituted or unsubstituted (3- to 30-membered) mono- or polycyclic ring. As another embodiment, $R_1$ to $R_3$, each independently, represent hydrogen, or an unsubstituted (C6-C18)aryl. For example, $R_1$ to $R_3$, each independently, may represent hydrogen or phenyl.

In formula 1, $R_{21}$ and $R_{22}$, each independently, represent a substituted or unsubstituted (C1-C30)alkyl, or a substituted or unsubstituted (C6-C30)aryl; or may be linked to an adjacent substituent to form a spirofluorene form. As one embodiment, $R_{21}$ and $R_{22}$, each independently, represent a substituted or unsubstituted (C1-C10)alkyl; or may be linked to an adjacent substituent to form a spirofluorene form. As another embodiment, $R_{21}$ and $R_{22}$, each independently, represent an unsubstituted (C1-C6)alkyl. For example, $R_{21}$ and $R_{22}$, each independently, may represent a methyl.

In formula 1, a represents an integer of 1 to 6, b and c, each independently, represent an integer of 1 to 4, where if a to c, each independently, are an integer of 2 or more, each of $R_1$ to $R_3$ may be the same or different. As one embodiment, a to c, each independently, represent 1 or 2. As another embodiment, a to c, each independently, represent 1.

The compound represented by formula 1 may be represented by any one of the following formulas 2 and 3.

(2)

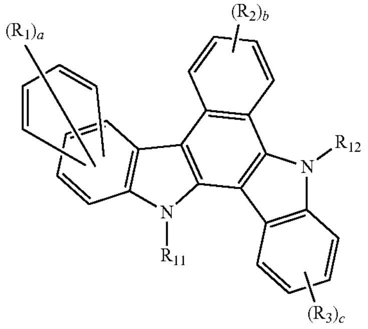

-continued (3)

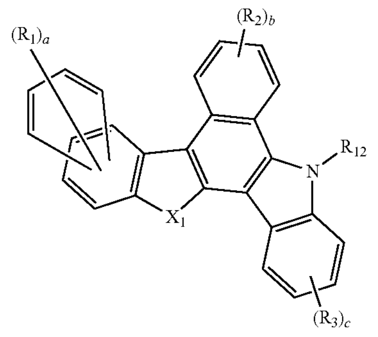

In formulas 2 and 3, $X_1$, $R_{11}$, $R_{12}$, $R_1$ to $R_3$, and a to c are as defined in formula 1.

According to one embodiment of the present disclosure, in formulas 2 and 3, $X_1$ represents O, S or $CR_{21}R_{22}$, and $R_{21}$ and $R_{22}$, each independently, represent an unsubstituted (C1-C10)alkyl; $R_{11}$ and $R_{12}$, each independently, are represented by -L-Ar; L represents a single bond, an unsubstituted (C6-C25)arylene, or an unsubstituted (5- to 25-membered) heteroarylene; Ar represents a (C6-C25)aryl unsubstituted or substituted with a (C1-C30)alkyl or a cyano, a (5- to 25-membered)heteroaryl unsubstituted or substituted with a (C6-C25)aryl, or an unsubstituted di(C6-C25)arylamino; $R_1$ to $R_3$, each independently, represent an unsubstituted (C6-C25)aryl; and a, b, and c, each independently, represent 0 or 1.

The compound represented by formula 1 may be represented by any one of the following formulas 4 to 6.

(4)

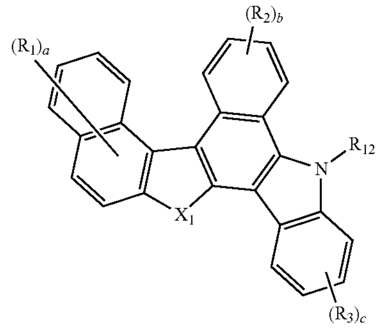

(5)

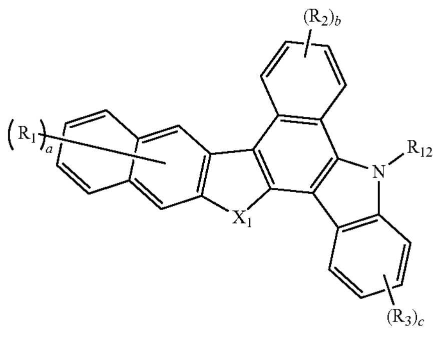

-continued (6)

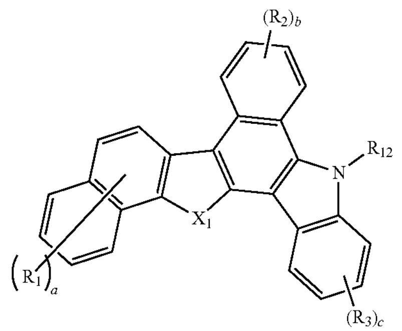

In formulas 4 to 6, $X_1$, $R_{12}$, $R_1$ to $R_3$, and a to c are as defined in formula 1.

According to one embodiment of the present disclosure, in formulas 4 to 6, $X_1$ represents $NR_{11}$, O, S, or $CR_{21}R_{22}$, and $R_{21}$ and $R_{22}$, each independently, represent an unsubstituted (C1-$C_6$)alkyl; $R_{11}$ and $R_{12}$, each independently, are represented by -L-Ar; L represents a single bond, an unsubstituted (C6-C18)arylene, or an unsubstituted (5- to 20-membered)heteroarylene; Ar represents a (C6-C18)aryl unsubstituted or substituted with a (C1-C6)alkyl or a cyano, a (5- to 20-membered)heteroaryl unsubstituted or substituted with a (C6-C18)aryl, or an unsubstituted di(C6-C18) arylamino; $R_1$ to $R_3$, each independently, represent an unsubstituted (C6-C18)aryl; and a, b, and c, each independently, represent 0 or 1.

The compound represented by formula 1 may be represented by any one of the following formulas 7 to 15.

(7)

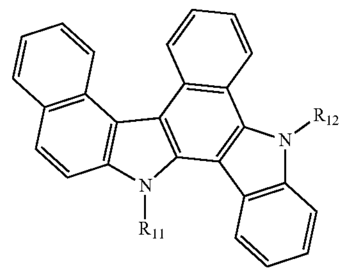

(8)

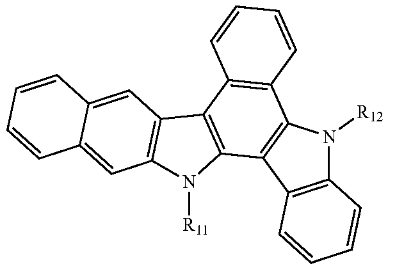

(9)

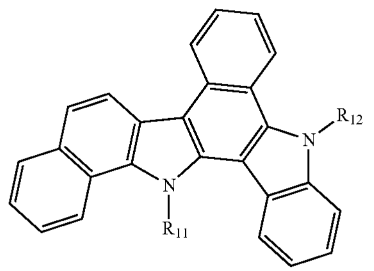

-continued
(10)
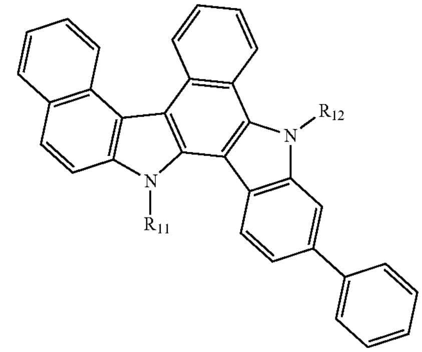
(11)
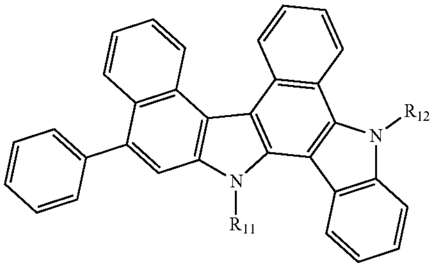
(12)
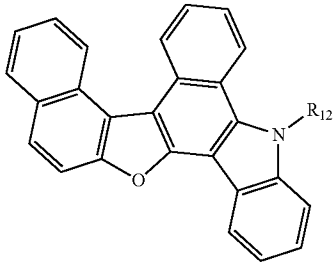
(13)
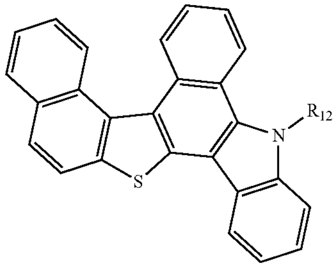
(14)
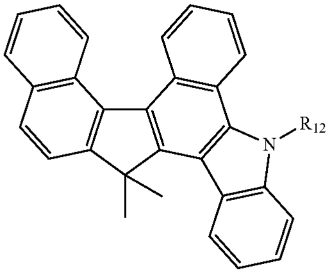
-continued
(15)
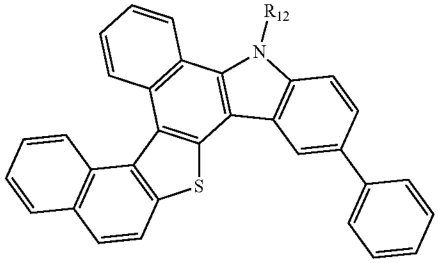
In formulas 7 to 15, $R_{11}$ and $R_{12}$ are as defined in formula 1. According to one embodiment of the present disclosure, in formulas 7 to 15, $R_{11}$ and $R_{12}$, each independently, are any one selected from the group consisting of the following $R_{aa}$, to $R_{bi}$.
$R_{aa}$
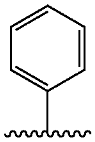
$R_{ab}$
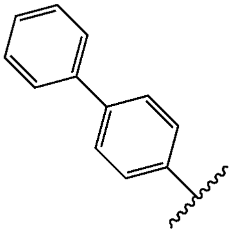
$R_{ac}$
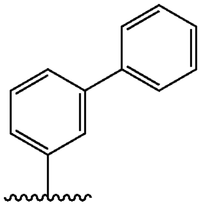
$R_{ad}$
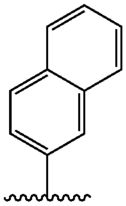
$R_{ae}$
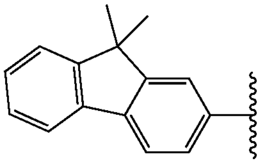

-continued
$R_{af}$
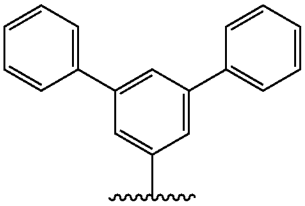
$R_{ag}$
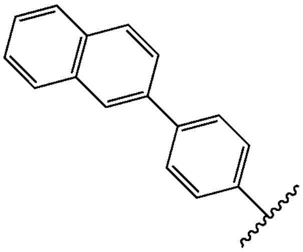
$R_{ah}$
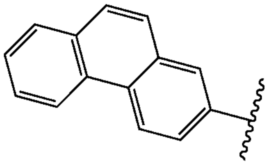
$R_{ai}$
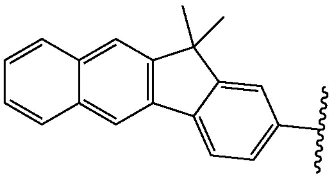
$R_{aj}$
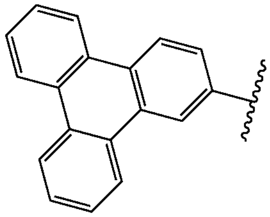
$R_{ak}$
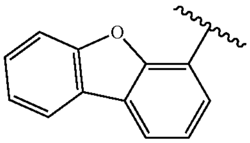
$R_{al}$
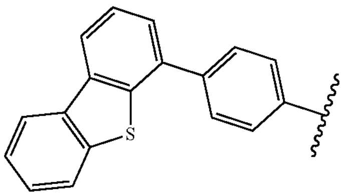
-continued
$R_{am}$
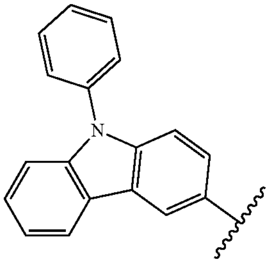
$R_{an}$
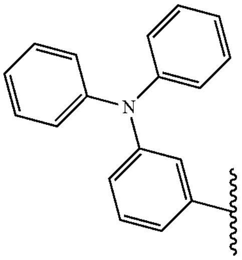
$R_{ao}$
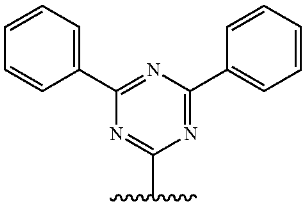
$R_{ap}$
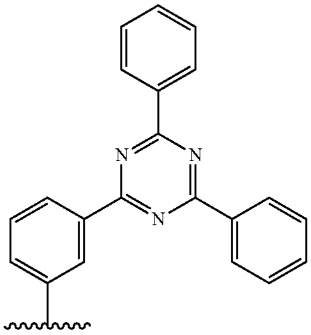
$R_{aq}$
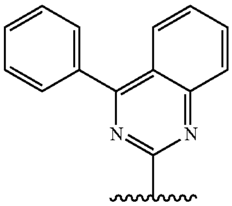

-continued
$R_{ar}$
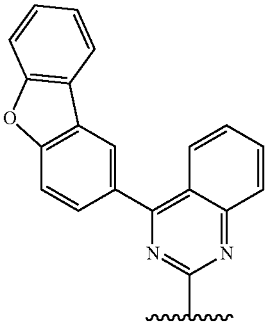
$R_{as}$
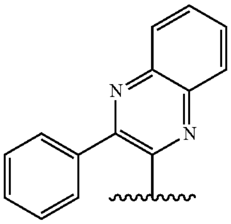
$R_{at}$
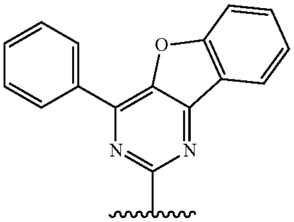
$R_{au}$
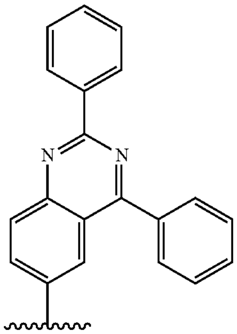
$R_{av}$
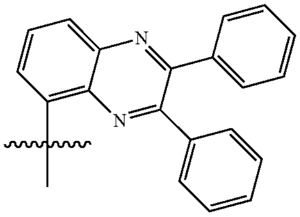
-continued
$R_{aw}$
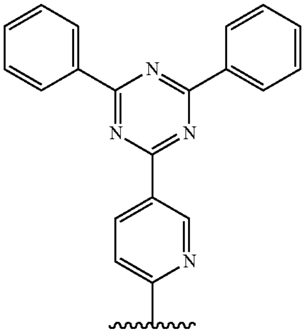
$R_{ax}$
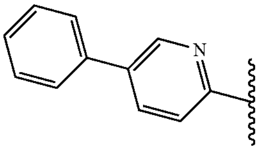
$R_{ay}$
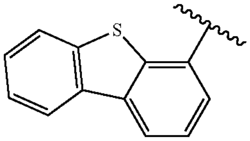
$R_{az}$
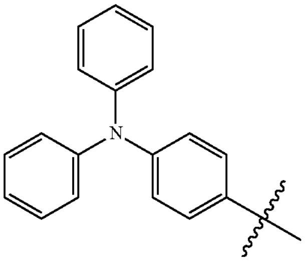
$R_{ba}$
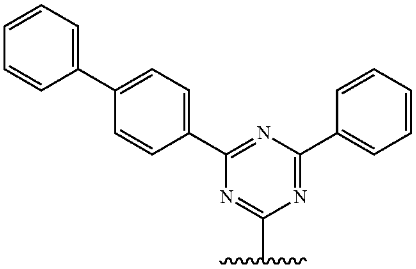
$R_{bb}$
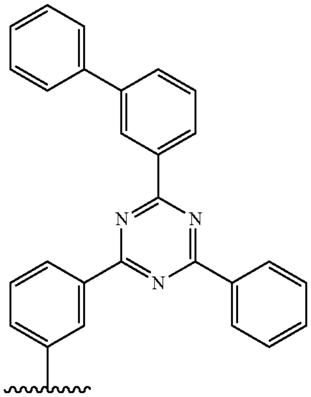

-continued $R_{bc}$

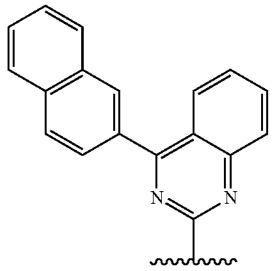

$R_{bd}$

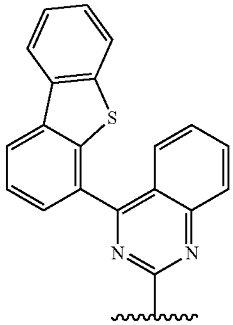

$R_{be}$

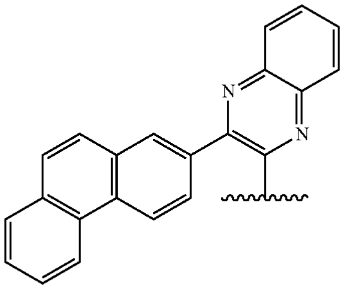

$R_{bf}$

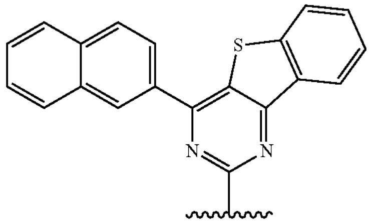

$R_{bg}$

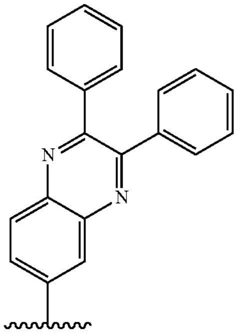

-continued $R_{bh}$

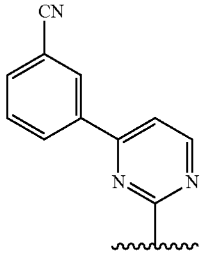

$R_{bi}$

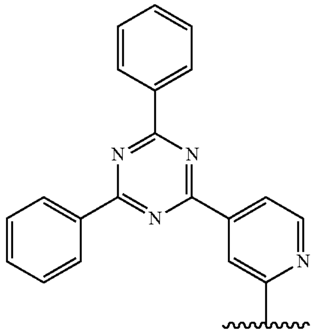

The compound represented by formula 1 may be exemplified by any one selected from the following compounds C1-1 to C7-48, but is not limited thereto. Each of the following compounds C1-1 to C7-48 is represented by any one of the above-mentioned formulas 7 to 15, wherein $R_{11}$ and $R_{12}$, each independently, are defined as any one of $R_{aa}$ to $R_{bi}$.

| Compound | Formula | $R_{11}$ | $R_{12}$ | Compound | Formula | $R_{11}$ | $R_{12}$ |
|---|---|---|---|---|---|---|---|
| C1-1 | 7 | $R_{aa}$ | $R_{aa}$ | C1-2 | 7 | $R_{ab}$ | $R_{aa}$ |
| C1-3 | 7 | $R_{ac}$ | $R_{aa}$ | C1-4 | 7 | $R_{ad}$ | $R_{aa}$ |
| C1-5 | 7 | $R_{ae}$ | $R_{aa}$ | C1-6 | 7 | $R_{aa}$ | $R_{ab}$ |
| C1-7 | 7 | $R_{ab}$ | $R_{ab}$ | C1-8 | 7 | $R_{ac}$ | $R_{ab}$ |
| C1-9 | 7 | $R_{ad}$ | $R_{ab}$ | C1-10 | 7 | $R_{ae}$ | $R_{ab}$ |
| C1-11 | 7 | $R_{aa}$ | $R_{ac}$ | C1-12 | 7 | $R_{ab}$ | $R_{ac}$ |
| C1-13 | 7 | $R_{ac}$ | $R_{ac}$ | C1-14 | 7 | $R_{ad}$ | $R_{ac}$ |
| C1-15 | 7 | $R_{ae}$ | $R_{ac}$ | C1-16 | 7 | $R_{aa}$ | $R_{af}$ |
| C1-17 | 7 | $R_{ab}$ | $R_{af}$ | C1-18 | 7 | $R_{ac}$ | $R_{af}$ |
| C1-19 | 7 | $R_{ad}$ | $R_{af}$ | C1-20 | 7 | $R_{ae}$ | $R_{af}$ |
| C1-21 | 7 | $R_{aa}$ | $R_{ag}$ | C1-22 | 7 | $R_{ab}$ | $R_{ag}$ |
| C1-23 | 7 | $R_{ac}$ | $R_{ag}$ | C1-24 | 7 | $R_{ad}$ | $R_{ag}$ |
| C1-25 | 7 | $R_{ae}$ | $R_{ag}$ | C1-26 | 7 | $R_{aa}$ | $R_{ah}$ |
| C1-27 | 7 | $R_{ab}$ | $R_{ah}$ | C1-28 | 7 | $R_{ac}$ | $R_{ah}$ |
| C1-29 | 7 | $R_{ad}$ | $R_{ah}$ | C1-30 | 7 | $R_{ae}$ | $R_{ah}$ |
| C1-31 | 7 | $R_{aa}$ | $R_{ai}$ | C1-32 | 7 | $R_{ab}$ | $R_{ai}$ |
| C1-33 | 7 | $R_{ac}$ | $R_{ai}$ | C1-34 | 7 | $R_{ad}$ | $R_{ai}$ |
| C1-35 | 7 | $R_{ae}$ | $R_{ai}$ | C1-36 | 7 | $R_{aa}$ | $R_{aj}$ |
| C1-37 | 7 | $R_{ab}$ | $R_{aj}$ | C1-38 | 7 | $R_{ac}$ | $R_{aj}$ |
| C1-39 | 7 | $R_{ad}$ | $R_{aj}$ | C1-40 | 7 | $R_{ae}$ | $R_{aj}$ |
| C1-41 | 7 | $R_{aa}$ | $R_{ak}$ | C1-42 | 7 | $R_{ab}$ | $R_{ak}$ |
| C1-43 | 7 | $R_{ac}$ | $R_{ak}$ | C1-44 | 7 | $R_{ad}$ | $R_{ak}$ |
| C1-45 | 7 | $R_{ae}$ | $R_{ak}$ | C1-46 | 7 | $R_{aa}$ | $R_{al}$ |
| C1-47 | 7 | $R_{ab}$ | $R_{al}$ | C1-48 | 7 | $R_{ac}$ | $R_{al}$ |
| C1-49 | 7 | $R_{ad}$ | $R_{al}$ | C1-50 | 7 | $R_{ae}$ | $R_{al}$ |
| C1-51 | 7 | $R_{aa}$ | $R_{am}$ | C1-52 | 7 | $R_{ab}$ | $R_{am}$ |
| C1-53 | 7 | $R_{ac}$ | $R_{am}$ | C1-54 | 7 | $R_{ad}$ | $R_{am}$ |
| C1-55 | 7 | $R_{ae}$ | $R_{am}$ | C1-56 | 7 | $R_{aa}$ | $R_{an}$ |
| C1-57 | 7 | $R_{ab}$ | $R_{an}$ | C1-58 | 7 | $R_{ac}$ | $R_{an}$ |
| C1-59 | 7 | $R_{ad}$ | $R_{an}$ | C1-60 | 7 | $R_{ae}$ | $R_{an}$ |
| C1-61 | 7 | $R_{aa}$ | $R_{ao}$ | C1-62 | 7 | $R_{ab}$ | $R_{ao}$ |
| C1-63 | 7 | $R_{ak}$ | $R_{ao}$ | C1-64 | 7 | $R_{an}$ | $R_{ao}$ |
| C1-65 | 7 | $R_{aa}$ | $R_{ap}$ | C1-66 | 7 | $R_{ab}$ | $R_{ap}$ |
| C1-67 | 7 | $R_{ak}$ | $R_{ap}$ | C1-68 | 7 | $R_{an}$ | $R_{ap}$ |
| C1-69 | 7 | $R_{aa}$ | $R_{aq}$ | C1-70 | 7 | $R_{ab}$ | $R_{aq}$ |

-continued

| Compound | Formula | $R_{11}$ | $R_{12}$ | Compound | Formula | $R_{11}$ | $R_{12}$ |
|---|---|---|---|---|---|---|---|
| C1-71 | 7 | $R_{ak}$ | $R_{aq}$ | C1-72 | 7 | $R_{an}$ | $R_{aq}$ |
| C1-73 | 7 | $R_{aa}$ | $R_{ar}$ | C1-74 | 7 | $R_{ab}$ | $R_{ar}$ |
| C1-75 | 7 | $R_{ak}$ | $R_{ar}$ | C1-76 | 7 | $R_{an}$ | $R_{ar}$ |
| C1-77 | 7 | $R_{aa}$ | $R_{as}$ | C1-78 | 7 | $R_{ab}$ | $R_{as}$ |
| C1-79 | 7 | $R_{ak}$ | $R_{as}$ | C1-80 | 7 | $R_{an}$ | $R_{as}$ |
| C1-81 | 7 | $R_{aa}$ | $R_{at}$ | C1-82 | 7 | $R_{ab}$ | $R_{at}$ |
| C1-83 | 7 | $R_{ak}$ | $R_{at}$ | C1-84 | 7 | $R_{an}$ | $R_{at}$ |
| C1-85 | 7 | $R_{aa}$ | $R_{au}$ | C1-86 | 7 | $R_{ab}$ | $R_{au}$ |
| C1-87 | 7 | $R_{ak}$ | $R_{au}$ | C1-88 | 7 | $R_{an}$ | $R_{au}$ |
| C1-89 | 7 | $R_{aa}$ | $R_{av}$ | C1-90 | 7 | $R_{ab}$ | $R_{av}$ |
| C1-91 | 7 | $R_{ak}$ | $R_{av}$ | C1-92 | 7 | $R_{an}$ | $R_{av}$ |
| C1-93 | 7 | $R_{aa}$ | $R_{aw}$ | C1-94 | 7 | $R_{ab}$ | $R_{aw}$ |
| C1-95 | 7 | $R_{ak}$ | $R_{aw}$ | C1-96 | 7 | $R_{an}$ | $R_{aw}$ |
| C2-1 | 7 | $R_{aa}$ | $R_{ad}$ | C2-2 | 7 | $R_{aa}$ | $R_{ae}$ |
| C2-3 | 7 | $R_{ab}$ | $R_{ad}$ | C2-4 | 7 | $R_{ab}$ | $R_{ae}$ |
| C2-5 | 7 | $R_{ac}$ | $R_{ad}$ | C2-6 | 7 | $R_{ac}$ | $R_{ae}$ |
| C2-7 | 7 | $R_{af}$ | $R_{aa}$ | C2-8 | 7 | $R_{af}$ | $R_{ab}$ |
| C2-9 | 7 | $R_{af}$ | $R_{ac}$ | C2-10 | 7 | $R_{af}$ | $R_{ad}$ |
| C2-11 | 7 | $R_{af}$ | $R_{ae}$ | C2-12 | 7 | $R_{ag}$ | $R_{aa}$ |
| C2-13 | 7 | $R_{ag}$ | $R_{ab}$ | C2-14 | 7 | $R_{ag}$ | $R_{ac}$ |
| C2-15 | 7 | $R_{ag}$ | $R_{ad}$ | C2-16 | 7 | $R_{ag}$ | $R_{ae}$ |
| C2-17 | 7 | $R_{ah}$ | $R_{aa}$ | C2-18 | 7 | $R_{ah}$ | $R_{ab}$ |
| C2-19 | 7 | $R_{ah}$ | $R_{ac}$ | C2-20 | 7 | $R_{ah}$ | $R_{ad}$ |
| C2-21 | 7 | $R_{ah}$ | $R_{ae}$ | C2-22 | 7 | $R_{ai}$ | $R_{aa}$ |
| C2-23 | 7 | $R_{ai}$ | $R_{ab}$ | C2-24 | 7 | $R_{ai}$ | $R_{ac}$ |
| C2-25 | 7 | $R_{ai}$ | $R_{ad}$ | C2-26 | 7 | $R_{ai}$ | $R_{ae}$ |
| C2-27 | 7 | $R_{aj}$ | $R_{aa}$ | C2-28 | 7 | $R_{aj}$ | $R_{ab}$ |
| C2-29 | 7 | $R_{aj}$ | $R_{ac}$ | C2-30 | 7 | $R_{aj}$ | $R_{ad}$ |
| C2-31 | 7 | $R_{aj}$ | $R_{ae}$ | C2-32 | 7 | $R_{ak}$ | $R_{aa}$ |
| C2-33 | 7 | $R_{ak}$ | $R_{ab}$ | C2-34 | 7 | $R_{ak}$ | $R_{ac}$ |
| C2-35 | 7 | $R_{ak}$ | $R_{ad}$ | C2-36 | 7 | $R_{ak}$ | $R_{ae}$ |
| C2-37 | 7 | $R_{al}$ | $R_{aa}$ | C2-38 | 7 | $R_{al}$ | $R_{ab}$ |
| C2-39 | 7 | $R_{al}$ | $R_{ac}$ | C2-40 | 7 | $R_{al}$ | $R_{ad}$ |
| C2-41 | 7 | $R_{al}$ | $R_{ae}$ | C2-42 | 7 | $R_{am}$ | $R_{aa}$ |
| C2-43 | 7 | $R_{am}$ | $R_{ab}$ | C2-44 | 7 | $R_{am}$ | $R_{ac}$ |
| C2-45 | 7 | $R_{am}$ | $R_{ad}$ | C2-46 | 7 | $R_{am}$ | $R_{ae}$ |
| C2-47 | 7 | $R_{an}$ | $R_{aa}$ | C2-48 | 7 | $R_{an}$ | $R_{ab}$ |
| C2-49 | 7 | $R_{an}$ | $R_{ac}$ | C2-50 | 7 | $R_{an}$ | $R_{ad}$ |
| C2-51 | 7 | $R_{an}$ | $R_{ae}$ | C2-52 | 7 | $R_{ao}$ | $R_{aa}$ |
| C2-53 | 7 | $R_{ao}$ | $R_{ad}$ | C2-54 | 7 | $R_{ao}$ | $R_{ae}$ |
| C2-55 | 7 | $R_{ao}$ | $R_{ax}$ | C2-56 | 7 | $R_{ap}$ | $R_{aa}$ |
| C2-57 | 7 | $R_{ap}$ | $R_{ad}$ | C2-58 | 7 | $R_{ap}$ | $R_{ae}$ |
| C2-59 | 7 | $R_{ap}$ | $R_{ax}$ | C2-60 | 7 | $R_{aq}$ | $R_{aa}$ |
| C2-61 | 7 | $R_{aq}$ | $R_{ad}$ | C2-62 | 7 | $R_{aq}$ | $R_{ae}$ |
| C2-63 | 7 | $R_{aq}$ | $R_{ax}$ | C2-64 | 7 | $R_{ar}$ | $R_{aa}$ |
| C2-65 | 7 | $R_{ar}$ | $R_{ad}$ | C2-66 | 7 | $R_{ar}$ | $R_{ae}$ |
| C2-67 | 7 | $R_{ar}$ | $R_{ax}$ | C2-68 | 7 | $R_{as}$ | $R_{aa}$ |
| C2-69 | 7 | $R_{as}$ | $R_{ad}$ | C2-70 | 7 | $R_{as}$ | $R_{ae}$ |
| C2-71 | 7 | $R_{as}$ | $R_{ax}$ | C2-72 | 7 | $R_{at}$ | $R_{aa}$ |
| C2-73 | 7 | $R_{at}$ | $R_{ad}$ | C2-74 | 7 | $R_{at}$ | $R_{ae}$ |
| C2-75 | 7 | $R_{at}$ | $R_{ax}$ | C2-76 | 7 | $R_{au}$ | $R_{aa}$ |
| C2-77 | 7 | $R_{au}$ | $R_{ad}$ | C2-78 | 7 | $R_{au}$ | $R_{ae}$ |
| C2-79 | 7 | $R_{au}$ | $R_{ax}$ | C2-80 | 7 | $R_{av}$ | $R_{aa}$ |
| C2-81 | 7 | $R_{av}$ | $R_{ad}$ | C2-82 | 7 | $R_{av}$ | $R_{ae}$ |
| C2-83 | 7 | $R_{av}$ | $R_{ax}$ | C2-84 | 7 | $R_{aw}$ | $R_{aa}$ |
| C2-85 | 7 | $R_{aw}$ | $R_{ad}$ | C2-86 | 7 | $R_{aw}$ | $R_{ae}$ |
| C2-87 | 7 | $R_{aw}$ | $R_{ax}$ | — | — | — | — |
| C3-1 | 8 | $R_{aa}$ | $R_{aa}$ | C3-2 | 8 | $R_{ac}$ | $R_{aa}$ |
| C3-3 | 8 | $R_{ad}$ | $R_{aa}$ | C3-4 | 8 | $R_{ay}$ | $R_{aa}$ |
| C3-5 | 8 | $R_{am}$ | $R_{aa}$ | C3-6 | 8 | $R_{aa}$ | $R_{ab}$ |
| C3-7 | 8 | $R_{ac}$ | $R_{ab}$ | C3-8 | 8 | $R_{ad}$ | $R_{ab}$ |
| C3-9 | 8 | $R_{ay}$ | $R_{ab}$ | C3-10 | 8 | $R_{am}$ | $R_{ab}$ |
| C3-11 | 8 | $R_{aa}$ | $R_{ac}$ | C3-12 | 8 | $R_{ac}$ | $R_{ac}$ |
| C3-13 | 8 | $R_{ad}$ | $R_{ac}$ | C3-14 | 8 | $R_{ay}$ | $R_{ac}$ |
| C3-15 | 8 | $R_{am}$ | $R_{ac}$ | C3-16 | 8 | $R_{aa}$ | $R_{ak}$ |
| C3-17 | 8 | $R_{ac}$ | $R_{ak}$ | C3-18 | 8 | $R_{ad}$ | $R_{ak}$ |
| C3-19 | 8 | $R_{ay}$ | $R_{ak}$ | C3-20 | 8 | $R_{am}$ | $R_{ak}$ |
| C3-21 | 8 | $R_{aa}$ | $R_{az}$ | C3-22 | 8 | $R_{ac}$ | $R_{az}$ |
| C3-23 | 8 | $R_{ad}$ | $R_{az}$ | C3-24 | 8 | $R_{ay}$ | $R_{az}$ |
| C3-25 | 8 | $R_{am}$ | $R_{az}$ | C3-26 | 8 | $R_{aa}$ | $R_{ae}$ |
| C3-27 | 8 | $R_{ac}$ | $R_{ae}$ | C3-28 | 8 | $R_{ad}$ | $R_{ae}$ |
| C3-29 | 8 | $R_{ay}$ | $R_{ae}$ | C3-30 | 8 | $R_{am}$ | $R_{ae}$ |
| C3-31 | 8 | $R_{aa}$ | $R_{ao}$ | C3-32 | 8 | $R_{ab}$ | $R_{ao}$ |
| C3-33 | 8 | $R_{ak}$ | $R_{ao}$ | C3-34 | 8 | $R_{an}$ | $R_{ao}$ |
| C3-35 | 8 | $R_{aa}$ | $R_{ap}$ | C3-36 | 8 | $R_{ab}$ | $R_{ap}$ |
| C3-37 | 8 | $R_{ak}$ | $R_{ap}$ | C3-38 | 8 | $R_{an}$ | $R_{ap}$ |

-continued

| Compound | Formula | $R_{11}$ | $R_{12}$ | Compound | Formula | $R_{11}$ | $R_{12}$ |
|---|---|---|---|---|---|---|---|
| C3-39 | 8 | $R_{aa}$ | $R_{aq}$ | C3-40 | 8 | $R_{ab}$ | $R_{aq}$ |
| C3-41 | 8 | $R_{ak}$ | $R_{aq}$ | C3-42 | 8 | $R_{an}$ | $R_{aq}$ |
| C3-43 | 8 | $R_{aa}$ | $R_{ar}$ | C3-44 | 8 | $R_{ab}$ | $R_{ar}$ |
| C3-45 | 8 | $R_{ak}$ | $R_{ar}$ | C3-46 | 8 | $R_{an}$ | $R_{ar}$ |
| C3-47 | 8 | $R_{aa}$ | $R_{as}$ | C3-48 | 8 | $R_{ab}$ | $R_{as}$ |
| C3-49 | 8 | $R_{ak}$ | $R_{as}$ | C3-50 | 8 | $R_{an}$ | $R_{as}$ |
| C3-51 | 8 | $R_{aa}$ | $R_{at}$ | C3-52 | 8 | $R_{ab}$ | $R_{at}$ |
| C3-53 | 8 | $R_{ak}$ | $R_{at}$ | C3-54 | 8 | $R_{an}$ | $R_{at}$ |
| C3-55 | 8 | $R_{aa}$ | $R_{au}$ | C3-56 | 8 | $R_{ab}$ | $R_{au}$ |
| C3-57 | 8 | $R_{ak}$ | $R_{au}$ | C3-58 | 8 | $R_{an}$ | $R_{au}$ |
| C3-59 | 8 | $R_{aa}$ | $R_{av}$ | C3-60 | 8 | $R_{ab}$ | $R_{av}$ |
| C3-61 | 8 | $R_{ak}$ | $R_{av}$ | C3-62 | 8 | $R_{an}$ | $R_{av}$ |
| C3-63 | 8 | $R_{aa}$ | $R_{aw}$ | C3-64 | 8 | $R_{ab}$ | $R_{aw}$ |
| C3-65 | 8 | $R_{ak}$ | $R_{aw}$ | C3-66 | 8 | $R_{an}$ | $R_{aw}$ |
| C4-1 | 9 | $R_{aa}$ | $R_{aa}$ | C4-2 | 9 | $R_{ab}$ | $R_{aa}$ |
| C4-3 | 9 | $R_{ad}$ | $R_{aa}$ | C4-4 | 9 | $R_{ay}$ | $R_{aa}$ |
| C4-5 | 9 | $R_{am}$ | $R_{aa}$ | C4-6 | 9 | $R_{aa}$ | $R_{ab}$ |
| C4-7 | 9 | $R_{ab}$ | $R_{ab}$ | C4-8 | 9 | $R_{ad}$ | $R_{ab}$ |
| C4-9 | 9 | $R_{ay}$ | $R_{ab}$ | C4-10 | 9 | $R_{am}$ | $R_{ab}$ |
| C4-11 | 9 | $R_{aa}$ | $R_{ac}$ | C4-12 | 9 | $R_{ab}$ | $R_{ac}$ |
| C4-13 | 9 | $R_{ad}$ | $R_{ac}$ | C4-14 | 9 | $R_{ay}$ | $R_{ac}$ |
| C4-15 | 9 | $R_{am}$ | $R_{ac}$ | C4-16 | 9 | $R_{aa}$ | $R_{ak}$ |
| C4-17 | 9 | $R_{ab}$ | $R_{ak}$ | C4-18 | 9 | $R_{ad}$ | $R_{ak}$ |
| C4-19 | 9 | $R_{ay}$ | $R_{ak}$ | C4-20 | 9 | $R_{am}$ | $R_{ak}$ |
| C4-21 | 9 | $R_{aa}$ | $R_{az}$ | C4-22 | 9 | $R_{ab}$ | $R_{az}$ |
| C4-23 | 9 | $R_{ad}$ | $R_{az}$ | C4-24 | 9 | $R_{ay}$ | $R_{az}$ |
| C4-25 | 9 | $R_{am}$ | $R_{az}$ | C4-26 | 9 | $R_{aa}$ | $R_{ae}$ |
| C4-27 | 9 | $R_{ab}$ | $R_{ae}$ | C4-28 | 9 | $R_{ad}$ | $R_{ae}$ |
| C4-29 | 9 | $R_{ay}$ | $R_{ae}$ | C4-30 | 9 | $R_{am}$ | $R_{ae}$ |
| C4-31 | 9 | $R_{aa}$ | $R_{ao}$ | C4-32 | 9 | $R_{ad}$ | $R_{ao}$ |
| C4-33 | 9 | $R_{ae}$ | $R_{ao}$ | C4-34 | 9 | $R_{ax}$ | $R_{ao}$ |
| C4-35 | 9 | $R_{aa}$ | $R_{ap}$ | C4-36 | 9 | $R_{ad}$ | $R_{ap}$ |
| C4-37 | 9 | $R_{ae}$ | $R_{ap}$ | C4-38 | 9 | $R_{ax}$ | $R_{ap}$ |
| C4-39 | 9 | $R_{aa}$ | $R_{aq}$ | C4-40 | 9 | $R_{ad}$ | $R_{aq}$ |
| C4-41 | 9 | $R_{ae}$ | $R_{aq}$ | C4-42 | 9 | $R_{ax}$ | $R_{aq}$ |
| C4-43 | 9 | $R_{aa}$ | $R_{ar}$ | C4-44 | 9 | $R_{ad}$ | $R_{ar}$ |
| C4-45 | 9 | $R_{ae}$ | $R_{ar}$ | C4-46 | 9 | $R_{ax}$ | $R_{ar}$ |
| C4-47 | 9 | $R_{aa}$ | $R_{as}$ | C4-48 | 9 | $R_{ad}$ | $R_{as}$ |
| C4-49 | 9 | $R_{ae}$ | $R_{as}$ | C4-50 | 9 | $R_{ax}$ | $R_{as}$ |
| C4-51 | 9 | $R_{aa}$ | $R_{at}$ | C4-52 | 9 | $R_{ad}$ | $R_{at}$ |
| C4-53 | 9 | $R_{ae}$ | $R_{at}$ | C4-54 | 9 | $R_{ax}$ | $R_{at}$ |
| C4-55 | 9 | $R_{aa}$ | $R_{au}$ | C4-56 | 9 | $R_{ad}$ | $R_{au}$ |
| C4-57 | 9 | $R_{ae}$ | $R_{au}$ | C4-58 | 9 | $R_{ax}$ | $R_{au}$ |
| C4-59 | 9 | $R_{aa}$ | $R_{av}$ | C4-60 | 9 | $R_{ad}$ | $R_{av}$ |
| C4-61 | 9 | $R_{ae}$ | $R_{av}$ | C4-62 | 9 | $R_{ax}$ | $R_{av}$ |
| C4-63 | 9 | $R_{aa}$ | $R_{aw}$ | C4-64 | 9 | $R_{ad}$ | $R_{aw}$ |
| C4-65 | 9 | $R_{ae}$ | $R_{aw}$ | C4-66 | 9 | $R_{ax}$ | $R_{aw}$ |
| C5-1 | 10 | $R_{aa}$ | $R_{aa}$ | C5-2 | 10 | $R_{ab}$ | $R_{aa}$ |
| C5-3 | 10 | $R_{ad}$ | $R_{aa}$ | C5-4 | 10 | $R_{ay}$ | $R_{aa}$ |
| C5-5 | 10 | $R_{am}$ | $R_{aa}$ | C5-6 | 10 | $R_{aa}$ | $R_{ab}$ |
| C5-7 | 10 | $R_{ab}$ | $R_{ab}$ | C5-8 | 10 | $R_{ad}$ | $R_{ab}$ |
| C5-9 | 10 | $R_{ay}$ | $R_{ab}$ | C5-10 | 10 | $R_{am}$ | $R_{ab}$ |
| C5-11 | 10 | $R_{aa}$ | $R_{ac}$ | C5-12 | 10 | $R_{ab}$ | $R_{ac}$ |
| C5-13 | 10 | $R_{ad}$ | $R_{ac}$ | C5-14 | 10 | $R_{ay}$ | $R_{ac}$ |
| C5-15 | 10 | $R_{am}$ | $R_{ac}$ | C5-16 | 10 | $R_{aa}$ | $R_{ak}$ |
| C5-17 | 10 | $R_{ab}$ | $R_{ak}$ | C5-18 | 10 | $R_{ad}$ | $R_{ak}$ |
| C5-19 | 10 | $R_{ay}$ | $R_{ak}$ | C5-20 | 10 | $R_{am}$ | $R_{ak}$ |
| C5-21 | 10 | $R_{aa}$ | $R_{an}$ | C5-22 | 10 | $R_{ab}$ | $R_{an}$ |
| C5-23 | 10 | $R_{ad}$ | $R_{an}$ | C5-24 | 10 | $R_{ay}$ | $R_{an}$ |
| C5-25 | 10 | $R_{am}$ | $R_{an}$ | C5-26 | 10 | $R_{aa}$ | $R_{ae}$ |
| C5-27 | 10 | $R_{ab}$ | $R_{ae}$ | C5-28 | 10 | $R_{ad}$ | $R_{ae}$ |
| C5-29 | 10 | $R_{ay}$ | $R_{ae}$ | C5-30 | 10 | $R_{am}$ | $R_{ae}$ |
| C5-31 | 10 | $R_{aa}$ | $R_{ao}$ | C5-32 | 10 | $R_{ab}$ | $R_{ao}$ |
| C5-33 | 10 | $R_{ak}$ | $R_{ao}$ | C5-34 | 10 | $R_{an}$ | $R_{ao}$ |
| C5-35 | 10 | $R_{aa}$ | $R_{ap}$ | C5-36 | 10 | $R_{ab}$ | $R_{ap}$ |
| C5-37 | 10 | $R_{ak}$ | $R_{ap}$ | C5-38 | 10 | $R_{an}$ | $R_{ap}$ |
| C5-39 | 10 | $R_{aa}$ | $R_{aq}$ | C5-40 | 10 | $R_{ab}$ | $R_{aq}$ |
| C5-41 | 10 | $R_{ak}$ | $R_{aq}$ | C5-42 | 10 | $R_{an}$ | $R_{aq}$ |
| C5-43 | 10 | $R_{aa}$ | $R_{ar}$ | C5-44 | 10 | $R_{ab}$ | $R_{ar}$ |
| C5-45 | 10 | $R_{ak}$ | $R_{ar}$ | C5-46 | 10 | $R_{an}$ | $R_{ar}$ |
| C5-47 | 10 | $R_{aa}$ | $R_{as}$ | C5-48 | 10 | $R_{ab}$ | $R_{as}$ |
| C5-49 | 10 | $R_{ak}$ | $R_{as}$ | C5-50 | 10 | $R_{an}$ | $R_{as}$ |
| C5-51 | 10 | $R_{aa}$ | $R_{at}$ | C5-52 | 10 | $R_{ab}$ | $R_{at}$ |
| C5-53 | 10 | $R_{ak}$ | $R_{at}$ | C5-54 | 10 | $R_{an}$ | $R_{at}$ |
| C5-55 | 10 | $R_{aa}$ | $R_{au}$ | C5-56 | 10 | $R_{ab}$ | $R_{au}$ |
| C5-57 | 10 | $R_{ak}$ | $R_{au}$ | C5-58 | 10 | $R_{an}$ | $R_{au}$ |

-continued

| Compound | Formula | $R_{11}$ | $R_{12}$ | Compound | Formula | $R_{11}$ | $R_{12}$ |
|---|---|---|---|---|---|---|---|
| C5-59 | 10 | $R_{aa}$ | $R_{av}$ | C5-60 | 10 | $R_{ab}$ | $R_{av}$ |
| C5-61 | 10 | $R_{ak}$ | $R_{av}$ | C5-62 | 10 | $R_{an}$ | $R_{av}$ |
| C5-63 | 10 | $R_{aa}$ | $R_{aw}$ | C5-64 | 10 | $R_{ab}$ | $R_{aw}$ |
| C5-65 | 10 | $R_{ak}$ | $R_{aw}$ | C5-66 | 10 | $R_{an}$ | $R_{aw}$ |
| C6-1 | 11 | $R_{aa}$ | $R_{aa}$ | C6-2 | 11 | $R_{ac}$ | $R_{aa}$ |
| C6-3 | 11 | $R_{ad}$ | $R_{aa}$ | C6-4 | 11 | $R_{ay}$ | $R_{aa}$ |
| C6-5 | 11 | $R_{am}$ | $R_{aa}$ | C6-6 | 11 | $R_{aa}$ | $R_{ab}$ |
| C6-7 | 11 | $R_{ac}$ | $R_{ab}$ | C6-8 | 11 | $R_{ad}$ | $R_{ab}$ |
| C6-9 | 11 | $R_{ay}$ | $R_{ab}$ | C6-10 | 11 | $R_{am}$ | $R_{ab}$ |
| C6-11 | 11 | $R_{aa}$ | $R_{ac}$ | C6-12 | 11 | $R_{ac}$ | $R_{ac}$ |
| C6-13 | 11 | $R_{ad}$ | $R_{ac}$ | C6-14 | 11 | $R_{ay}$ | $R_{ac}$ |
| C6-15 | 11 | $R_{am}$ | $R_{ac}$ | C6-16 | 11 | $R_{aa}$ | $R_{ak}$ |
| C6-17 | 11 | $R_{ac}$ | $R_{ak}$ | C6-18 | 11 | $R_{ad}$ | $R_{ak}$ |
| C6-19 | 11 | $R_{ay}$ | $R_{ak}$ | C6-20 | 11 | $R_{am}$ | $R_{ak}$ |
| C6-21 | 11 | $R_{aa}$ | $R_{az}$ | C6-22 | 11 | $R_{ac}$ | $R_{az}$ |
| C6-23 | 11 | $R_{ad}$ | $R_{az}$ | C6-24 | 11 | $R_{ay}$ | $R_{az}$ |
| C6-25 | 11 | $R_{am}$ | $R_{az}$ | C6-26 | 11 | $R_{aa}$ | $R_{ae}$ |
| C6-27 | 11 | $R_{ac}$ | $R_{ae}$ | C6-28 | 11 | $R_{ad}$ | $R_{ae}$ |
| C6-29 | 11 | $R_{ay}$ | $R_{ae}$ | C6-30 | 11 | $R_{am}$ | $R_{ae}$ |
| C6-31 | 11 | $R_{aa}$ | $R_{ao}$ | C6-32 | 11 | $R_{ad}$ | $R_{ao}$ |
| C6-33 | 11 | $R_{ae}$ | $R_{ao}$ | C6-34 | 11 | $R_{ax}$ | $R_{ao}$ |
| C6-35 | 11 | $R_{aa}$ | $R_{ap}$ | C6-36 | 11 | $R_{ad}$ | $R_{ap}$ |
| C6-37 | 11 | $R_{ae}$ | $R_{ap}$ | C6-38 | 11 | $R_{ax}$ | $R_{ap}$ |
| C6-39 | 11 | $R_{aa}$ | $R_{aq}$ | C6-40 | 11 | $R_{ad}$ | $R_{aq}$ |
| C6-41 | 11 | $R_{ae}$ | $R_{aq}$ | C6-42 | 11 | $R_{ax}$ | $R_{aq}$ |
| C6-43 | 11 | $R_{aa}$ | $R_{ar}$ | C6-44 | 11 | $R_{ad}$ | $R_{ar}$ |
| C6-45 | 11 | $R_{ae}$ | $R_{ar}$ | C6-46 | 11 | $R_{ax}$ | $R_{ar}$ |
| C6-47 | 11 | $R_{aa}$ | $R_{as}$ | C6-48 | 11 | $R_{ad}$ | $R_{as}$ |
| C6-49 | 11 | $R_{ae}$ | $R_{as}$ | C6-50 | 11 | $R_{ax}$ | $R_{as}$ |
| C6-51 | 11 | $R_{aa}$ | $R_{at}$ | C6-52 | 11 | $R_{ad}$ | $R_{at}$ |
| C6-53 | 11 | $R_{ae}$ | $R_{at}$ | C6-54 | 11 | $R_{ax}$ | $R_{at}$ |
| C6-55 | 11 | $R_{aa}$ | $R_{au}$ | C6-56 | 11 | $R_{ad}$ | $R_{au}$ |
| C6-57 | 11 | $R_{ae}$ | $R_{au}$ | C6-58 | 11 | $R_{ax}$ | $R_{au}$ |
| C6-59 | 11 | $R_{aa}$ | $R_{av}$ | C6-60 | 11 | $R_{ad}$ | $R_{av}$ |
| C6-61 | 11 | $R_{ae}$ | $R_{av}$ | C6-62 | 11 | $R_{ax}$ | $R_{av}$ |
| C6-63 | 11 | $R_{aa}$ | $R_{aw}$ | C6-64 | 11 | $R_{ad}$ | $R_{aw}$ |
| C6-65 | 11 | $R_{ae}$ | $R_{aw}$ | C6-66 | 11 | $R_{ax}$ | $R_{aw}$ |
| C7-1 | 12 | — | $R_{aa}$ | C7-2 | 12 | — | $R_{ab}$ |
| C7-3 | 12 | — | $R_{ad}$ | C7-4 | 12 | — | $R_{ba}$ |
| C7-5 | 12 | — | $R_{bb}$ | C7-6 | 12 | — | $R_{bc}$ |
| C7-7 | 12 | — | $R_{bd}$ | C7-8 | 12 | — | $R_{be}$ |
| C7-9 | 12 | — | $R_{bf}$ | C7-10 | 12 | — | $R_{bg}$ |
| C7-11 | 12 | — | $R_{bh}$ | C7-12 | 12 | — | $R_{bi}$ |
| C7-13 | 13 | — | $R_{aa}$ | C7-14 | 13 | — | $R_{ab}$ |
| C7-15 | 13 | — | $R_{ad}$ | C7-16 | 13 | — | $R_{ba}$ |
| C7-17 | 13 | — | $R_{bb}$ | C7-18 | 13 | — | $R_{bc}$ |
| C7-19 | 13 | — | $R_{bd}$ | C7-20 | 13 | — | $R_{be}$ |
| C7-21 | 13 | — | $R_{bf}$ | C7-22 | 13 | — | $R_{bg}$ |
| C7-23 | 13 | — | $R_{bh}$ | C7-24 | 13 | — | $R_{bi}$ |
| C7-25 | 14 | — | $R_{aa}$ | C7-26 | 14 | — | $R_{ab}$ |
| C7-27 | 14 | — | $R_{ad}$ | C7-28 | 14 | — | $R_{ba}$ |
| C7-29 | 14 | — | $R_{bb}$ | C7-30 | 14 | — | $R_{bc}$ |
| C7-31 | 14 | — | $R_{bd}$ | C7-32 | 14 | — | $R_{be}$ |
| C7-33 | 14 | — | $R_{bf}$ | C7-34 | 14 | — | $R_{bg}$ |
| C7-35 | 14 | — | $R_{bh}$ | C7-36 | 14 | — | $R_{bi}$ |
| C7-37 | 15 | — | $R_{aa}$ | C7-38 | 15 | — | $R_{ab}$ |
| C7-39 | 15 | — | $R_{ad}$ | C7-40 | 15 | — | $R_{ba}$ |
| C7-41 | 15 | — | $R_{bb}$ | C7-42 | 15 | — | $R_{bc}$ |
| C7-43 | 15 | — | $R_{bd}$ | C7-44 | 15 | — | $R_{be}$ |
| C7-45 | 15 | — | $R_{bf}$ | C7-46 | 15 | — | $R_{bg}$ |
| C7-47 | 15 | — | $R_{bh}$ | C7-48 | 15 | — | $R_{bi}$ |

Herein, the heteroaryl(ene) may contain at least one heteroatom selected from B, N, O, S, Si, and P. Also, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

Herein, the term "(C1-C30)alkyl(ene)" is meant to be a linear or branched alkyl(ene) having 1 to 30 carbon atoms constituting the chain, in which the number of carbon atoms is preferably 1 to 20, and more preferably 1 to 10. The above alkyl may include methyl, ethyl, n-propyl, iso-propyl, n-butyl, iso-butyl, tert-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl(ene)" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered) heterocycloalkyl" is meant to be a cycloalkyl having 3 to 7, preferably 5 to 7, ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms, in which the number of the ring backbone carbon atoms is preferably 6 to 25, more preferably 6 to 18. The above aryl(ene) may be partially saturated, and may comprise a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. The term "(3- to 30-membered)heteroaryl(ene)" is an aryl having 3 to 30 ring backbone atoms, and including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, and dihydroacridinyl. Furthermore, “halogen” includes F, Cl, Br, and I.

Herein, “substituted” in the expression “substituted or unsubstituted” means that a hydrogen atom in a certain functional group is replaced with another atom or another functional group, i.e. a substituent. The substituents of the substituted (C1-C30)alkyl(ene), the substituted (C6-C30)aryl(ene), the substituted (3- to 30-membered)heteroaryl(ene), the substituted (C3-C30)cycloalkyl(ene), the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-C30)arylamino, and the substituted (3- to 30-membered) mono- or polycyclic ring in L, Ar, $R_1$ to $R_3$, $R_{21}$ and $R_{22}$ of formulas 1 to 15, each independently, are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthiol, a (5- to 30-membered) heteroaryl unsubstituted or substituted with a (C6-C30)aryl, a (C6-C30)aryl unsubstituted or substituted with a (5- to 30-membered)heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino unsubstituted or substituted with a (C1-C30)alkyl, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl. As one embodiment, the substituents, each independently, are at least one selected from the group consisting of a cyano, a (C1-C20)alkyl, and a (C6-C25)aryl. As another embodiment, the substituents, each independently, are at least one selected from the group consisting of a cyano, a (C1-C10)alkyl, and a (C6-C18)aryl. For example, the substituents, each independently, are at least one selected from the group consisting of a cyano, a methyl, a phenyl, and a biphenyl.

The compound of formula 1 according to the present disclosure may be produced by a synthetic method known to one skilled in the art, and for example, as shown in the following reaction schemes 1 and 2, but is not limited thereto.

[Reaction Scheme 1]

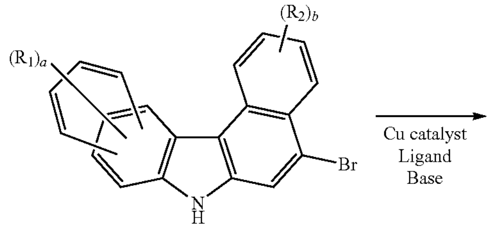

-continued

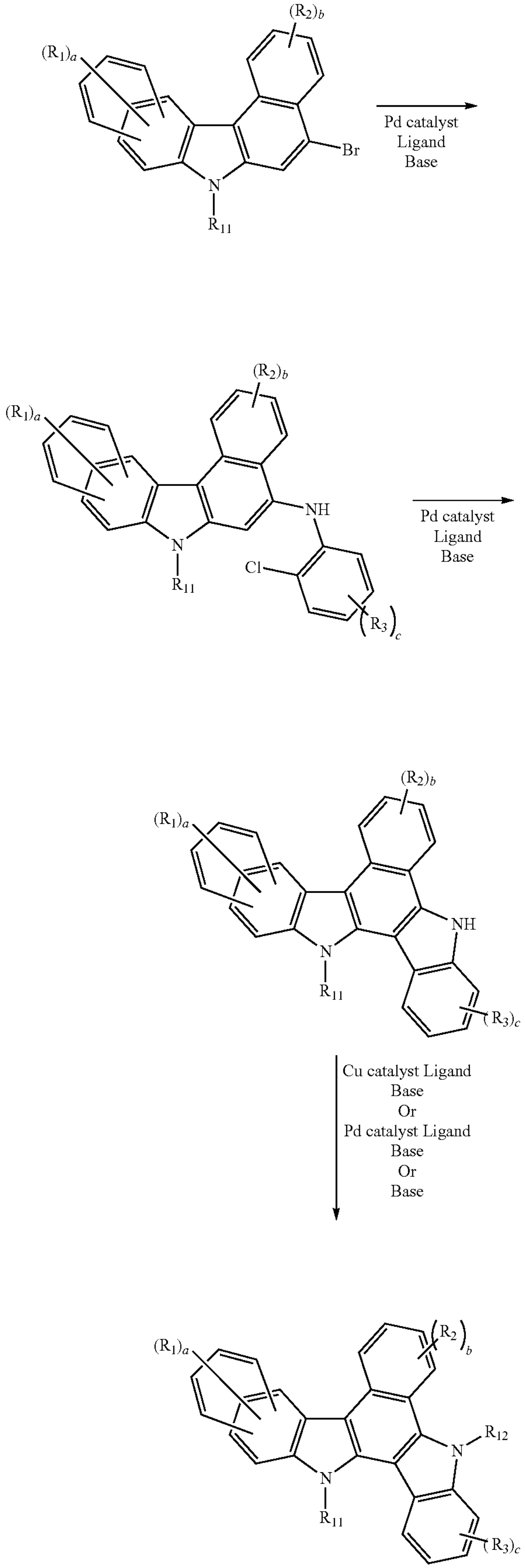

[Reaction Scheme 2]

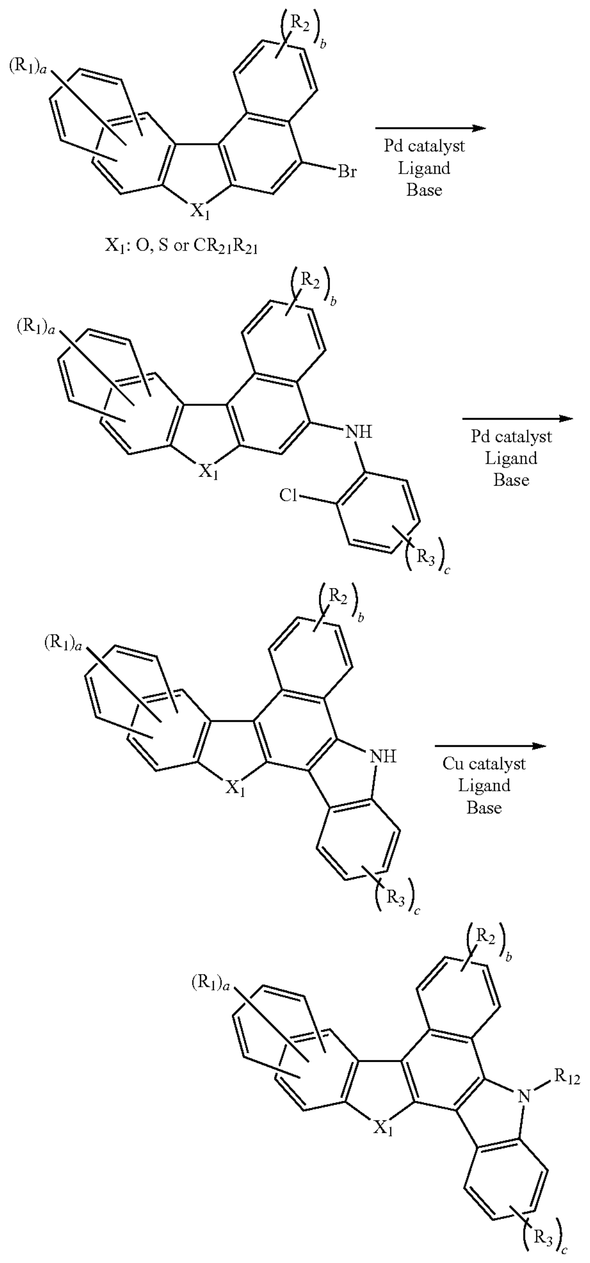

In reaction schemes 1 and 2, $X_1$, $R_{11}$, $R_{12}$, $R_1$ to $R_3$, a, b, and c are as defined in formula 1.

The organic electroluminescent material of the present disclosure may include at least one compound represented by formula 1. The organic electroluminescent compound represented by formula 1 may be comprised in the light-emitting layer, but is not limited thereto. When used in the light-emitting layer, the organic electroluminescent compound of formula 1 may be comprised as a host. Also, the light-emitting layer may further comprise at least one dopant. If necessary, another compound besides the organic electroluminescent compound of formula 1 may be further comprised as a second host material.

According to one embodiment of the present disclosure, the organic electroluminescent material of the present disclosure is a host material, and the host material comprises at least one first host compound and at least one second host compound, and the first host compound may be represented by formula 1. Herein, the weight ratio of the first host material to the second host material is in the range of 1:99 to 99:1.

The second host material may include any one of the compounds represented by the following formulas 21 to 24, but is not limited thereto.

(21)

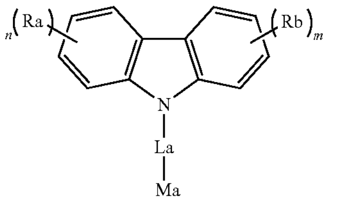

(22)

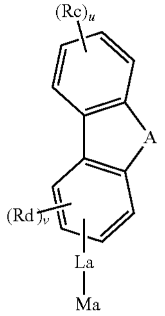

(23)

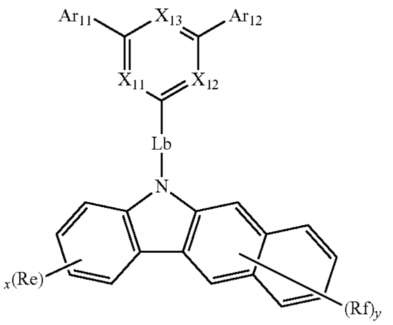

(24)

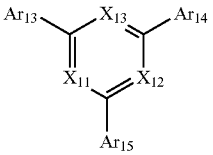

In formulas 21 to 24,

Ma represents a substituted or unsubstituted (C6-C30) aryl, a substituted or unsubstituted mono- or di-(C6-C30) arylamino, or a substituted or unsubstituted (3- to 30-membered)heteroaryl;

La represents a single bond, a substituted or unsubstituted (C6-C30)arylene, or a substituted or unsubstituted (3- to 30-membered)heteroarylene;

A represents S, O, $NR_7$, or $CR_8R_9$;

Ra to Rd, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted (C1-C30)alkyl(C6-C30)arylamino, or a substituted or unsubstituted mono- or di(C6-C30)arylamino; or may be linked to an adjacent substituent to form a substituted or unsubstituted (3- to 30-membered) mono- or polycyclic ring, whose carbon atom(s) may be replaced with at least one heteroatom selected from nitrogen, oxygen, and sulfur;

$R_7$ to $R_9$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; and $R_8$ and $R_9$ may be linked to each other to form a substituted or unsubstituted (3- to 30-membered) mono- or polycyclic ring, whose carbon atom(s) may be replaced with at least one heteroatom selected from nitrogen, oxygen, and sulfur;

$X_{11}$ to $X_{13}$, each independently, represent N or CRg, with a proviso that at least one of $X_{11}$ to $X_{13}$ represent N;

Lb represents a substituted or unsubstituted C10 arylene;

$Ar_{11}$, $Ar_{12}$, and Re to Rg, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino; or may be linked to an adjacent substituent to form a substituted or unsubstituted (3- to 30-membered) mono- or polycyclic ring, whose carbon atom(s) may be replaced with at least one heteroatom selected from nitrogen, oxygen, and sulfur;

$Ar_{13}$ to $Ar_{15}$, each independently, represent a substituted or unsubstituted (C6-C30)aryl;

n, m, u, and x, each independently, represent an integer of 1 to 4, v represents an integer of 1 to 3, y represents an integer of 1 to 6, where if n, m, u, v, x, or y, each independently, is an integer of 2 or more, each of Ra to Rf may be the same or different, and the heteroaryl contains at least one heteroatom selected from B, N, O, S, Si, and P.

The compound represented by any one of formulas 21 to 24 includes the following compounds, but is not limited thereto.

H-1

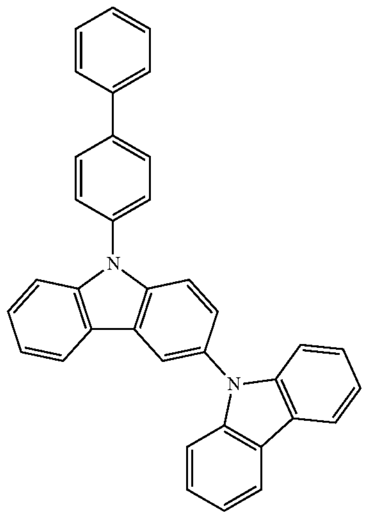

H-2

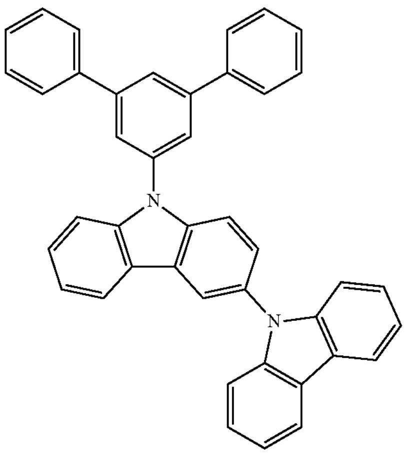

H-3

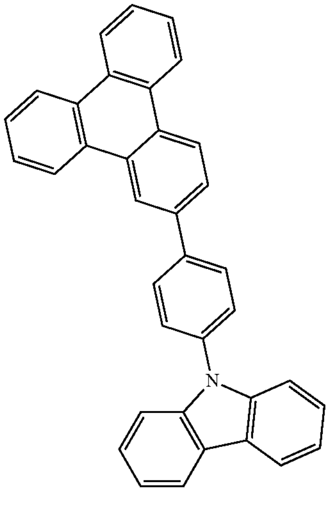

-continued
H-4
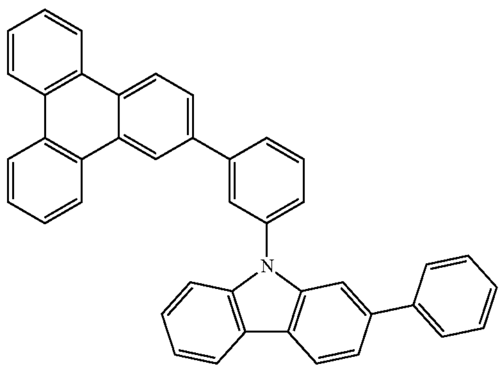
H-5
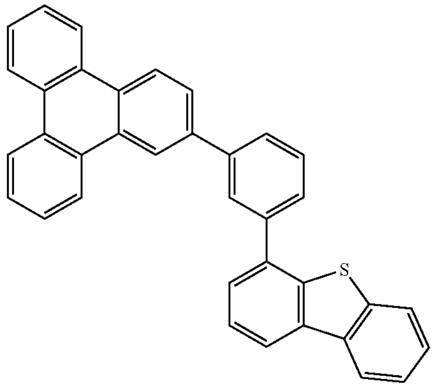
H-6
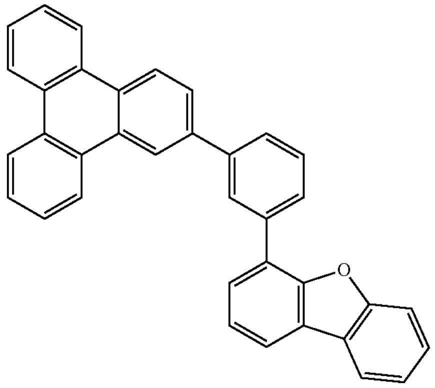
H-7
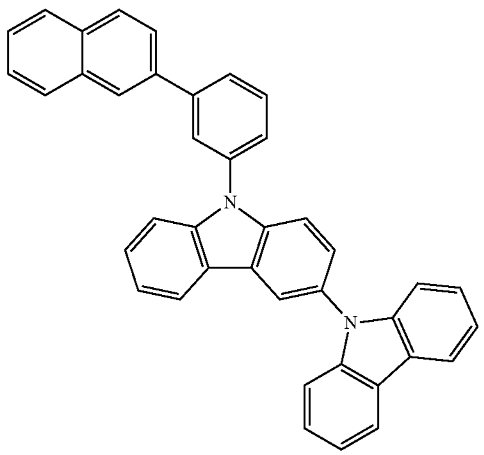
-continued
H-8
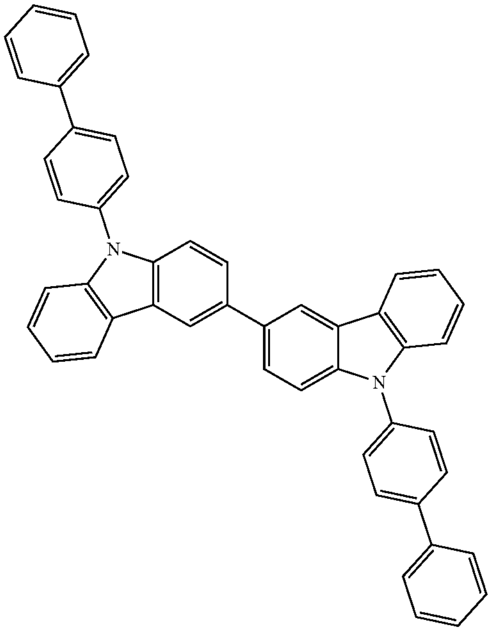
H-9
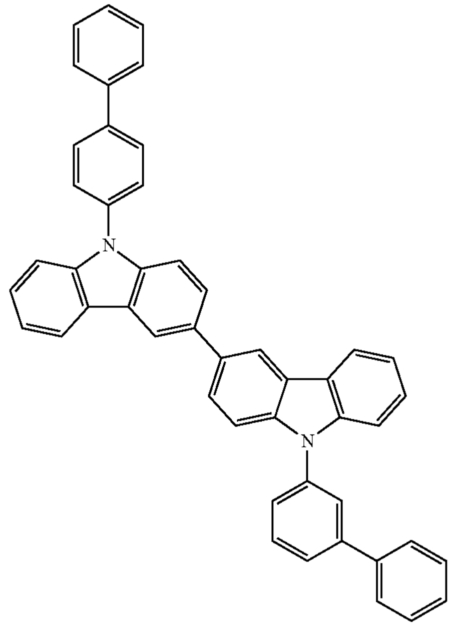

-continued
H-10
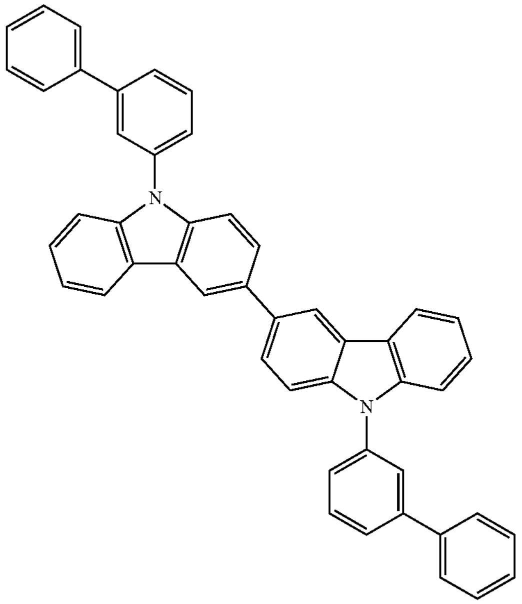
H-11
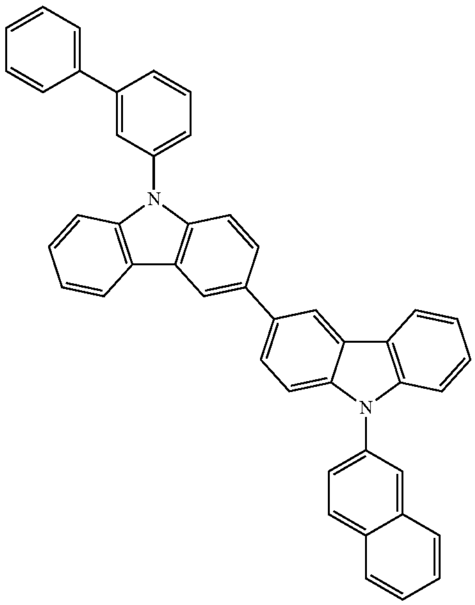
-continued
H-12
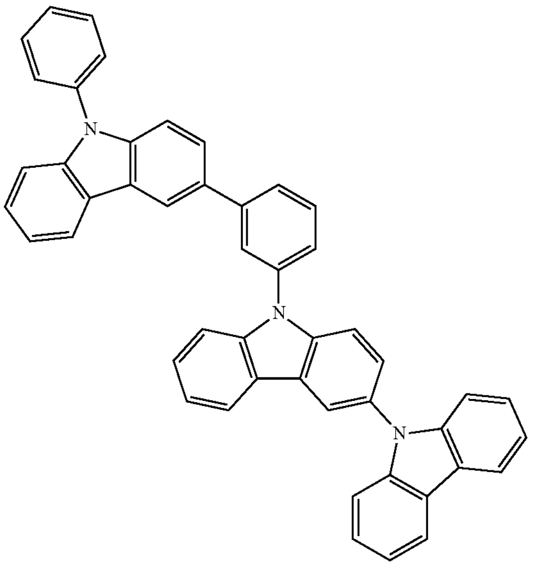
H-13
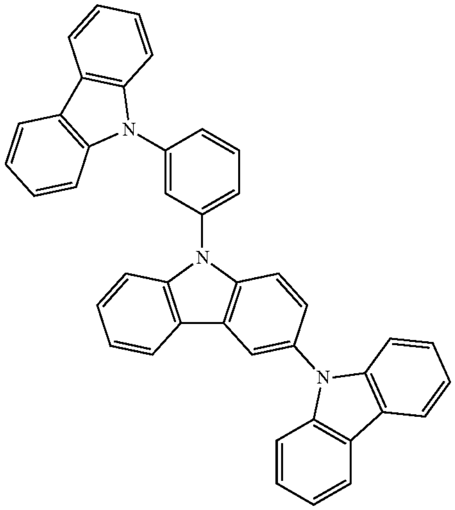
H-14
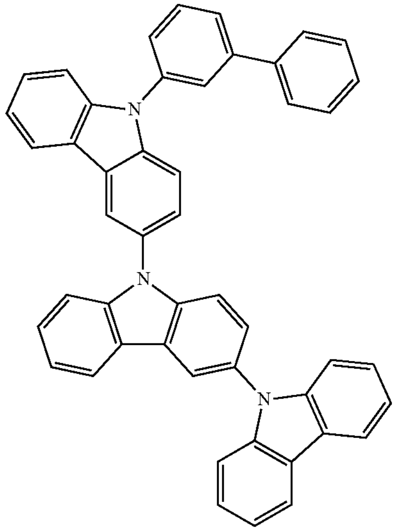

-continued
H-15
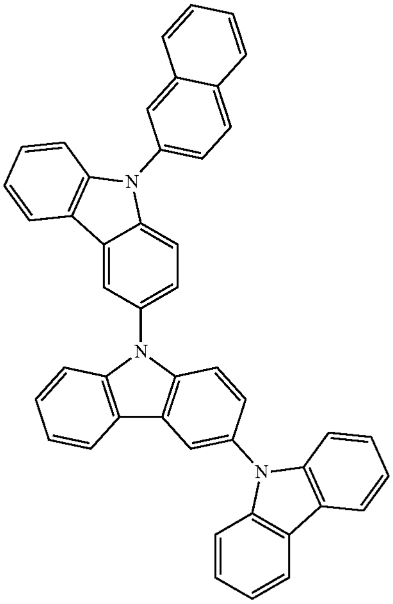
H-16
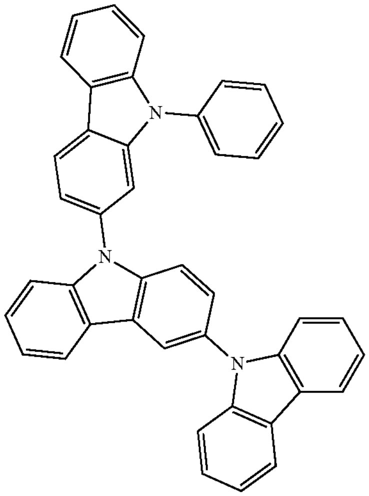
H-17
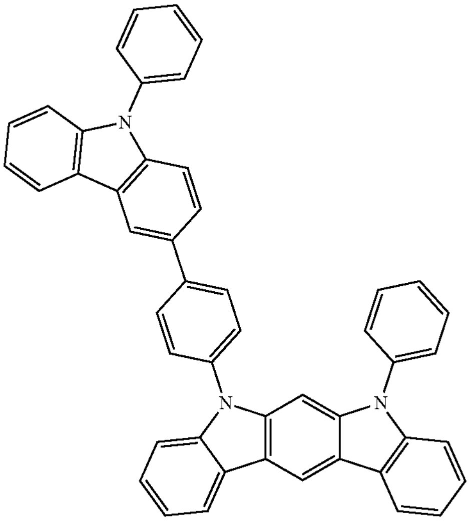
-continued
H-18
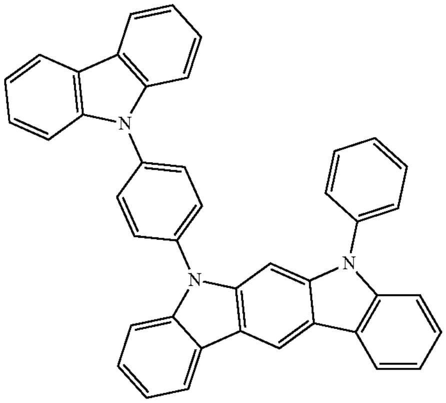
H-19
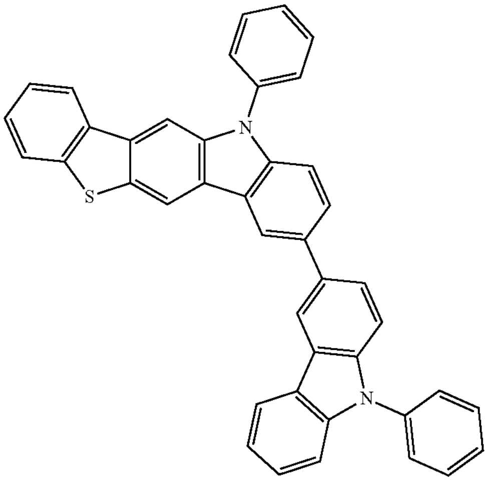
H-20
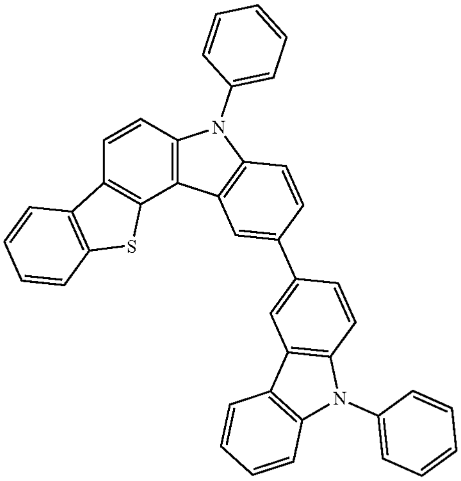

-continued
H-21
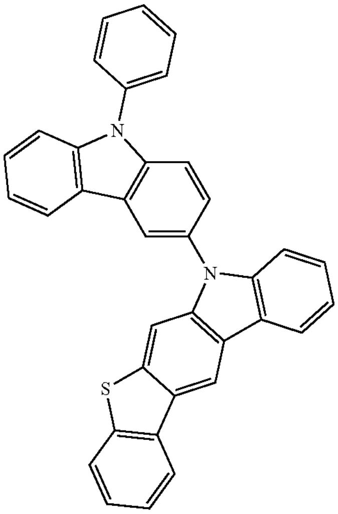
H-22
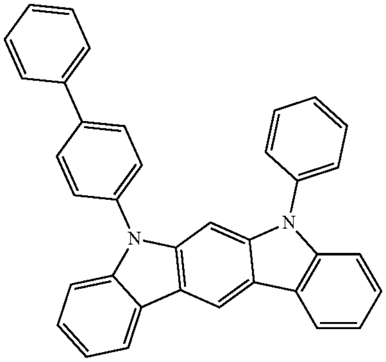
H-23
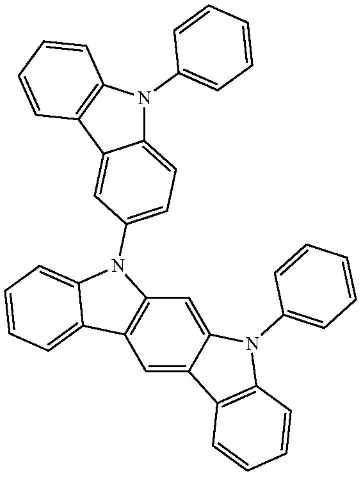
-continued
H-24
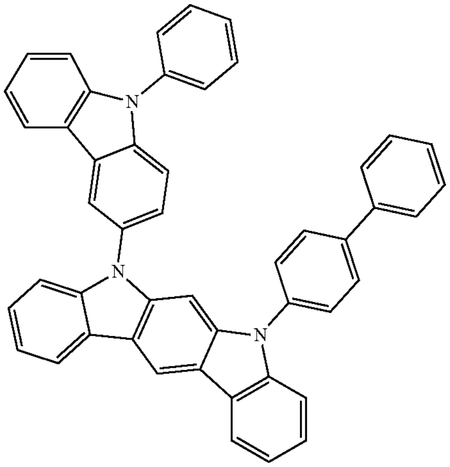
H-25
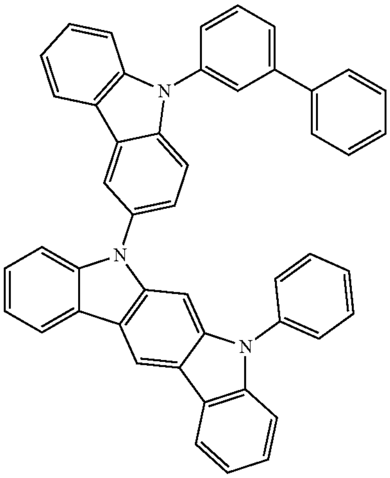
H-26
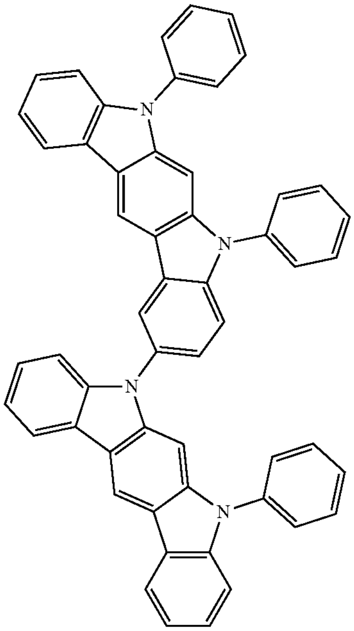

-continued
H-27
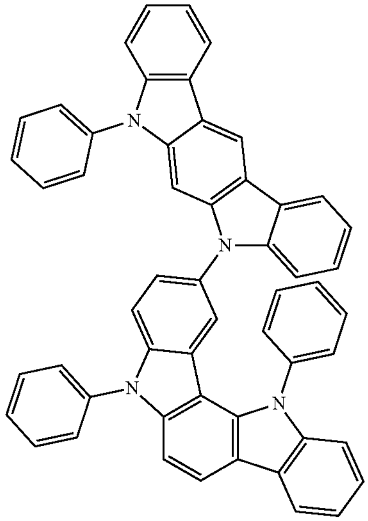
H-28
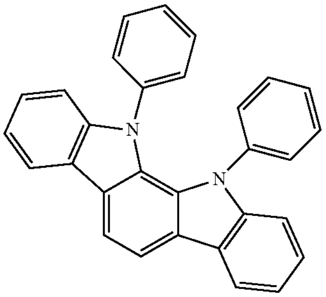
H-29
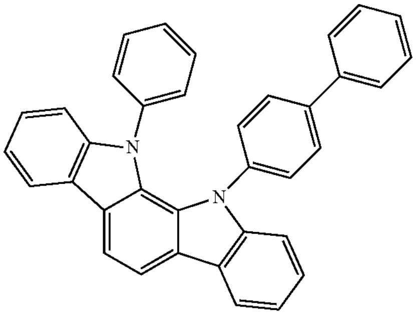
H-30
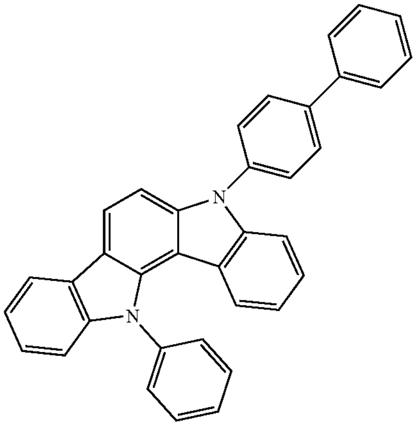
-continued
H-31
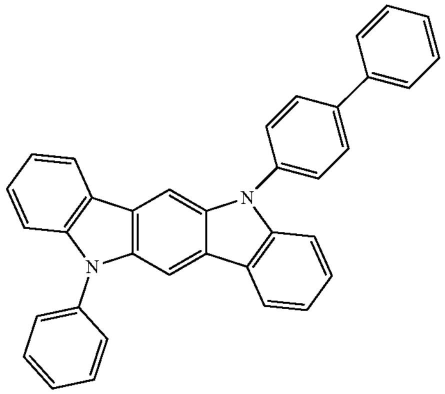
H-32
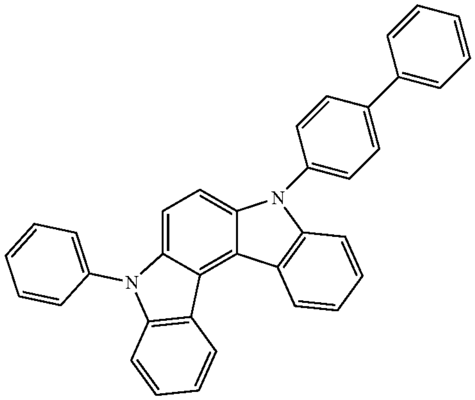
H-33
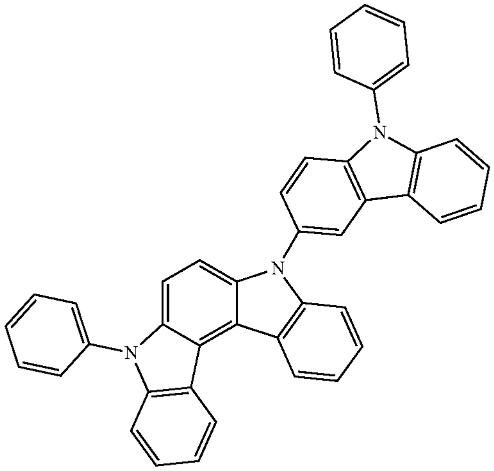

-continued
H-34
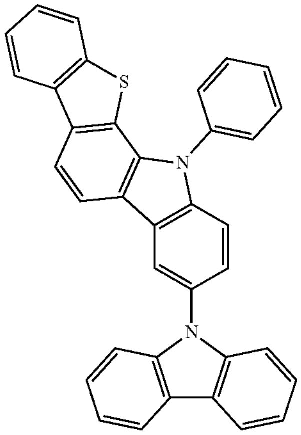
H-35
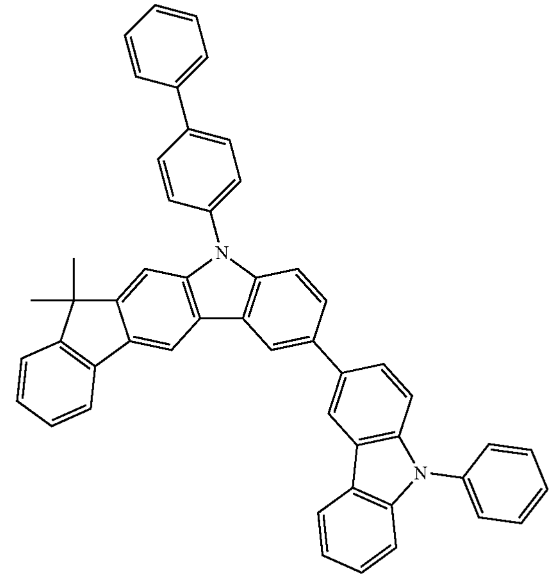
H-36
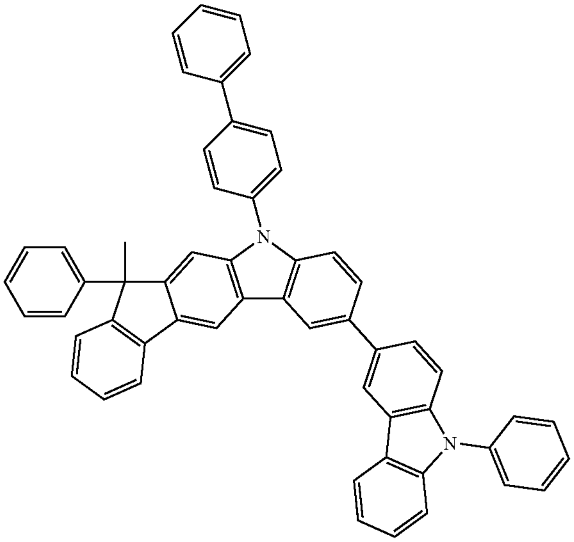
-continued
H-37
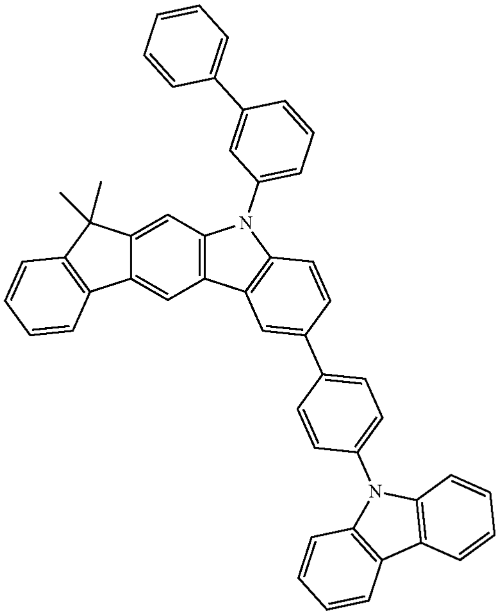
H-38
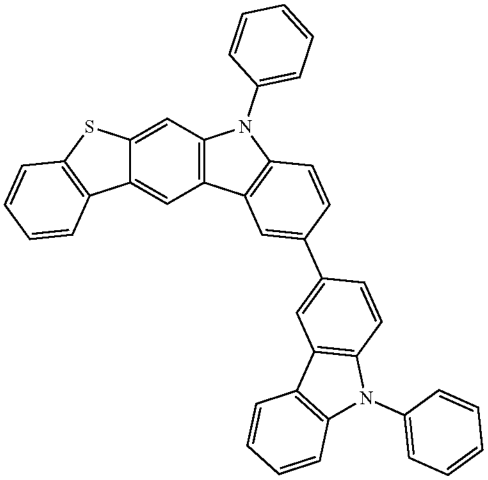
H-39
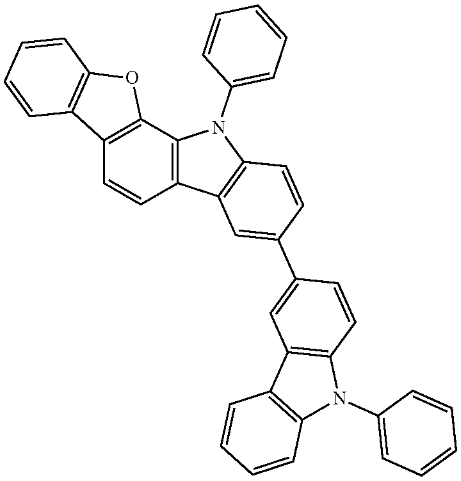

-continued
H-40
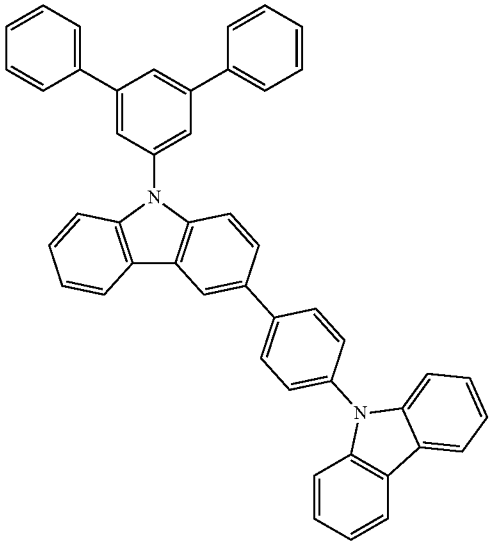
H-41
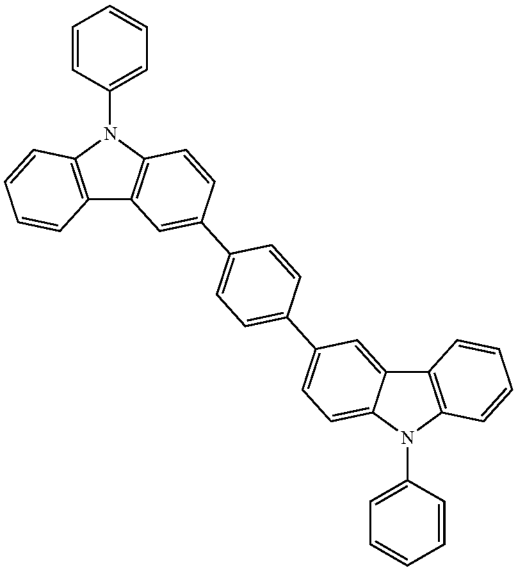
-continued
H-42
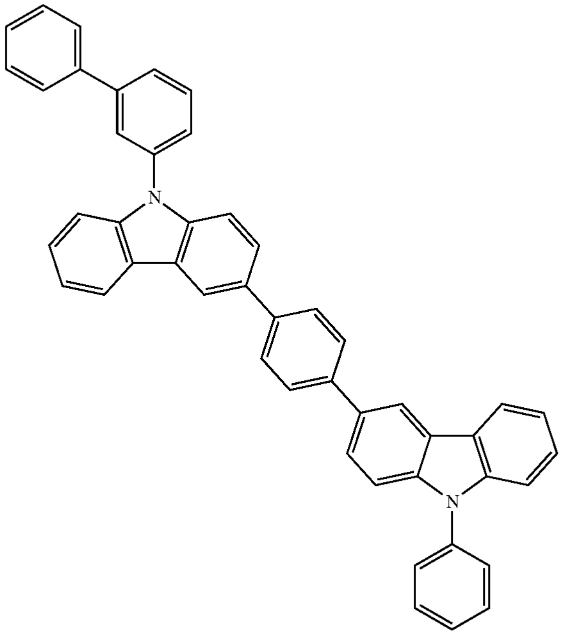
H-43
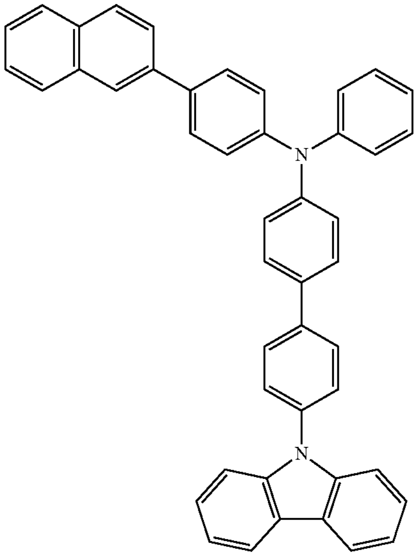

-continued
H-44
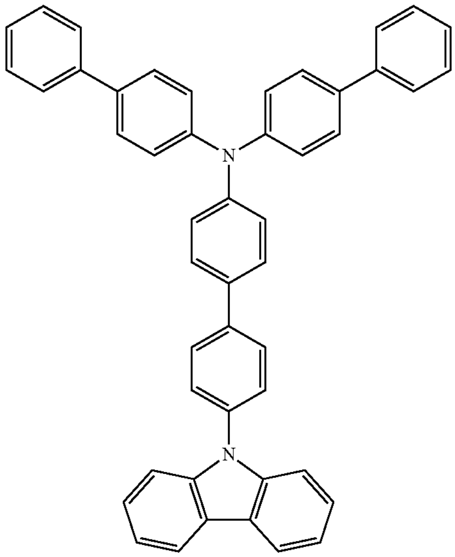
H-45
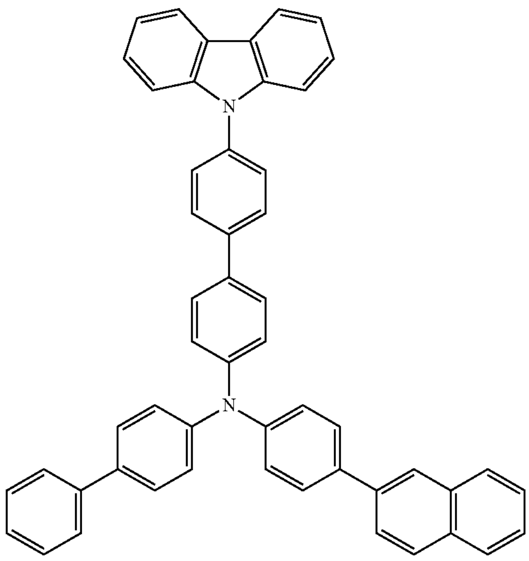
H-46
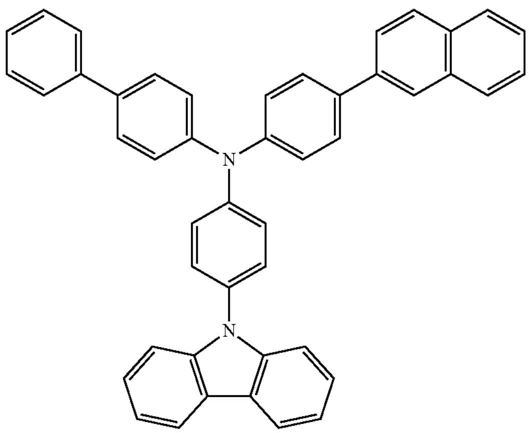
-continued
H-47
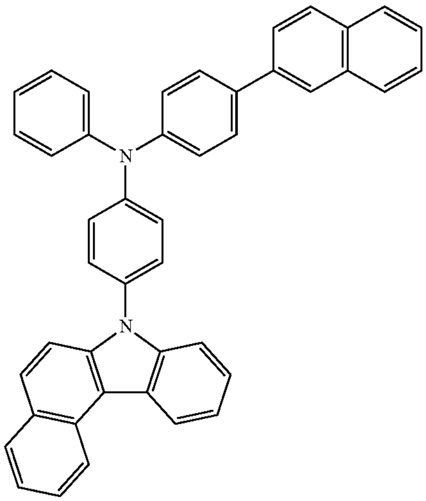
H-48
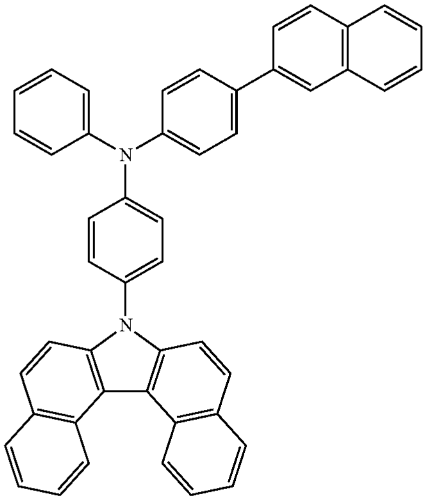
H-49
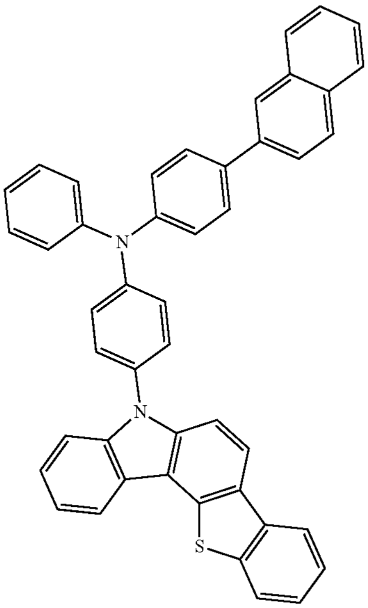

-continued
H-50
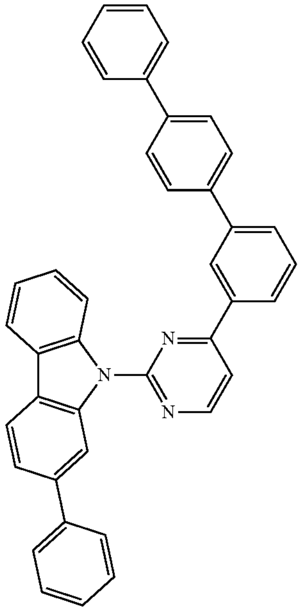
H-51
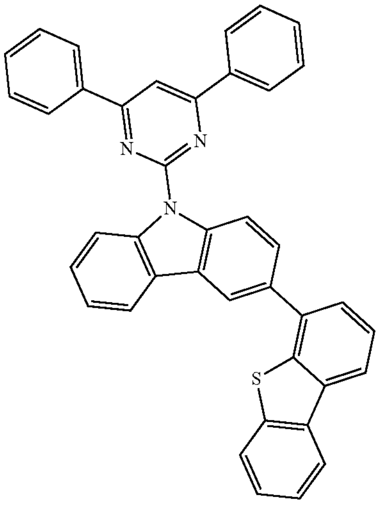
H-52
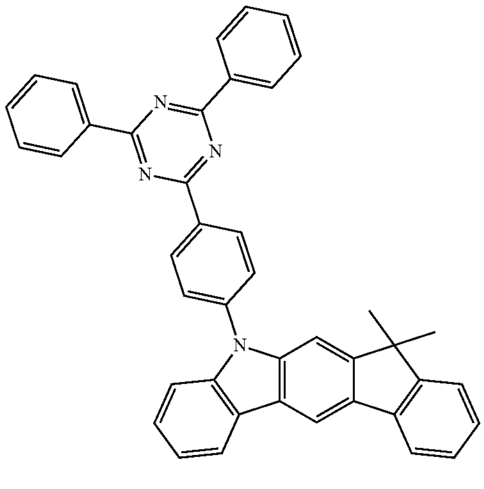
-continued
H-53
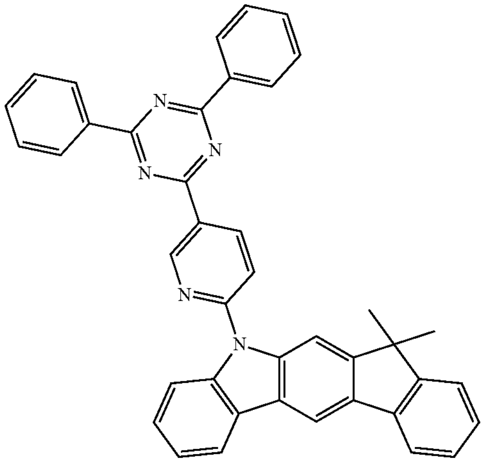
H-54
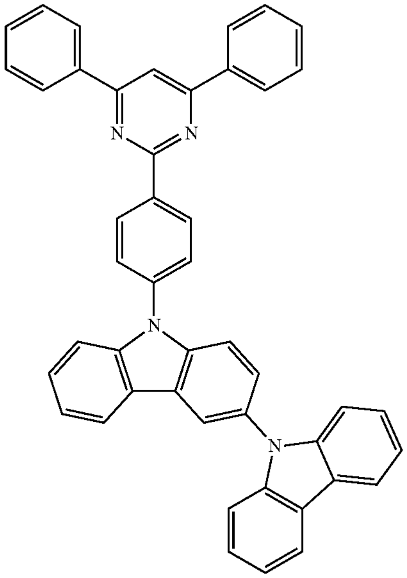
H-55
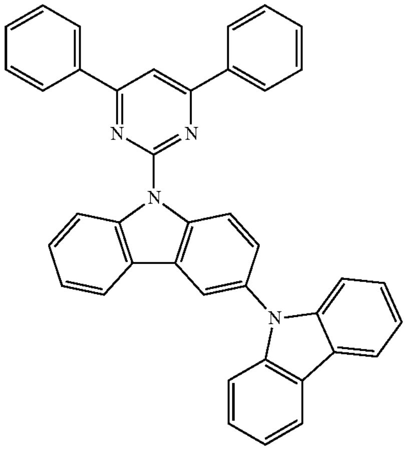

-continued
H-56
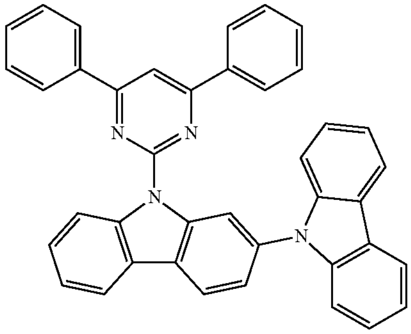
H-57
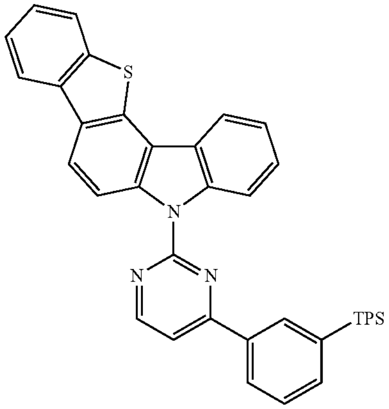
H-58
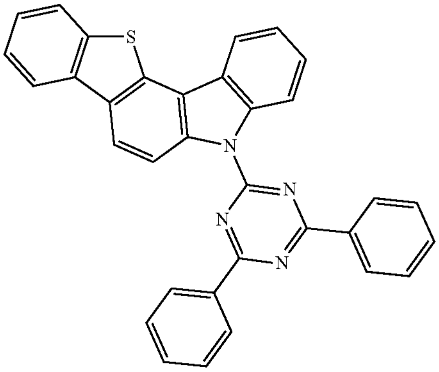
H-59
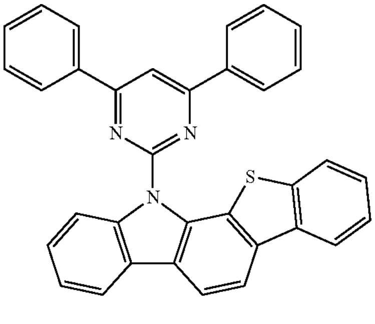
-continued
H-60
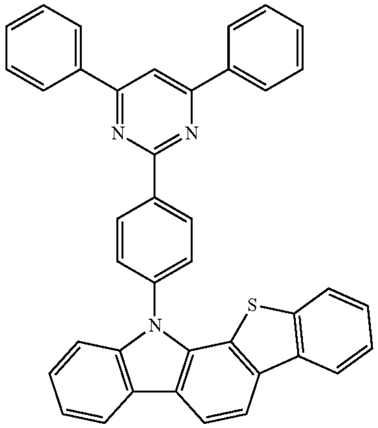
H-61
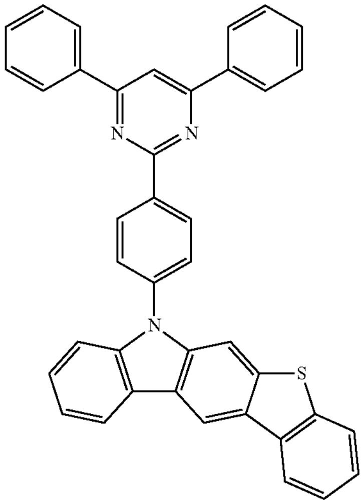
H-62
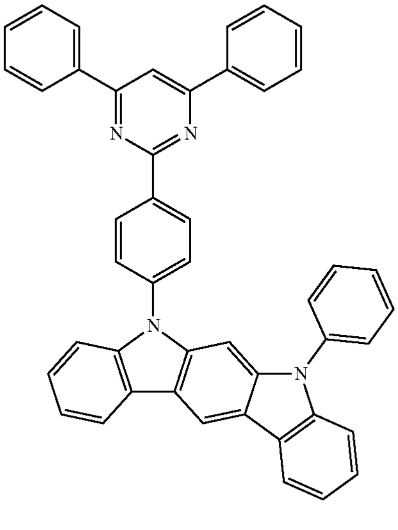

-continued
H-63
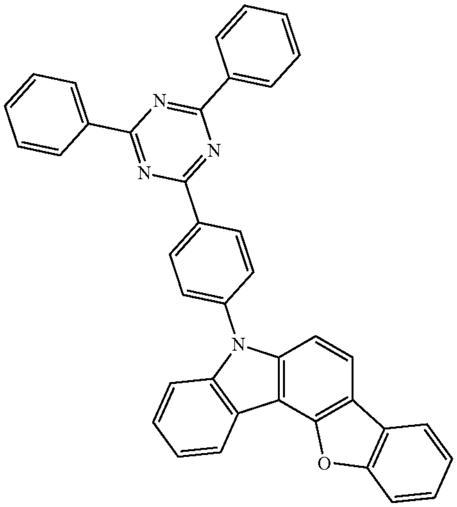
H-64
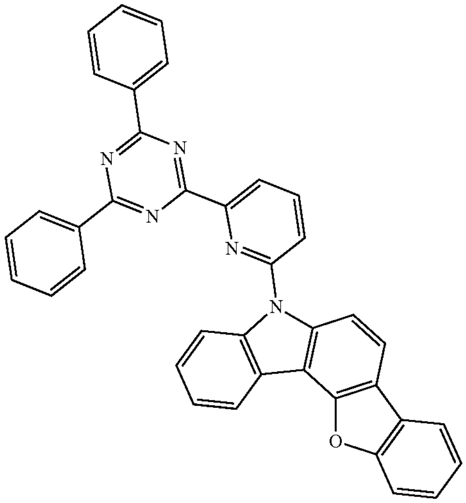
H-65
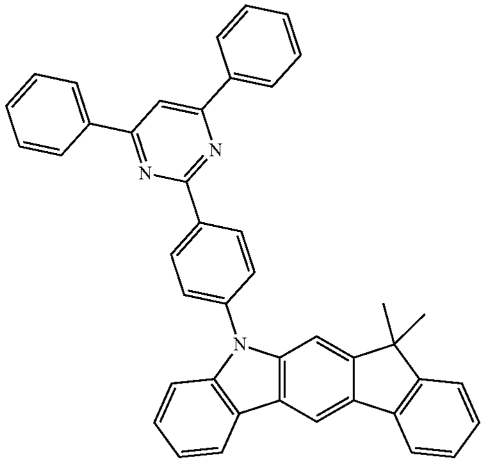
-continued
H-66
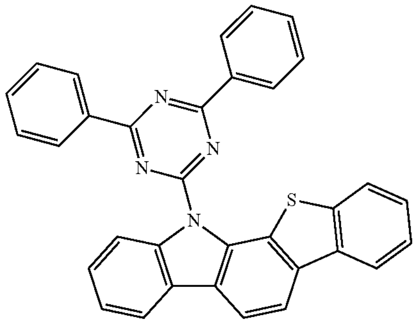
H-67
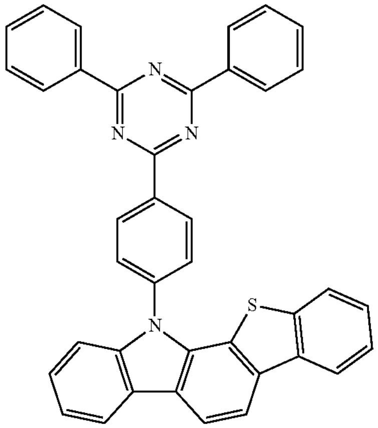
H-68
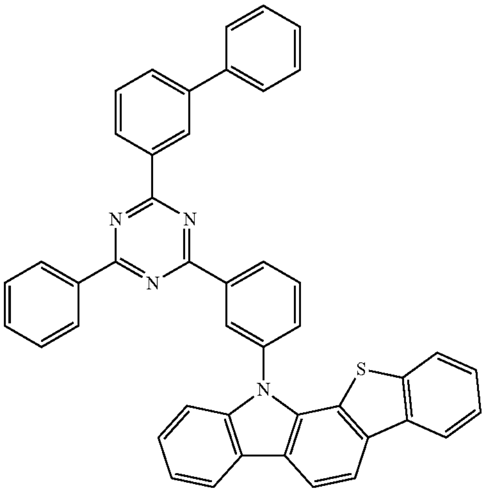

-continued
H-69
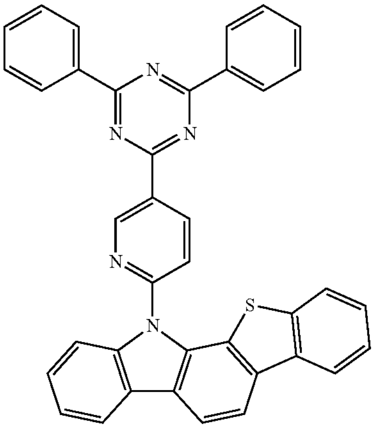
H-70
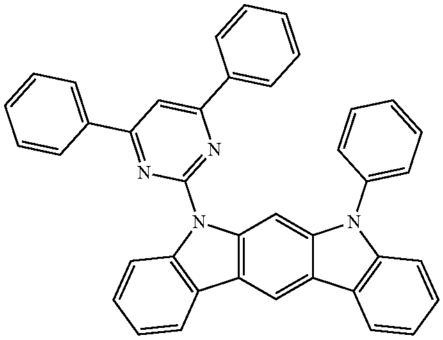
H-71
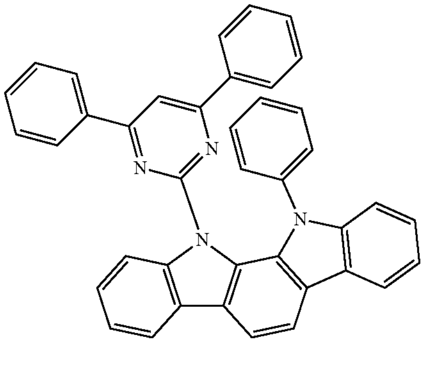
H-72
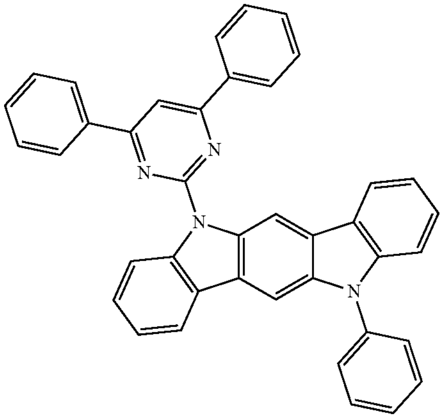
-continued
H-73
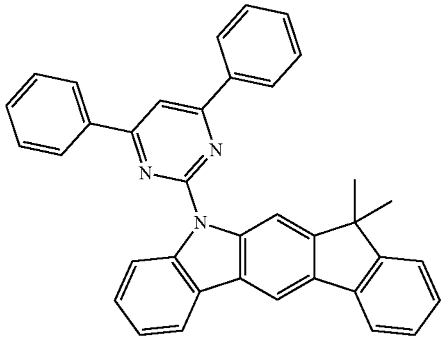
H-74
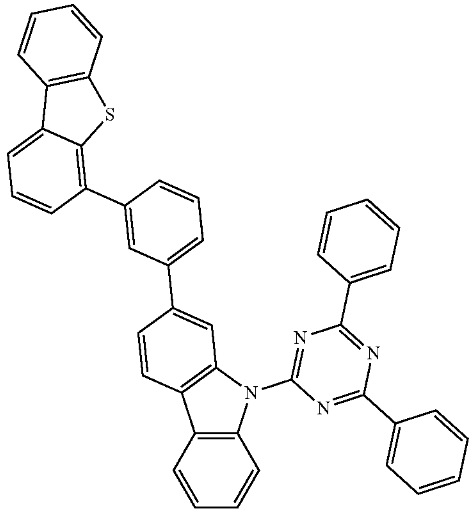
H-75
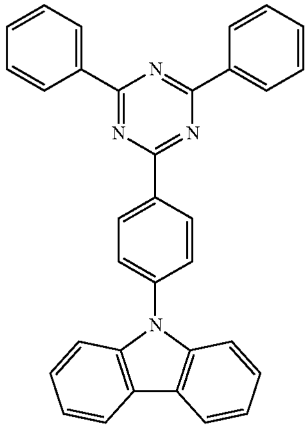

-continued
H-76
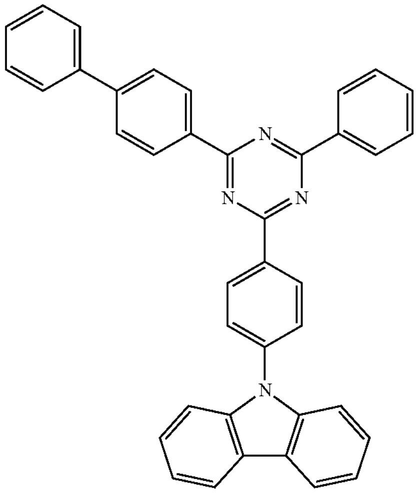
H-77
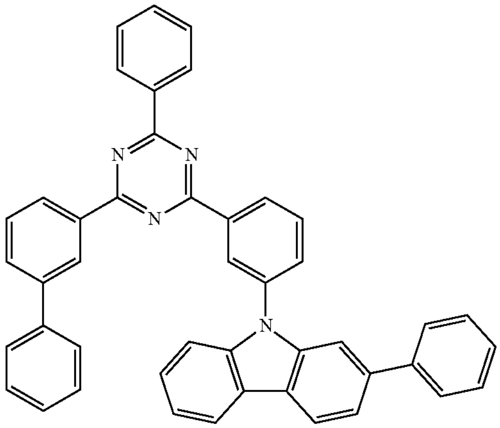
H-78
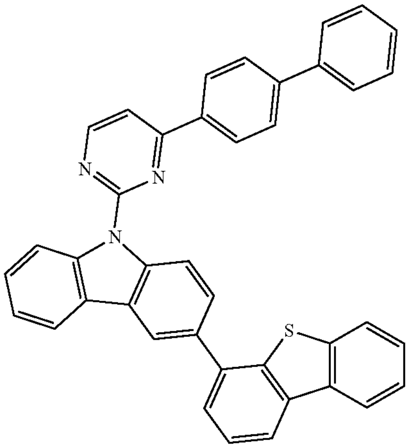
-continued
H-79
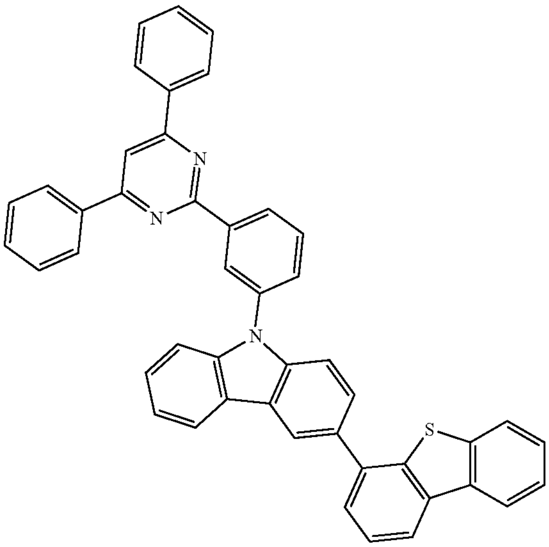
H-80
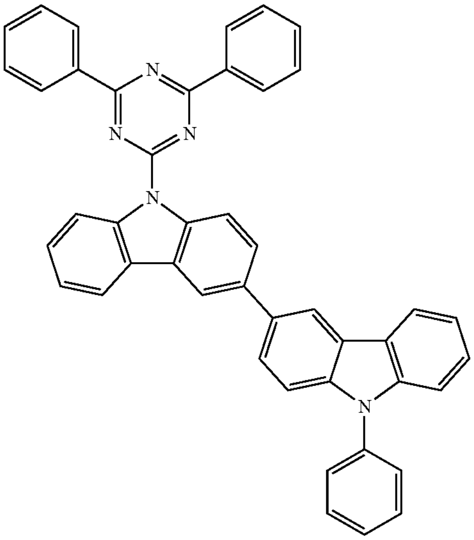
H-81
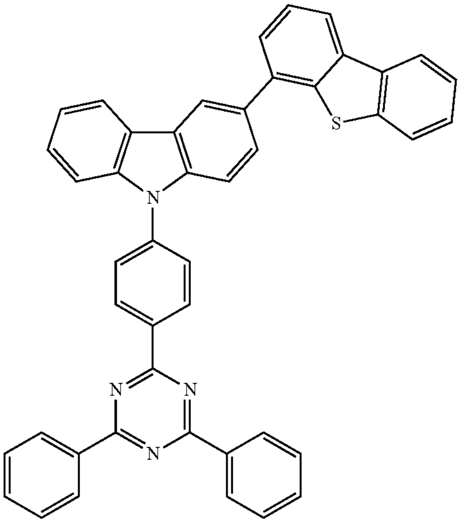

-continued
H-82
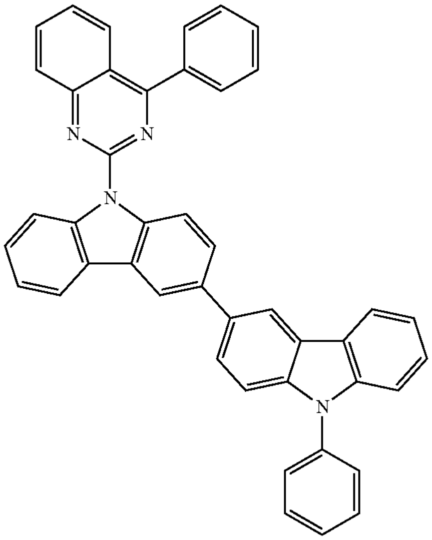
H-83
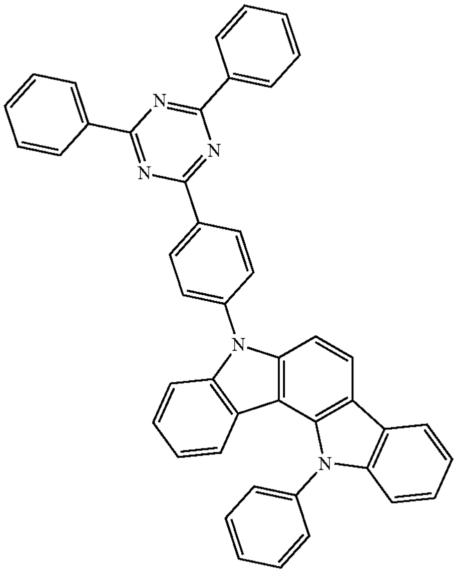
H-84
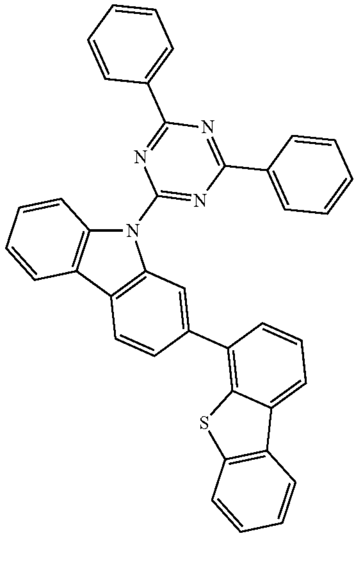
-continued
H-85
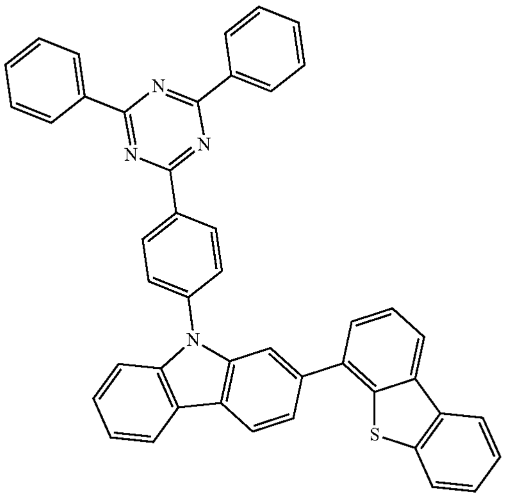
H-86
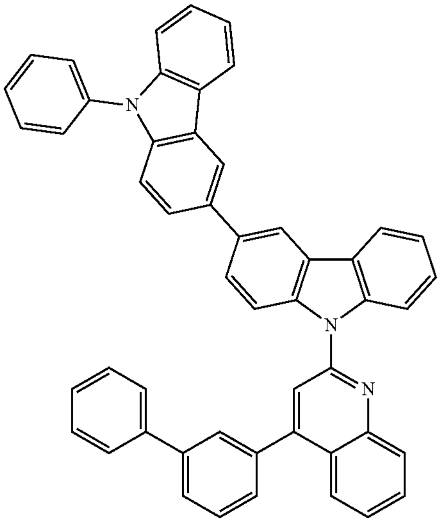
H-87
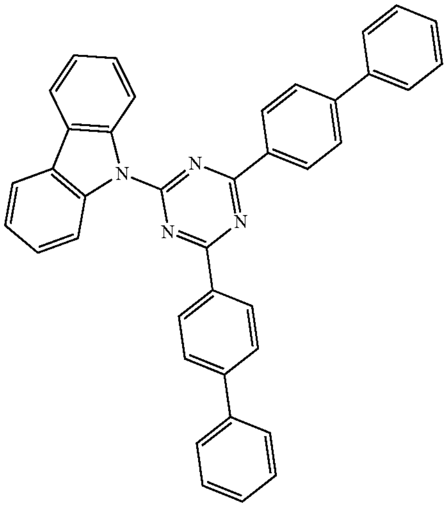

-continued
H-88
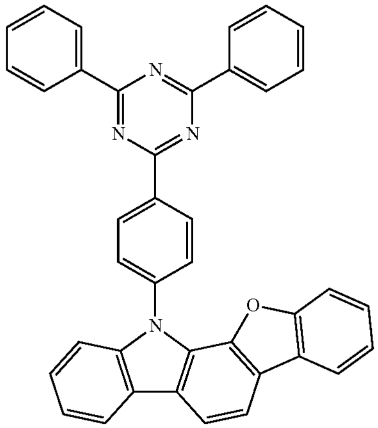
H-89
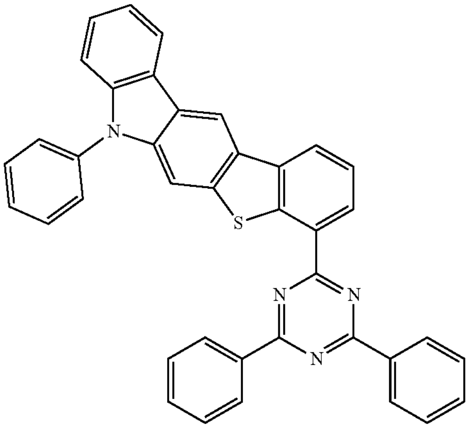
H-90
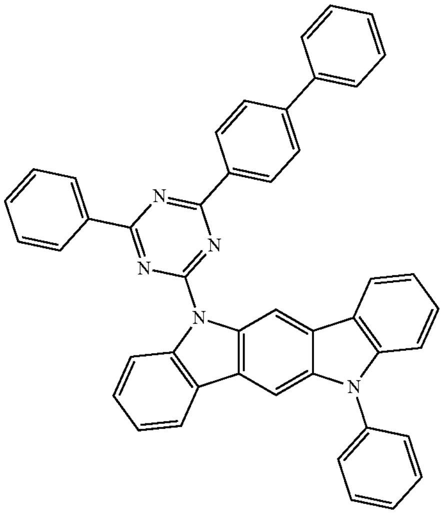
-continued
H-91
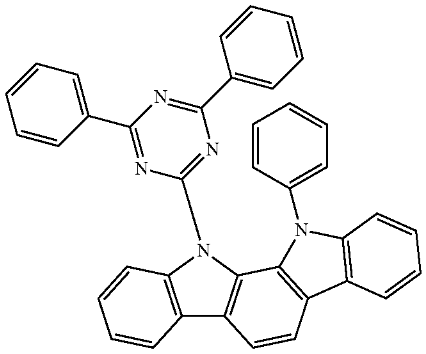
H-92
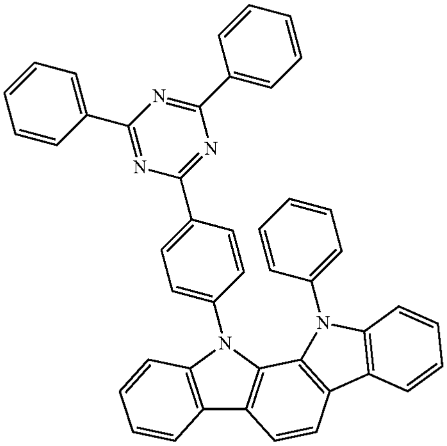
H-93
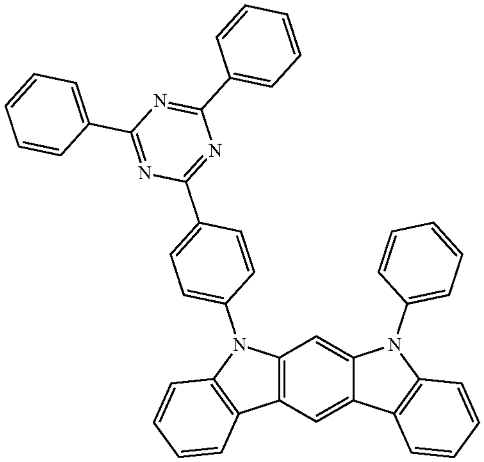

-continued
H-94
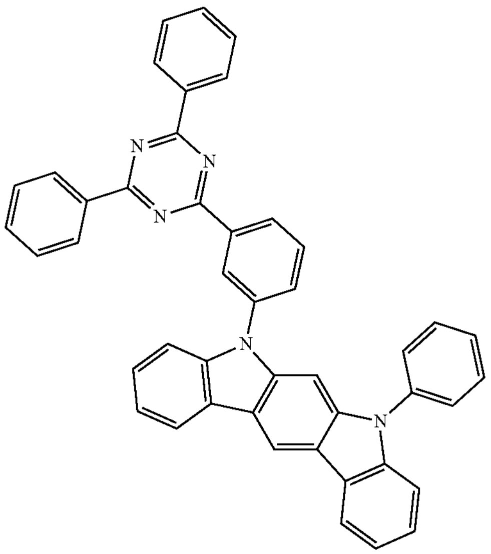
H-95
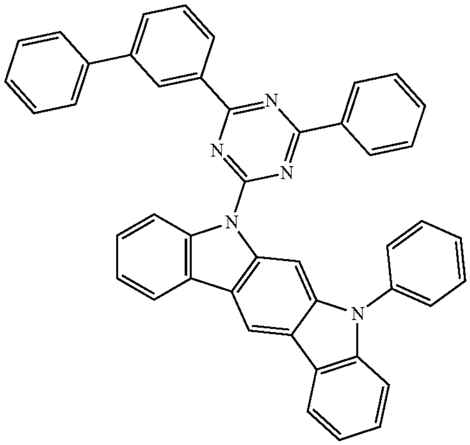
H-96
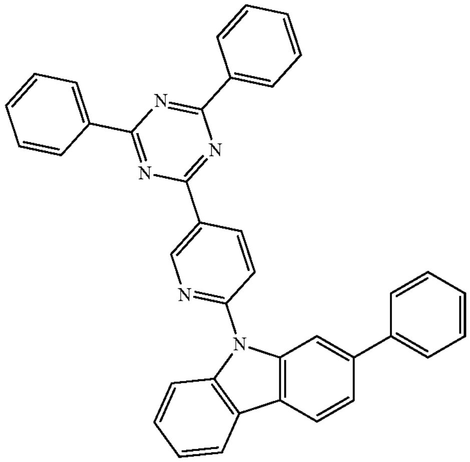
-continued
H-97
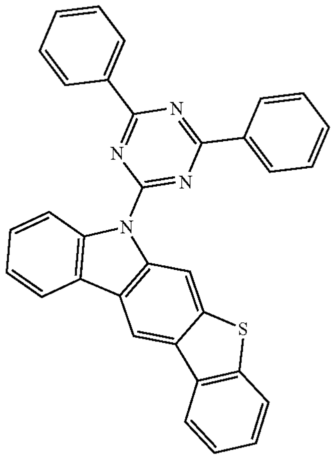
H-98
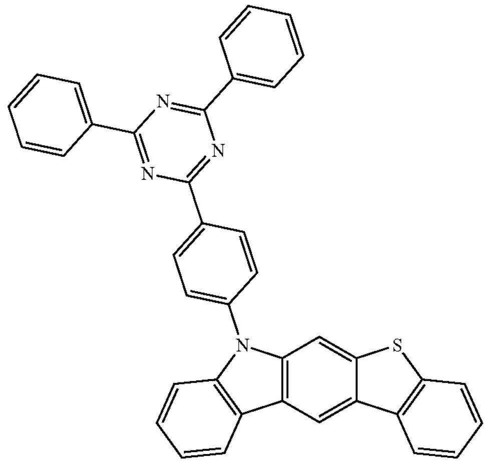
H-99
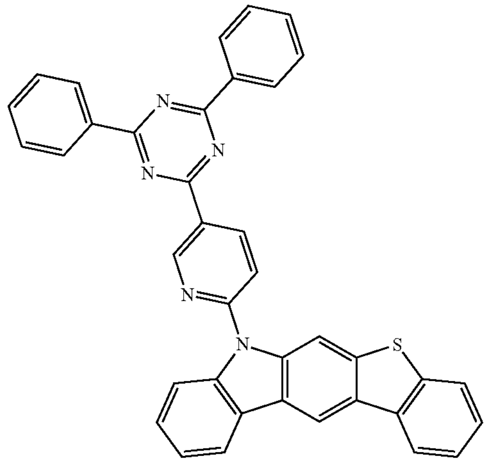

-continued
H-100
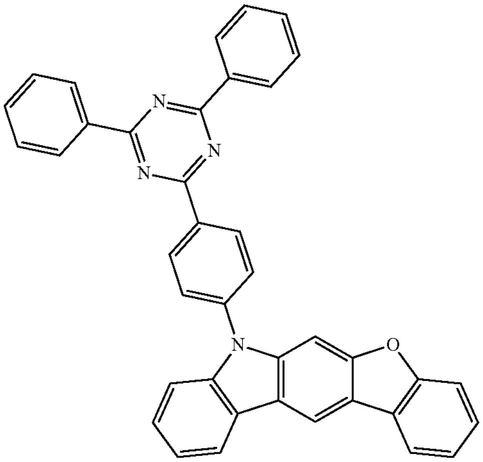
H-101
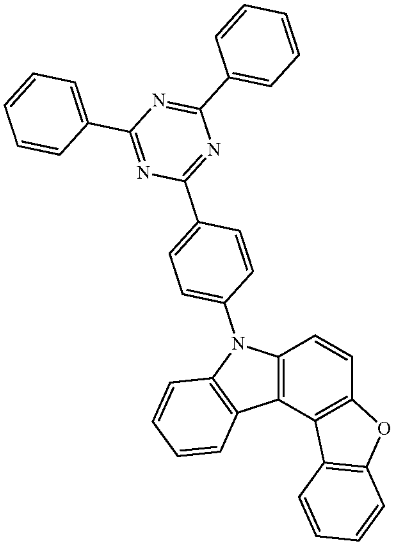
H-102
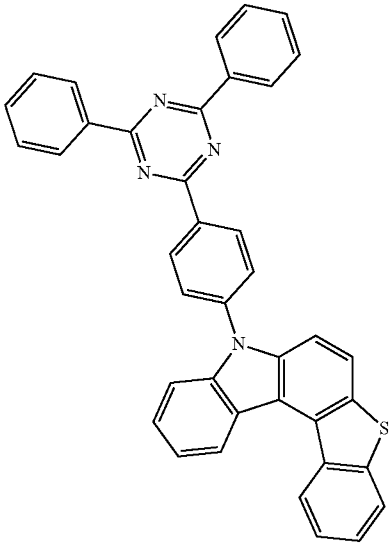
-continued
H-103
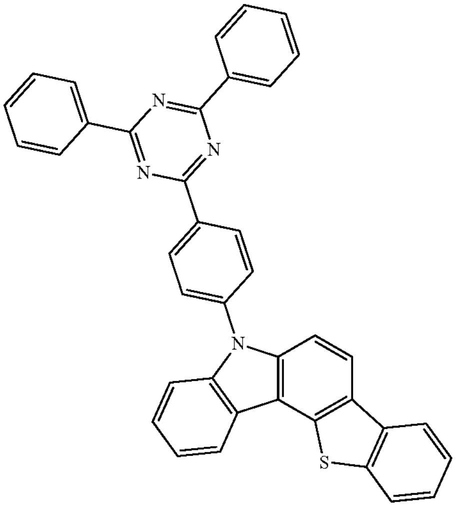
H-104
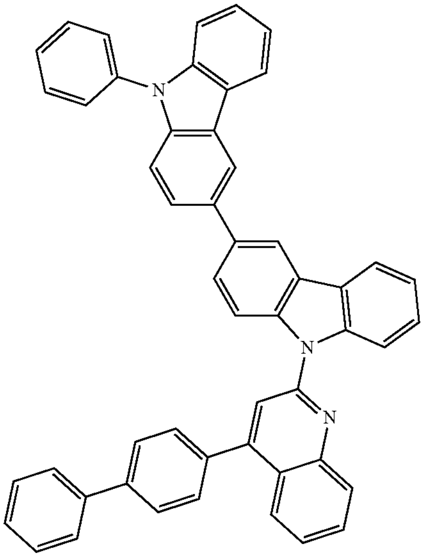
H-105
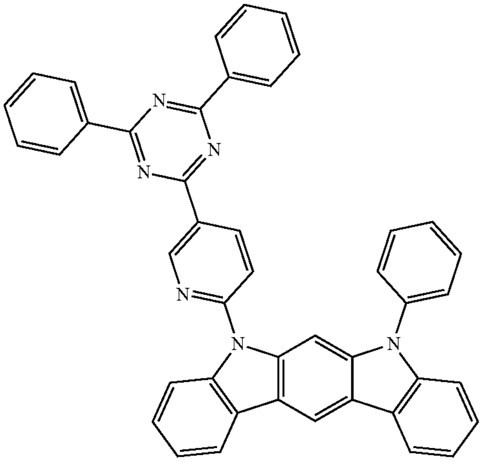

-continued
H-106
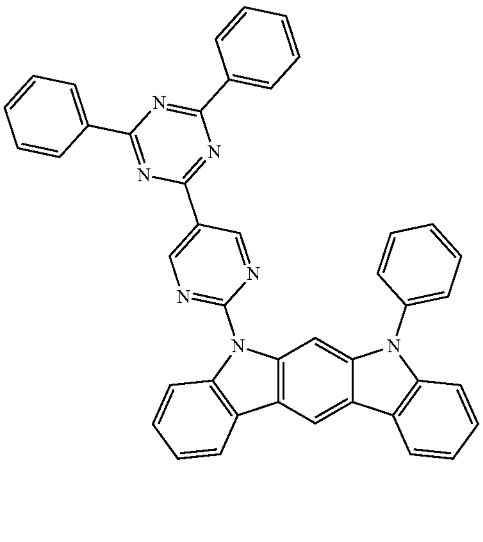
H-107
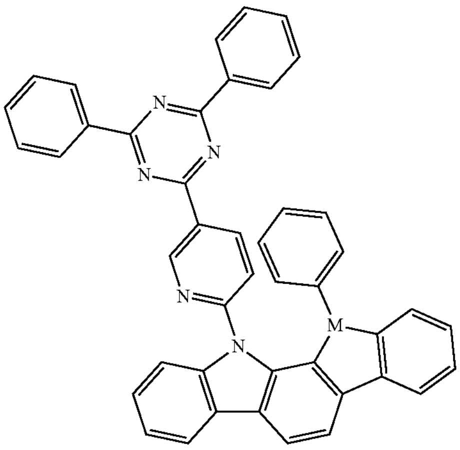
H-108
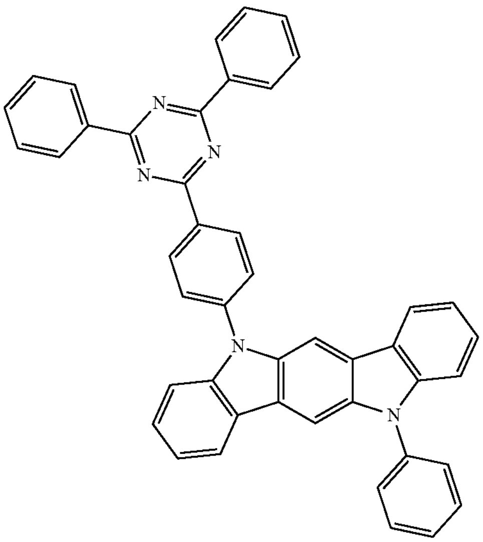
-continued
H-109
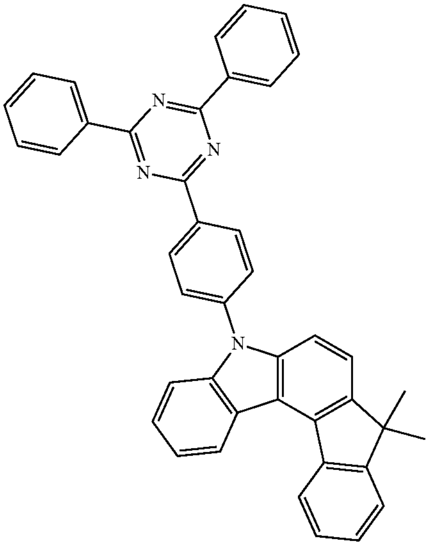
H-110
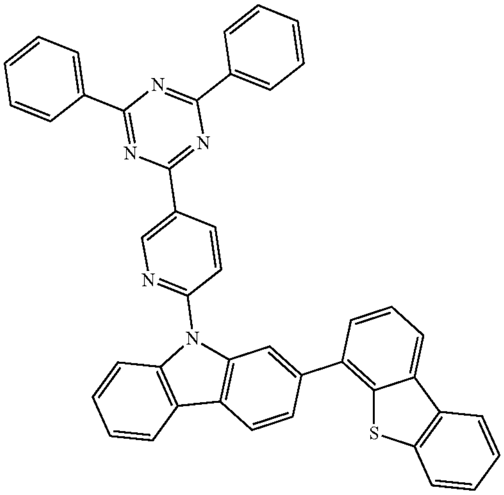
H-111
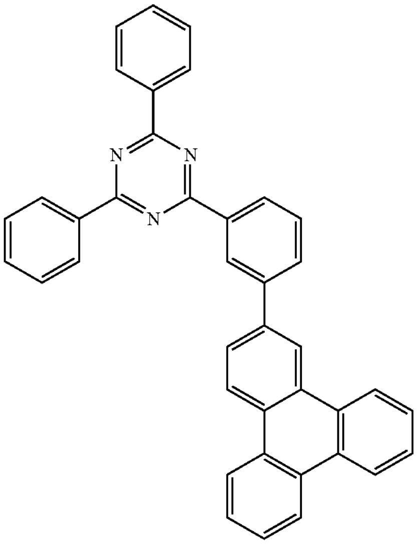

-continued
H-112
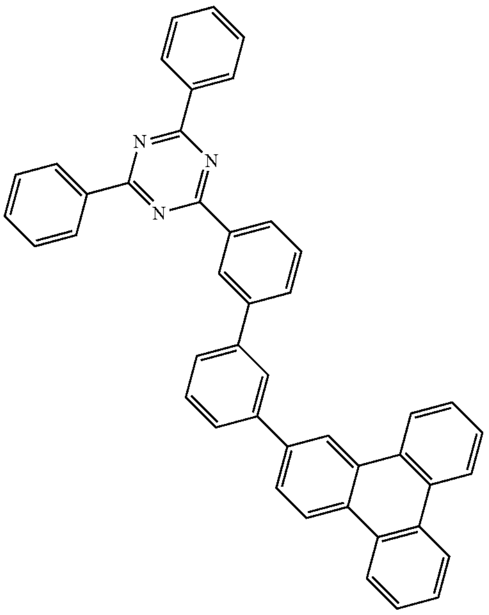
H-113
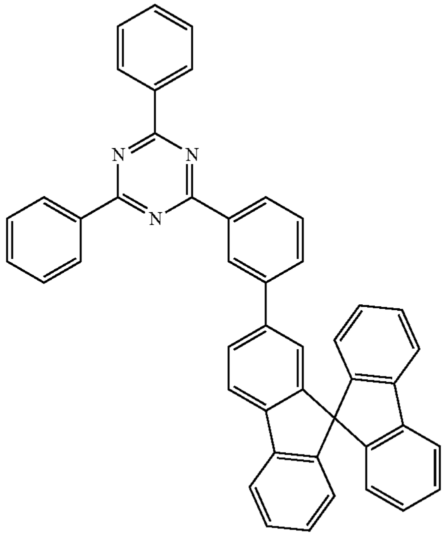
H-114
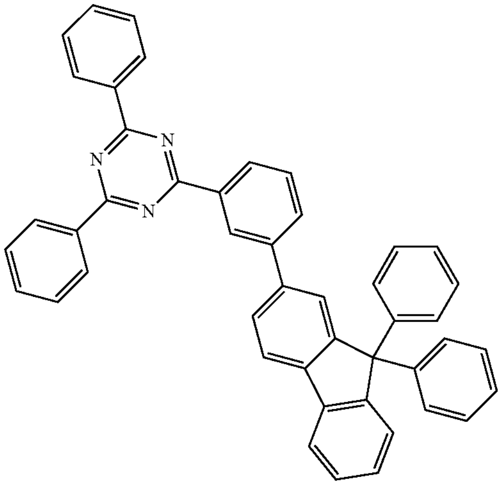
-continued
H-115
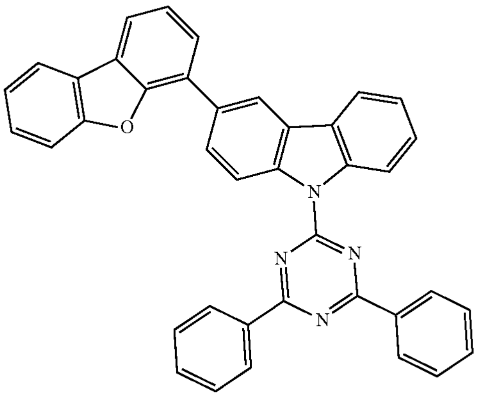
H-116
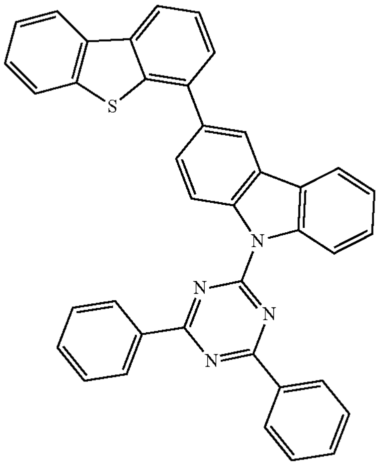
H-117
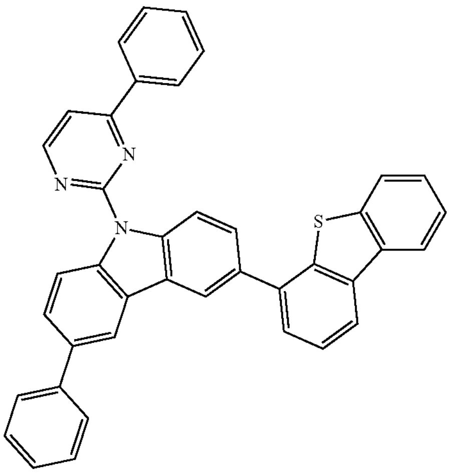

-continued
H-118
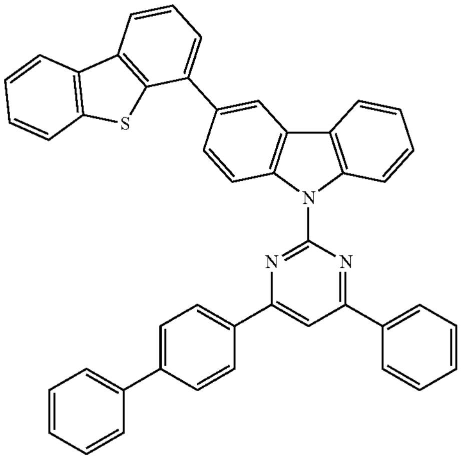
H-119
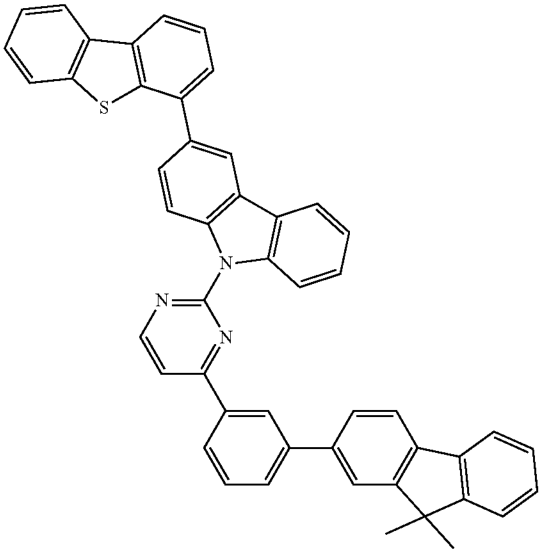
H-120
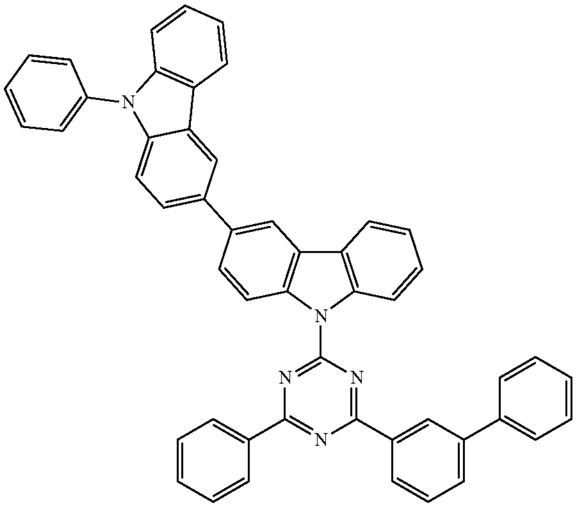
-continued
H-121
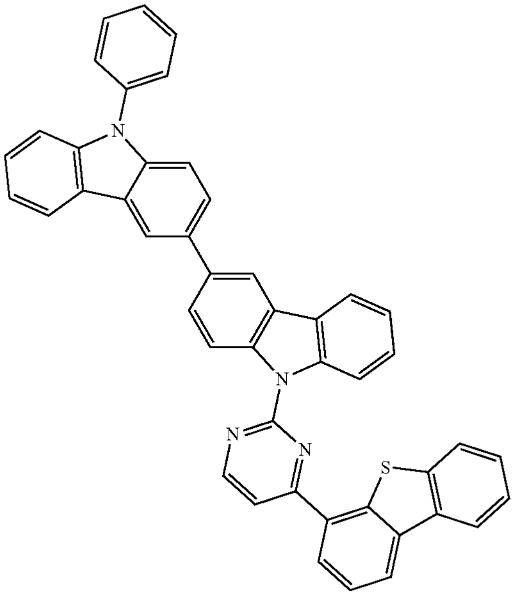
H-122
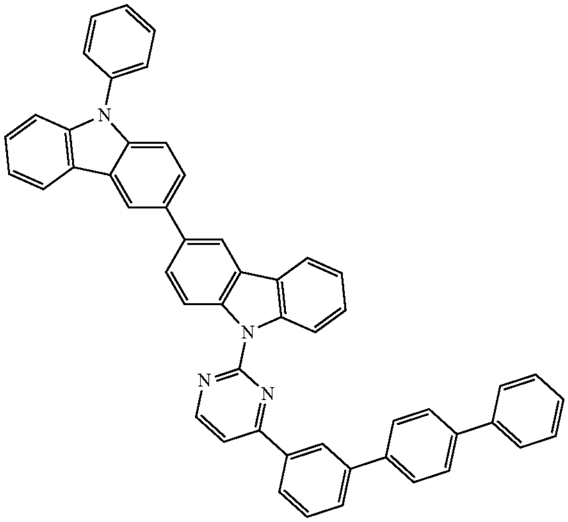

-continued
H-123
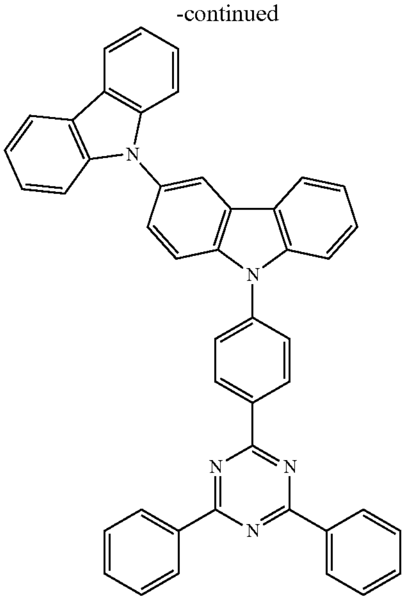
H-124
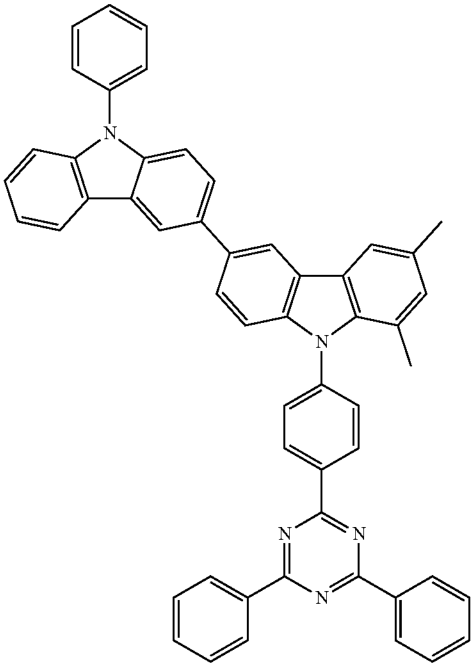
-continued
H-125
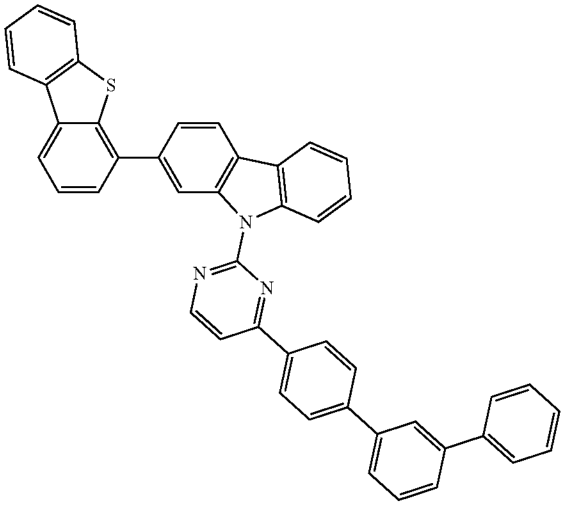
H-126
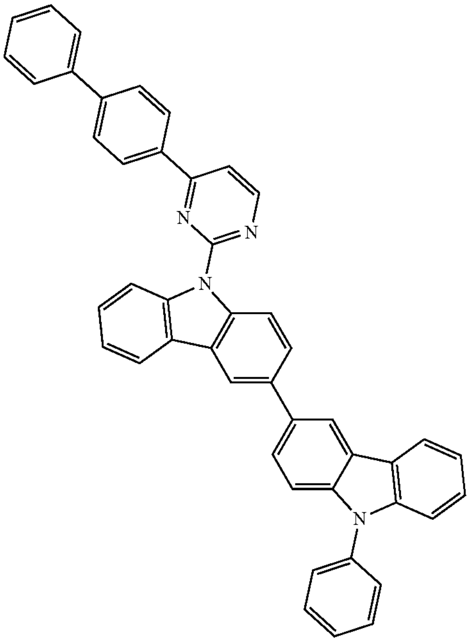

-continued
H-127
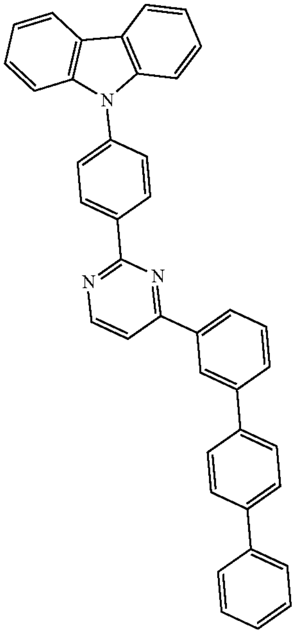
H-128
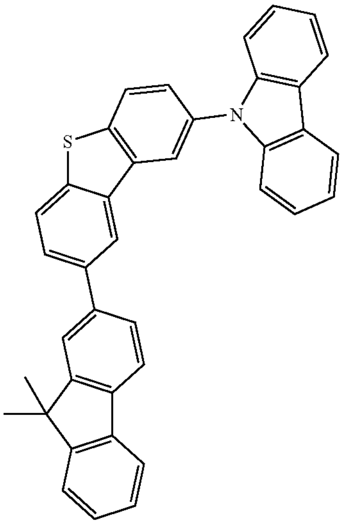
-continued
H-129
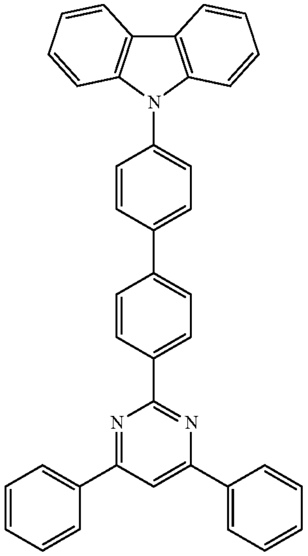
H-130
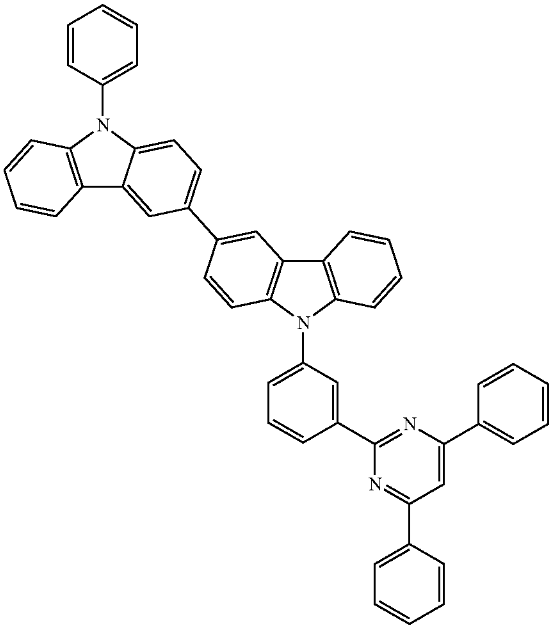

-continued
H-131
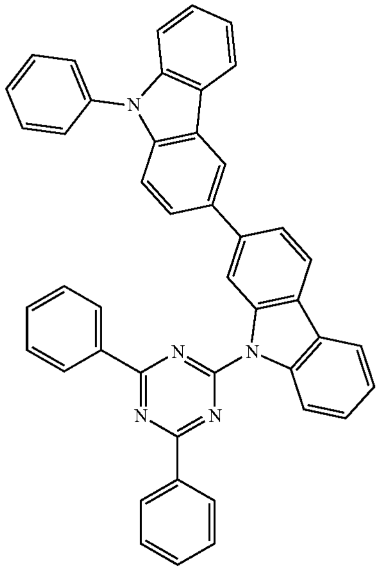
H-132
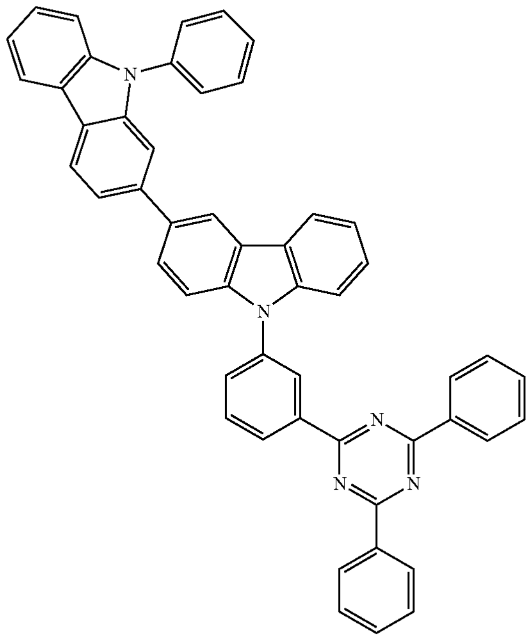
-continued
H-133
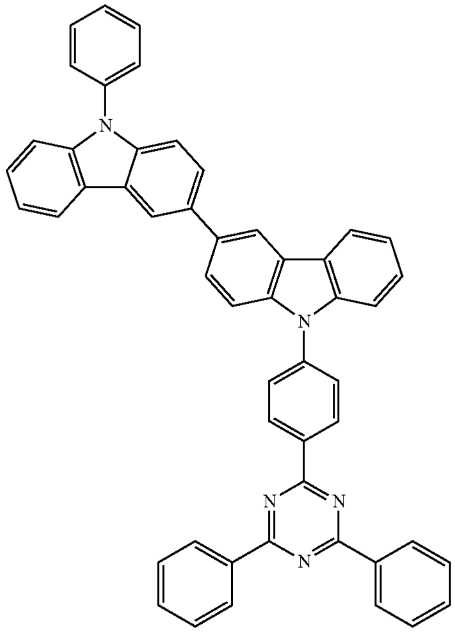
H-134
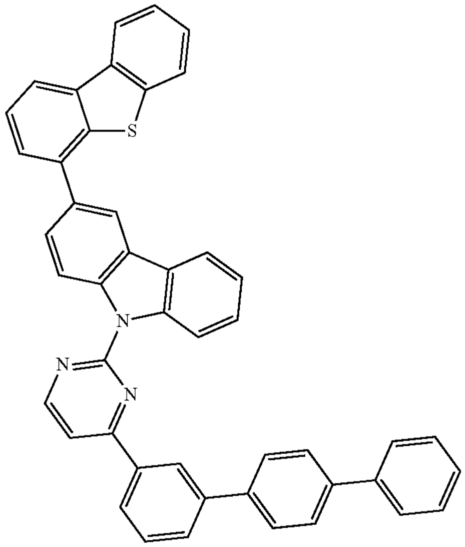

-continued
H-135
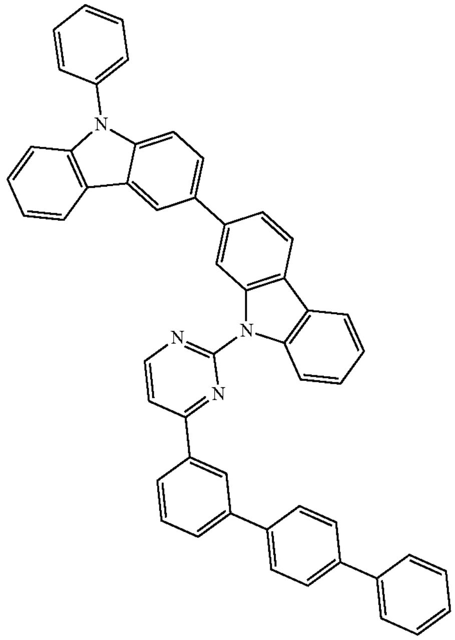
H-136
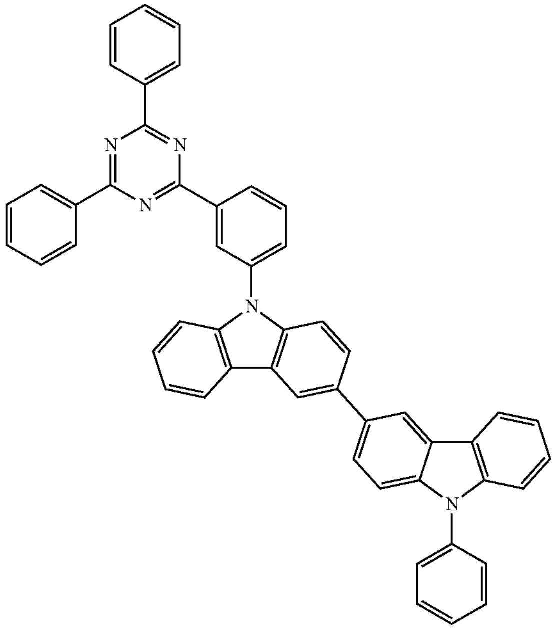
-continued
H-137
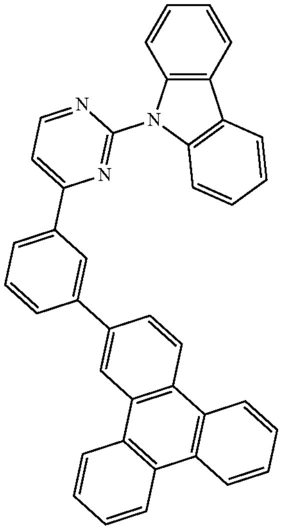
H-138
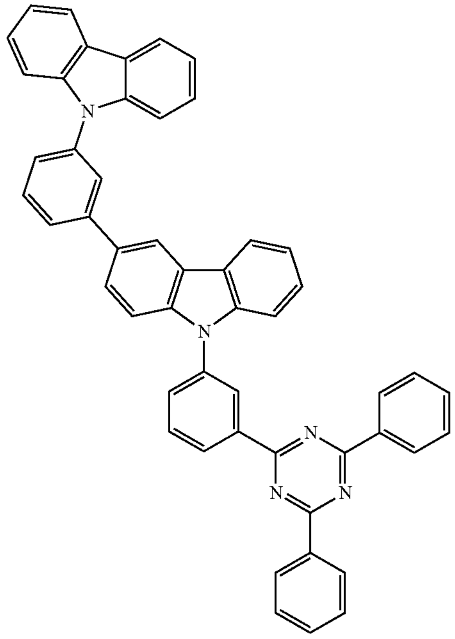

-continued
H-139
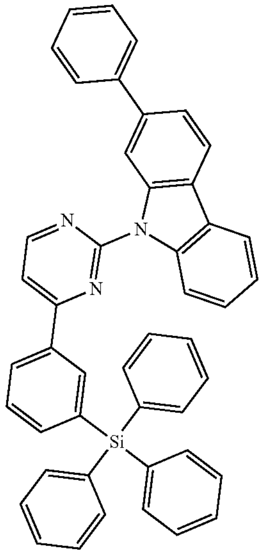
H-140
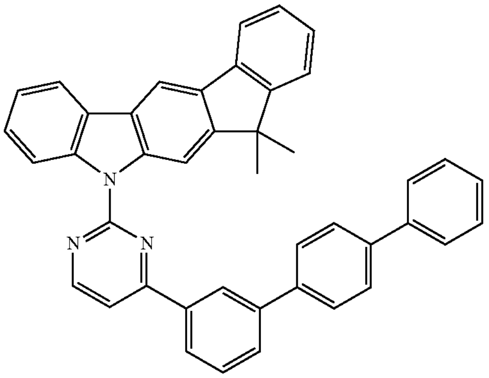
H-141
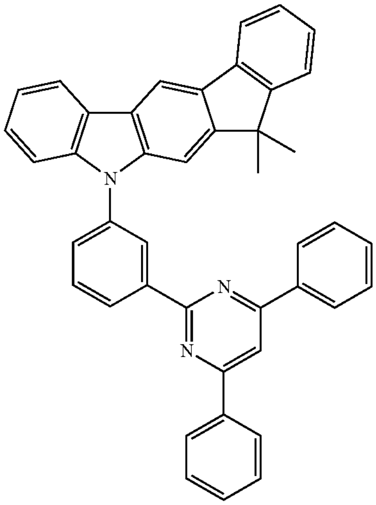
-continued
H-142
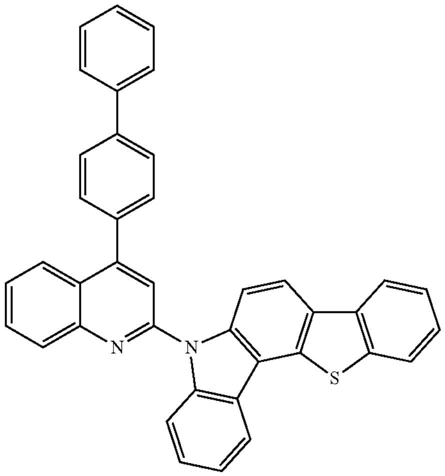
H-143
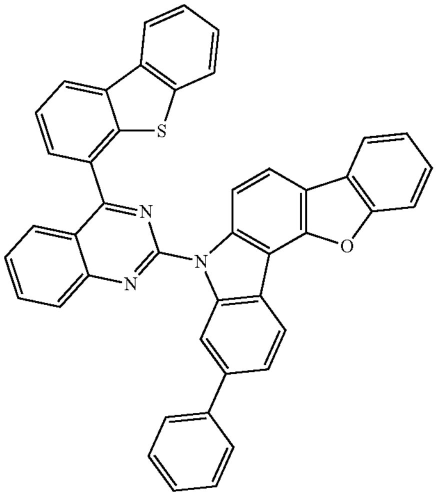
H-144
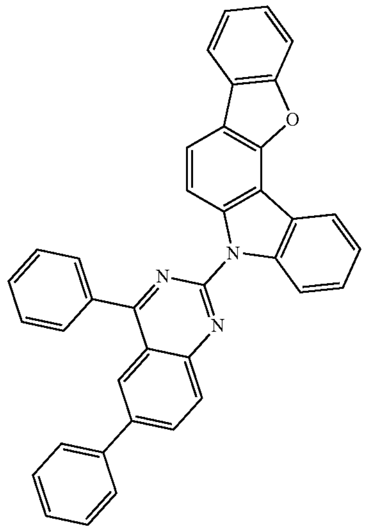

-continued
H-145
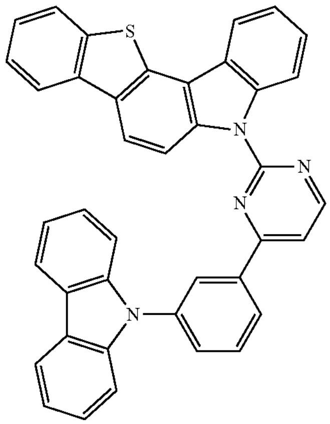
H-146
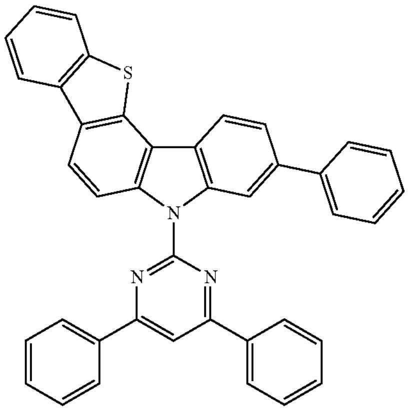
H-147
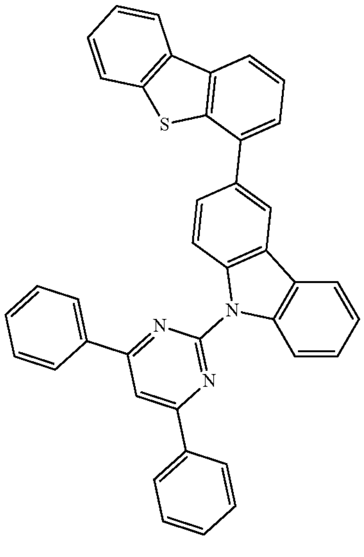
-continued
H-148
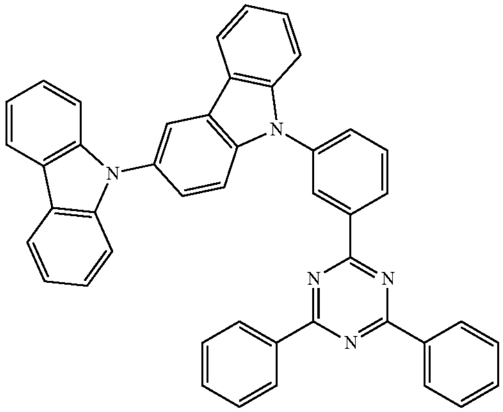
H-149
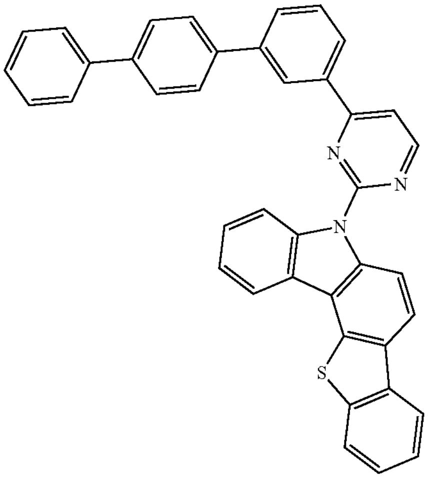
H-150
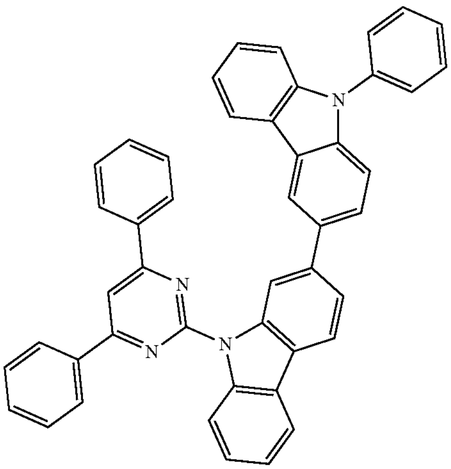

-continued
H-151
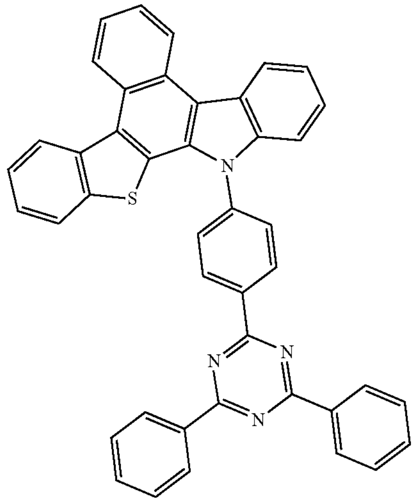
H-152
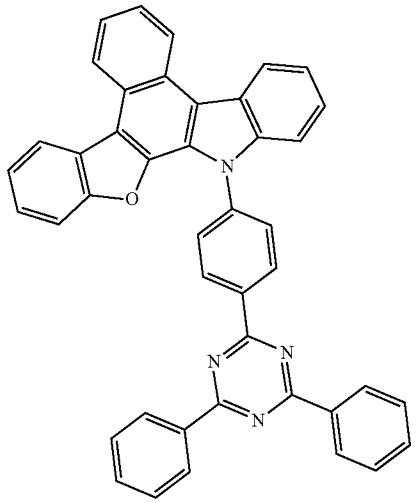
H-153
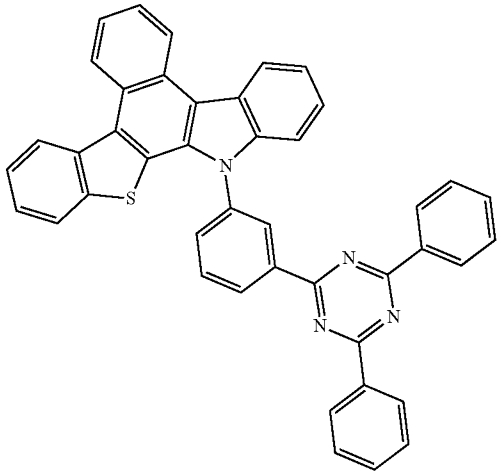
-continued
H-154
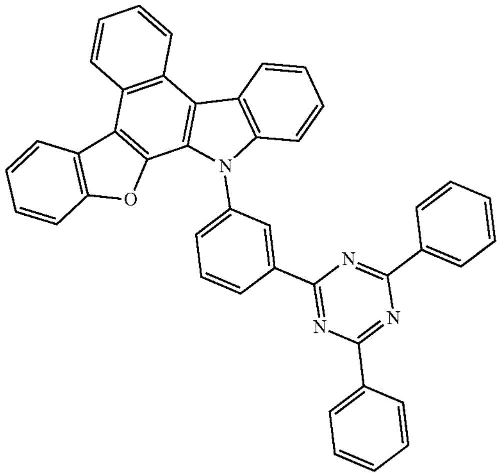
H-155
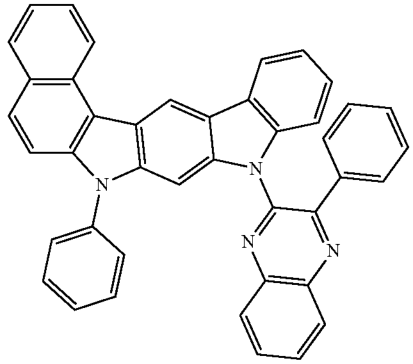
H-156
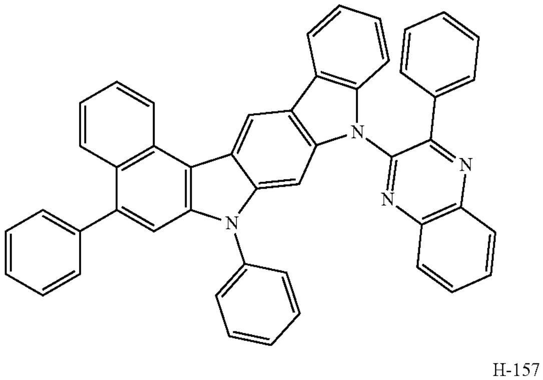
H-157
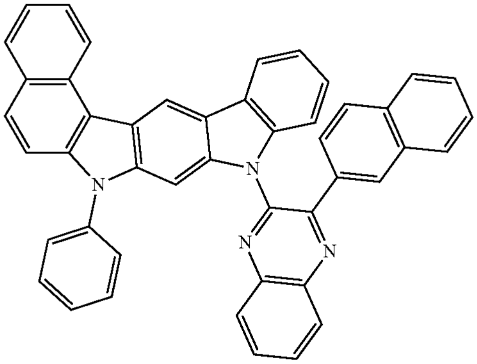

-continued
H-158
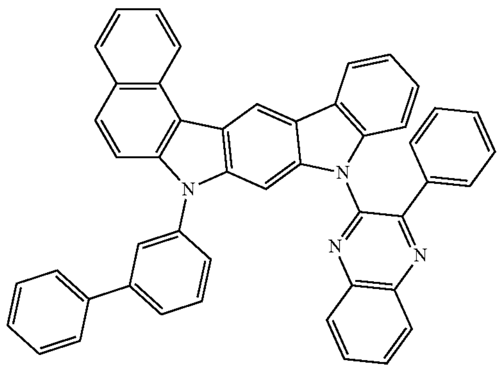
H-159
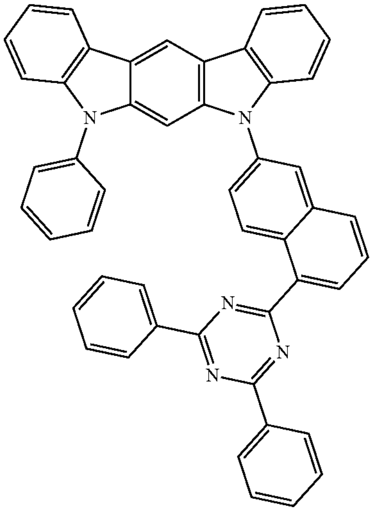
H-160
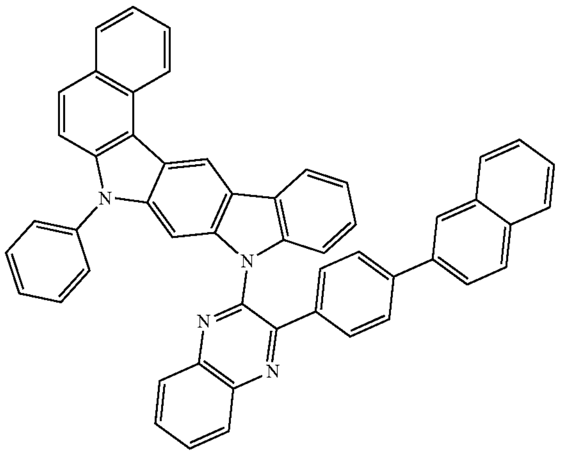
-continued
H-161
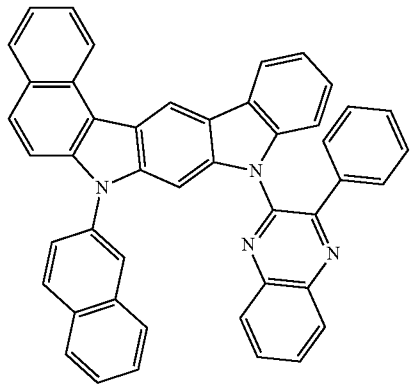
H-162
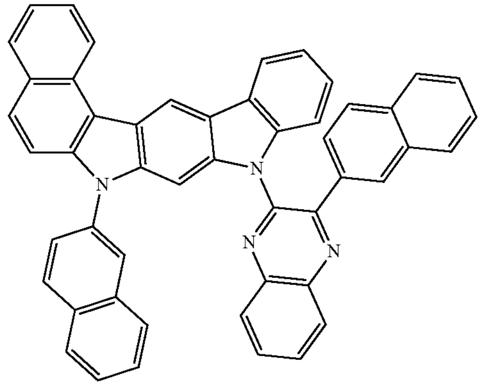
H-163
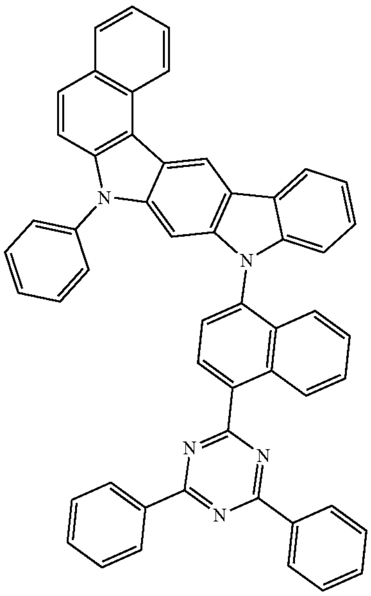

-continued
H-164
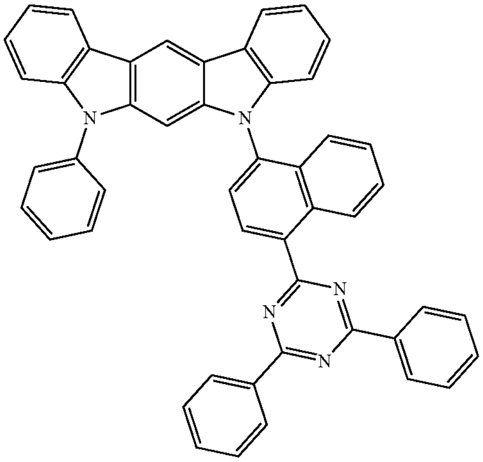
H-165
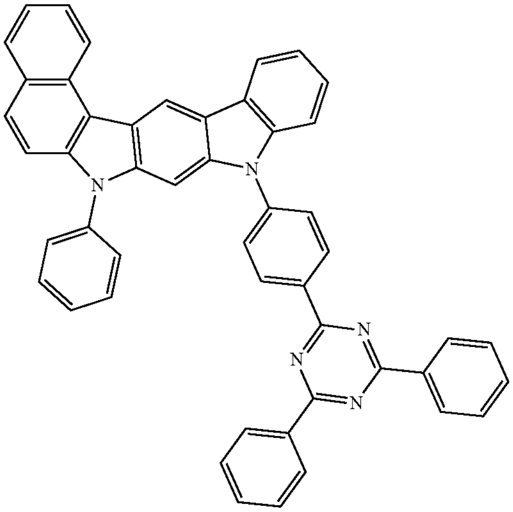
H-166
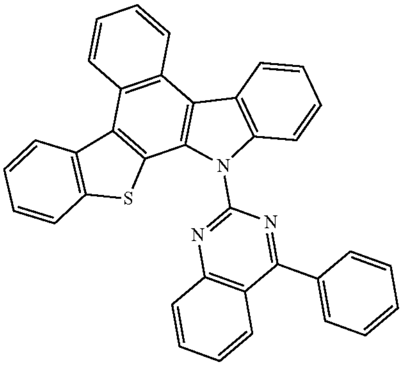
-continued
H-167
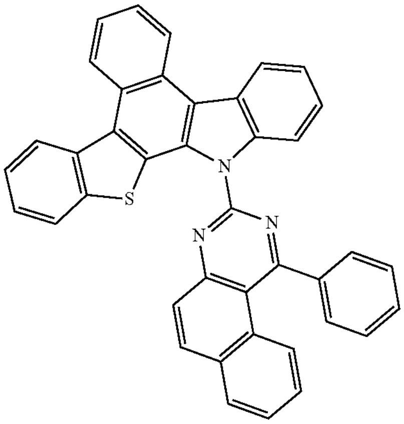
H-168
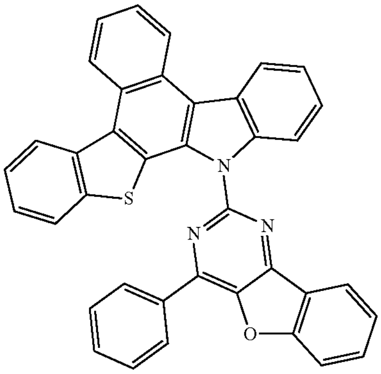
H-169
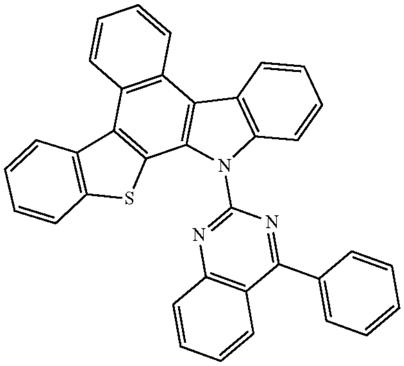
H-170
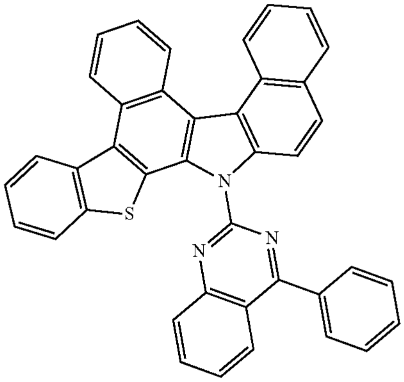

-continued
H-171
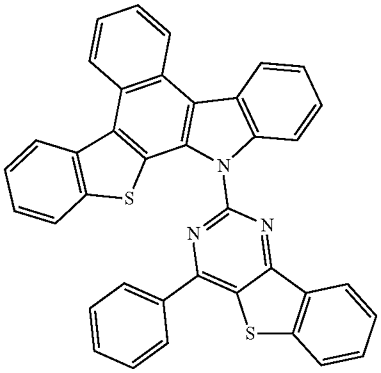
H-172
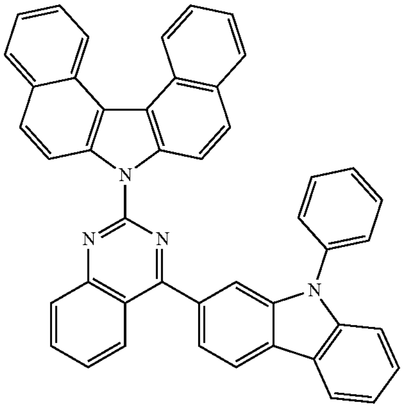
H-173
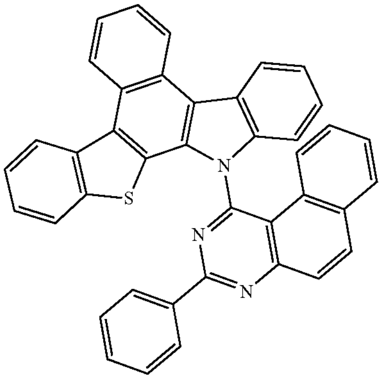
H-174
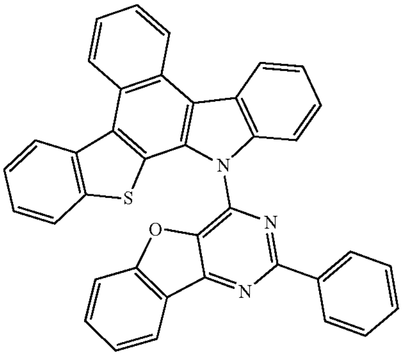
-continued
H-175
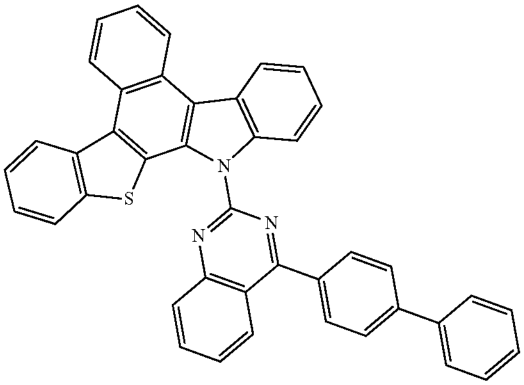
H-176
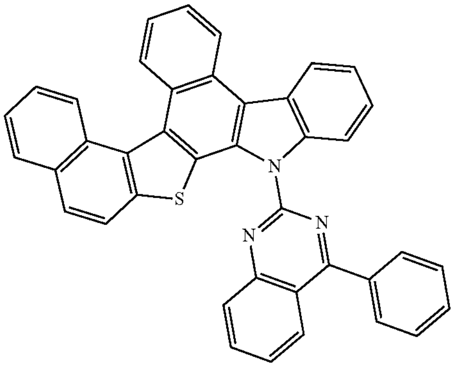
H-177
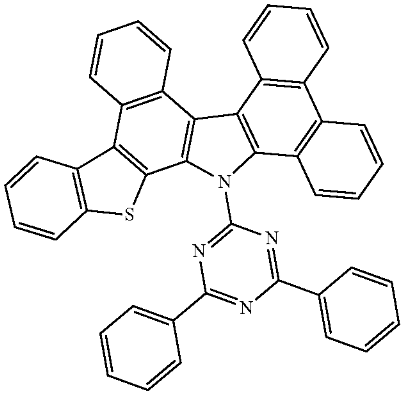
H-178
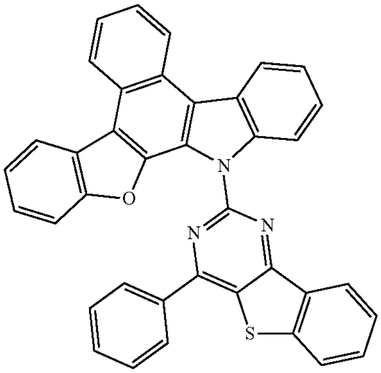

-continued
H-179
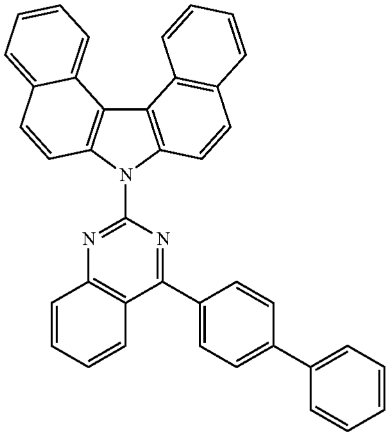
H-180
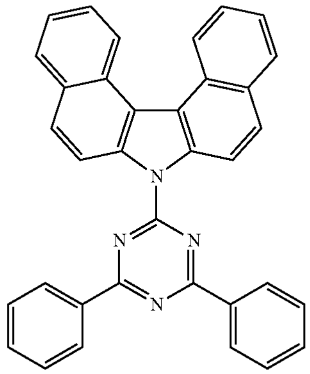
H-181
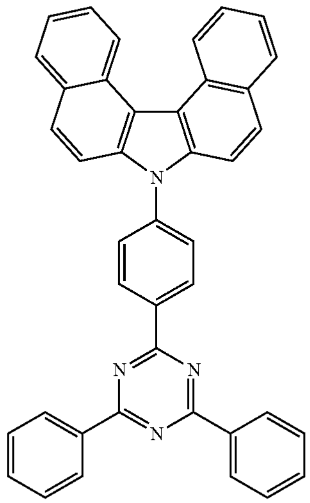
-continued
H-182
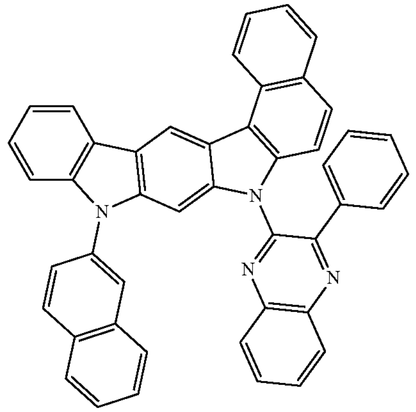
H-183
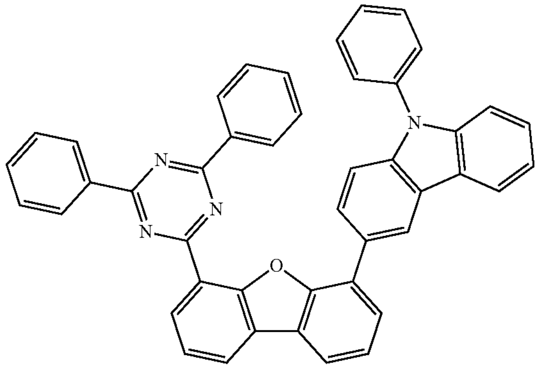
H-184
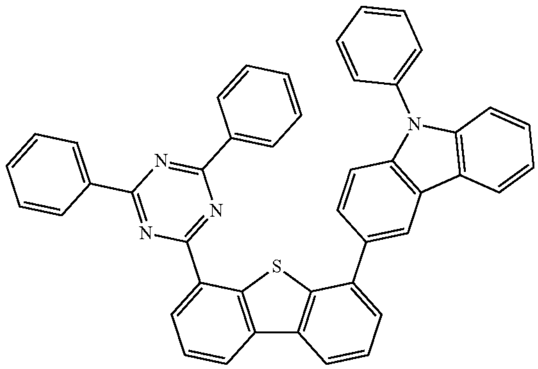

-continued
H-185
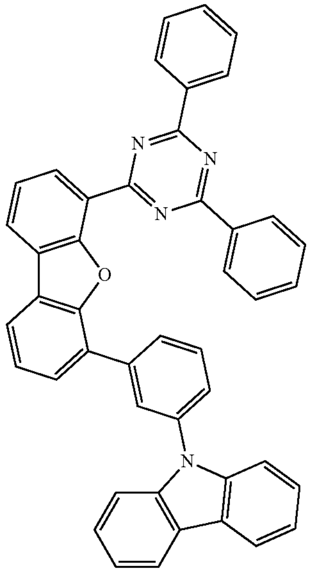
H-186
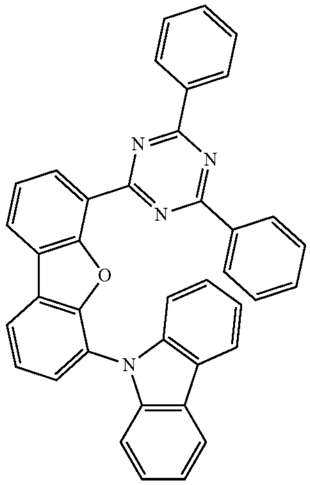
-continued
H-187
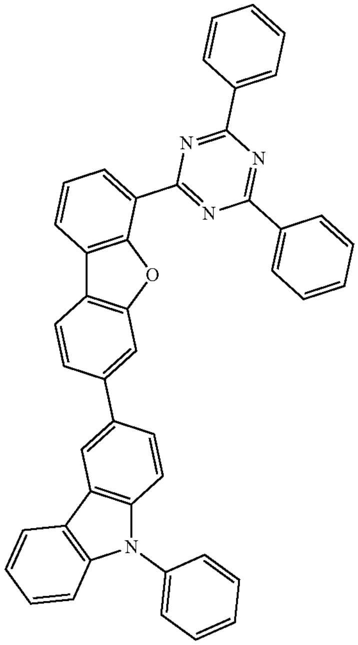
H-188
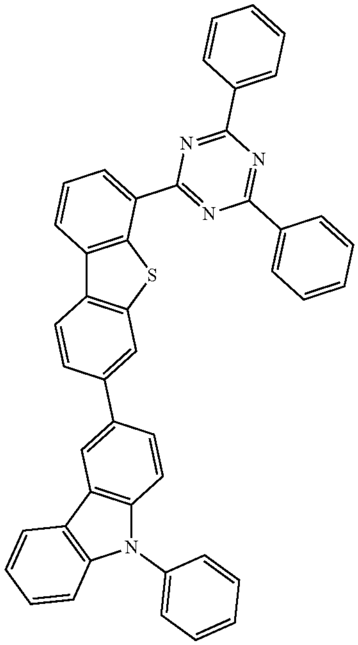

-continued
H-189
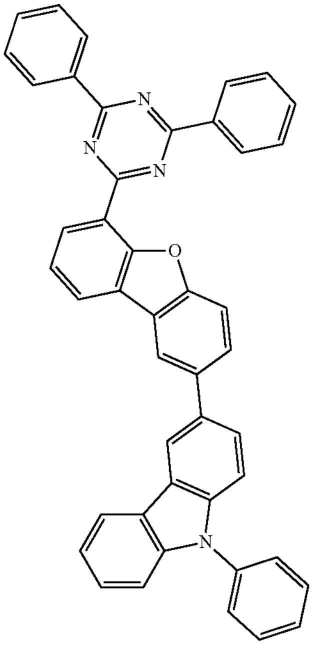
H-190
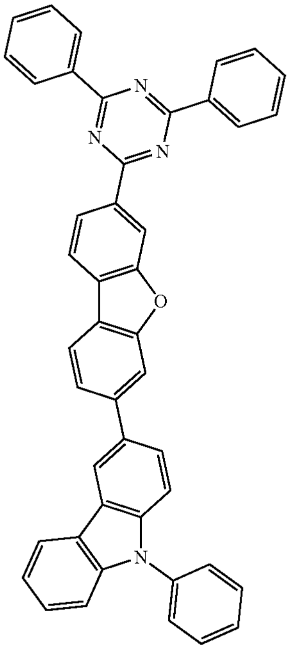
-continued
H-191
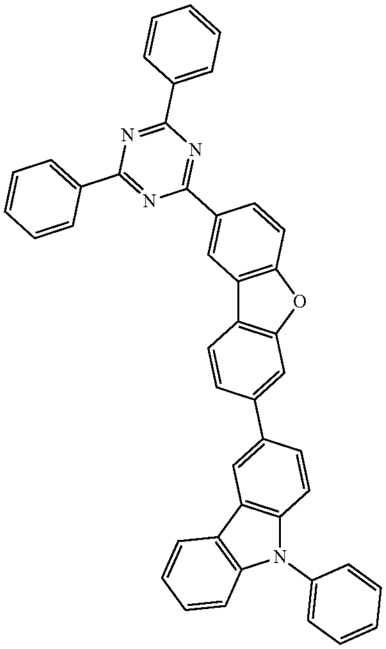
H-192
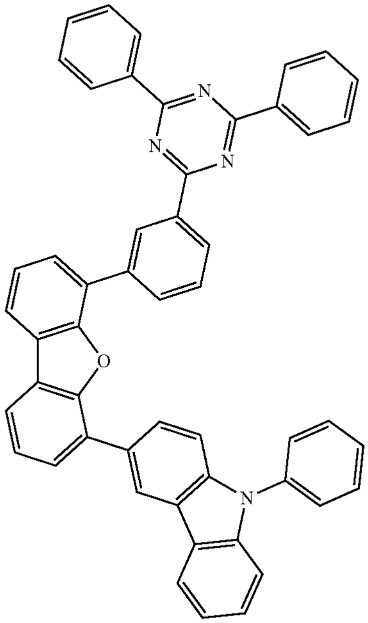

-continued
H-193
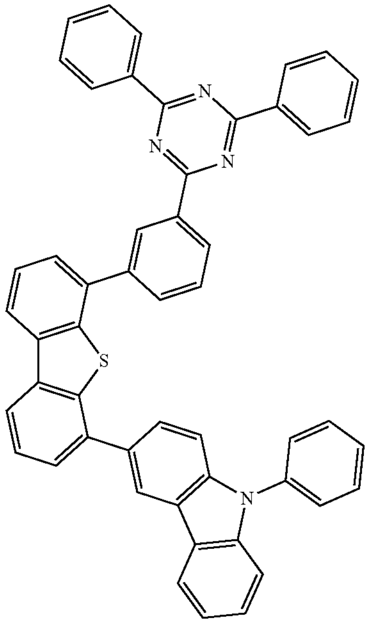
H-194
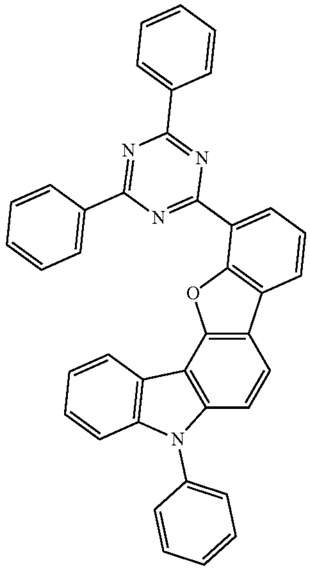
-continued
H-195
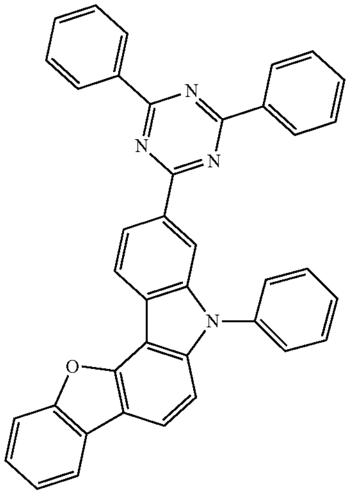
H-196
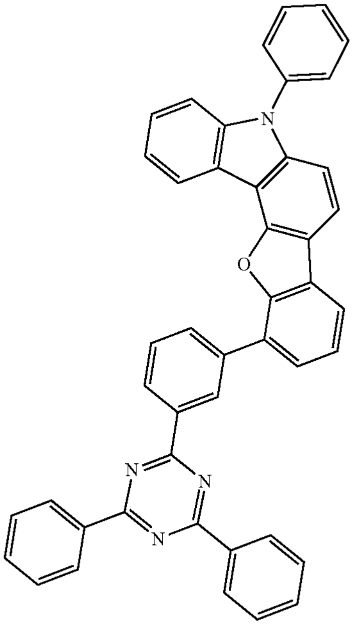

-continued
H-197
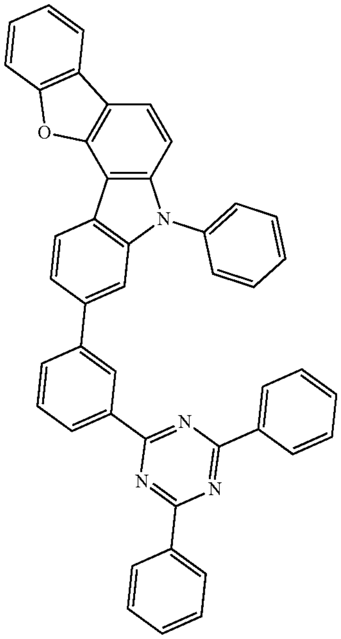
H-198
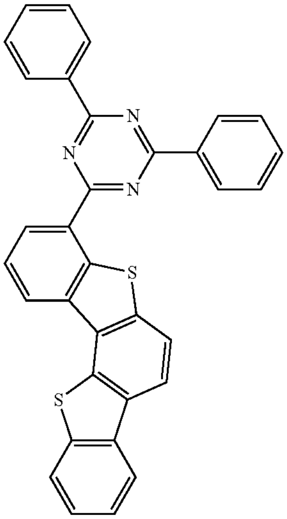
-continued
H-199
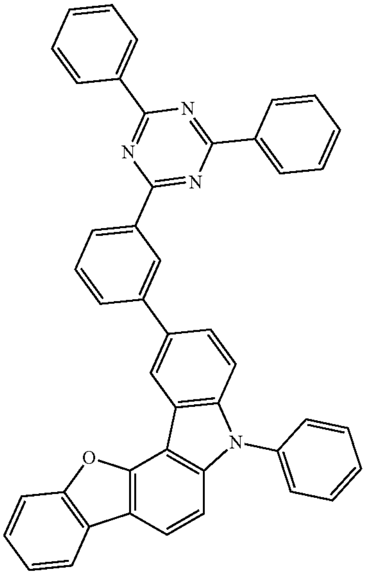
H-200
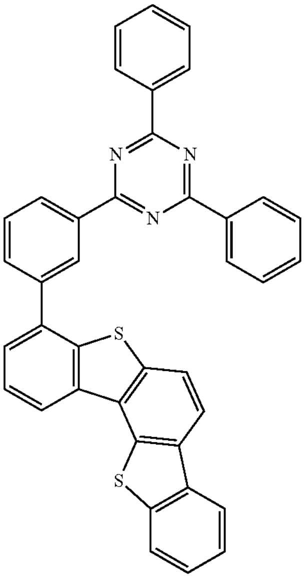

-continued
H-201
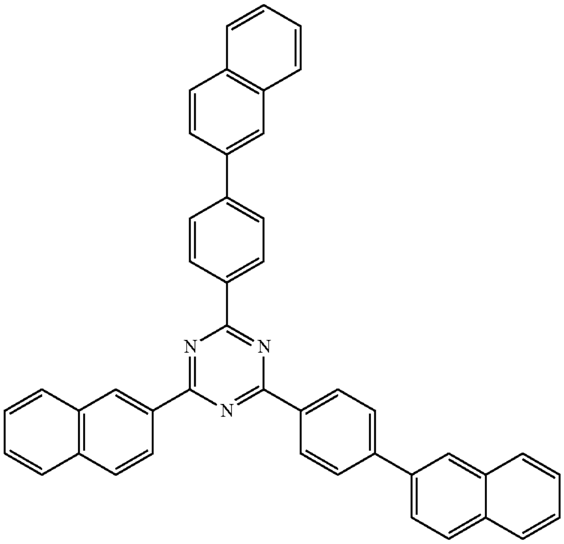
H-202
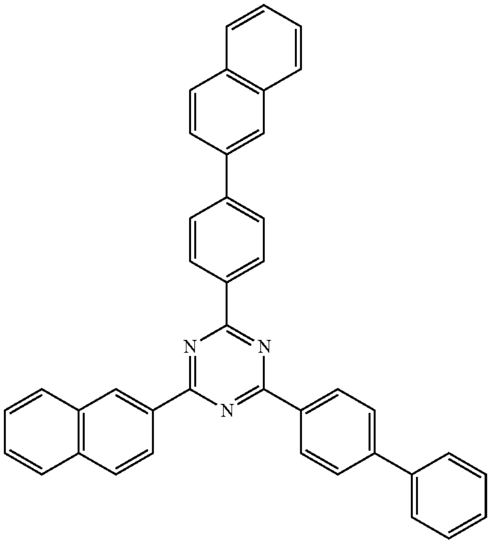
H-203
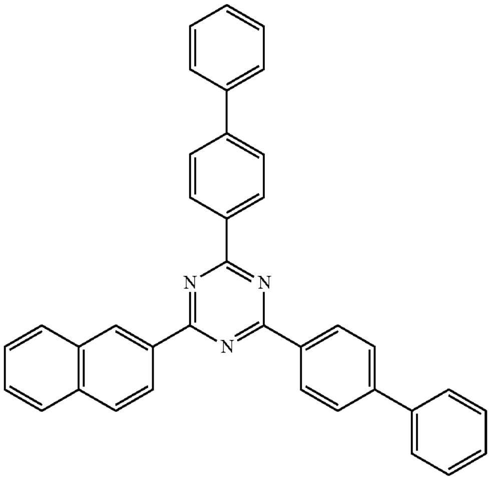
-continued
H-204
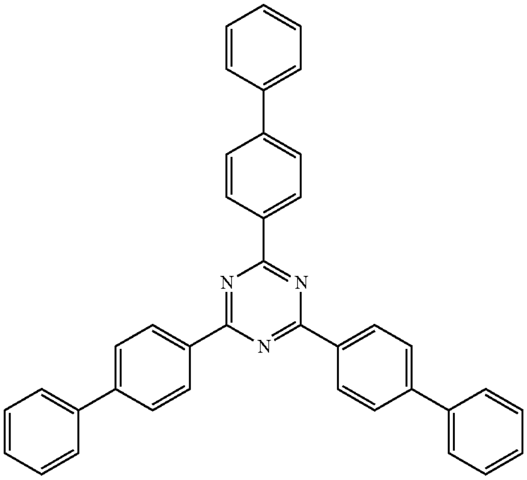
H-205
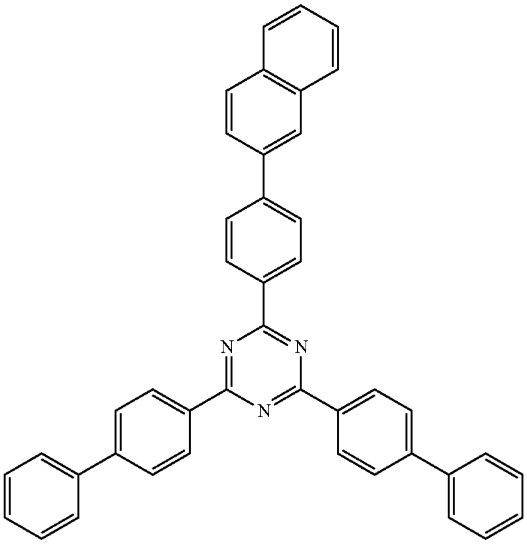
H-206
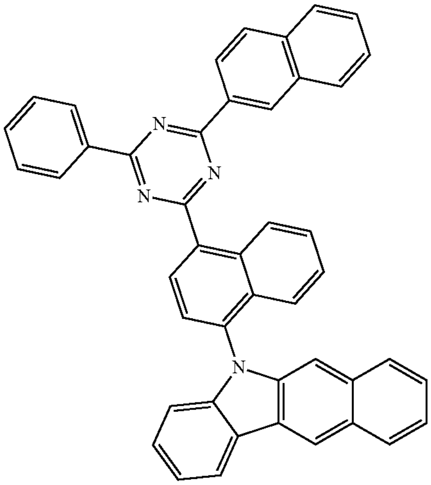

-continued

H-207

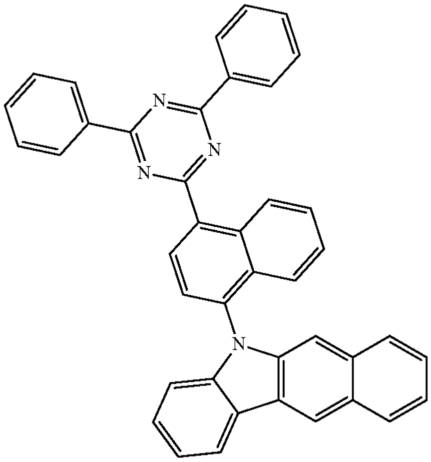

H-208

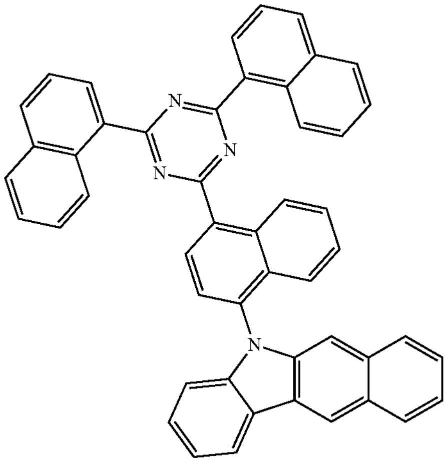

H-209

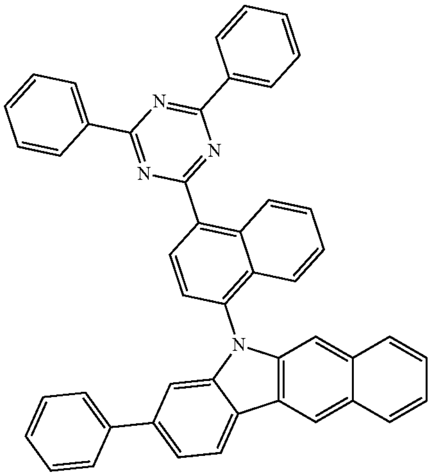

-continued

H-210

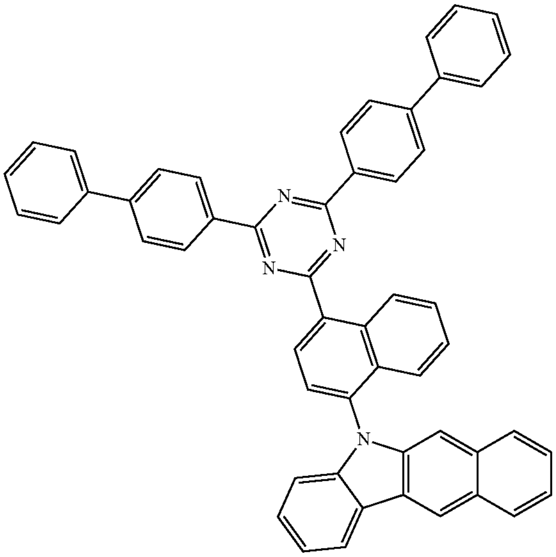

Wherein, TPS represents a triphenylsilyl group.

The dopant comprised in the organic electroluminescent device of the present disclosure is preferably at least one phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Jr), osmium (Os), copper (Cu), and platinum (Pt), and even more preferably ortho-metallated iridium complex compounds.

The dopant comprised in the organic electroluminescent device of the present disclosure may comprise the compound represented by the following formula 101, but is not limited thereto.

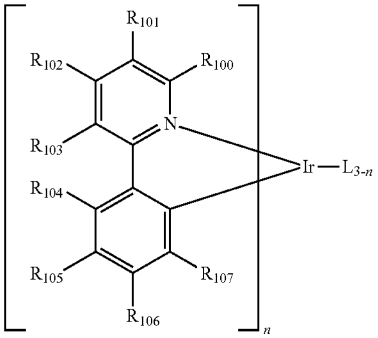

(101)

In formula 101, $L_1$ is selected from the following structures 1 and 2:

[Structure 1]

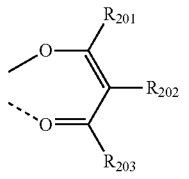

[Structure 2]

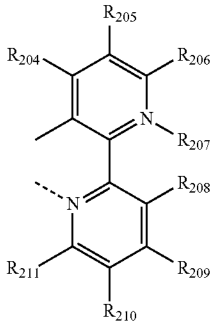

$R_{100}$ to $R_{103}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to adjacent $R_{100}$ to $R_{103}$, to form a substituted or unsubstituted fused ring, e.g., a substituted or unsubstituted, quinoline, benzofuropyridine, benzothienopyridine, indenopyridine, benzofuroquinoline, benzothienoquinoline or indenoquinoline ring;

$R_{104}$ to $R_{107}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to adjacent $R_{104}$ to $R_{107}$ to form a substituted or unsubstituted fused ring, e.g., a substituted or unsubstituted, naphthyl, fluorene, dibenzothiophene, dibenzofuran, indenopyridine, benzofuropyridine or benzothienopyridine ring;

$R_{201}$ to $R_{211}$, each independently, represent hydrogen, deuterium, a halogen, a (C1-C30)alkyl unsubstituted or substituted with deuterium or a halogen, a substituted or unsubstituted (C3-C30)cycloalkyl, or a substituted or unsubstituted (C6-C30)aryl; or may be linked to adjacent $R_{201}$ to $R_{211}$ to form a substituted or unsubstituted fused ring; and n represents an integer of 1 to 3.

The specific examples of the dopant compound are as follows, but are not limited thereto.

D-1

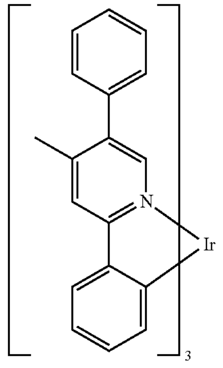

D-2

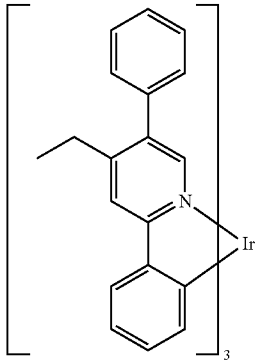

D-3

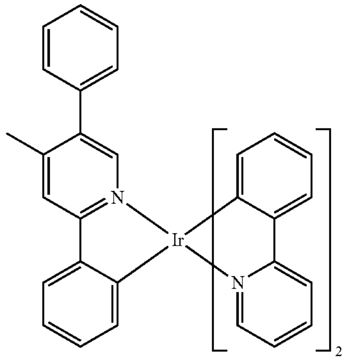

D-4

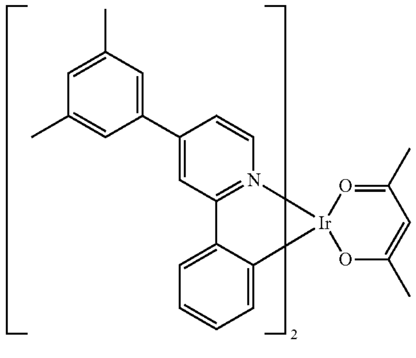

-continued
D-5
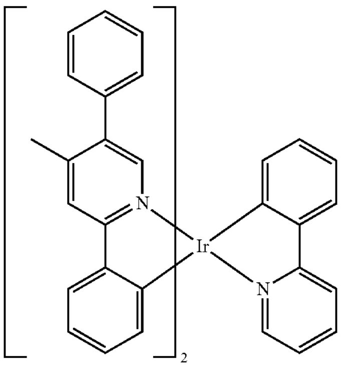
D-6
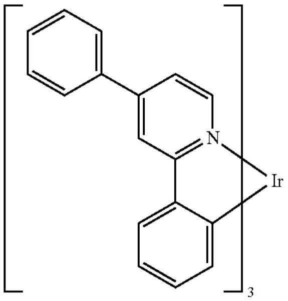
D-7
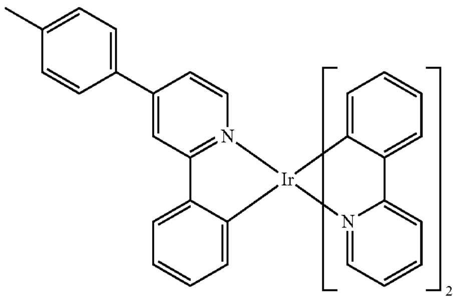
D-8
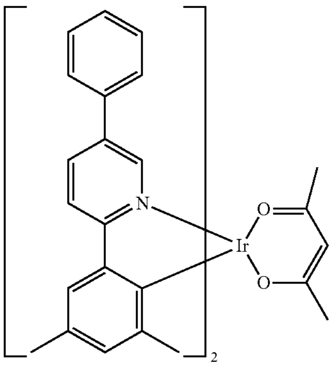
-continued
D-9
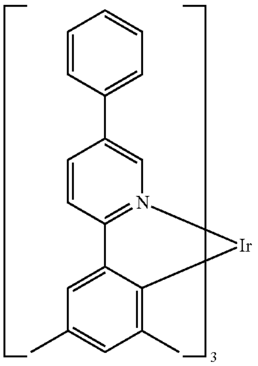
D-10
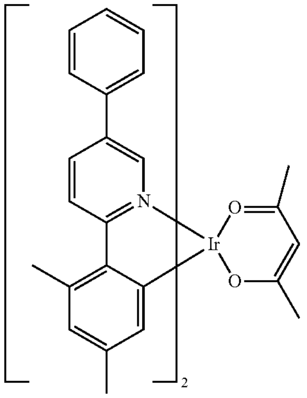
D-11
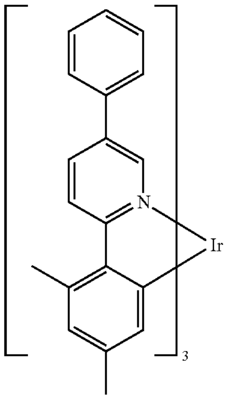
D-12
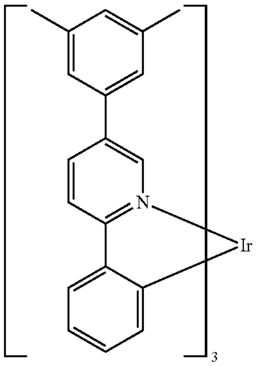

-continued
D-13
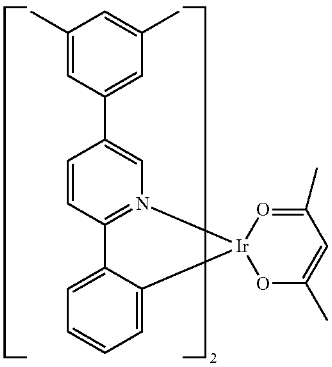
D-14
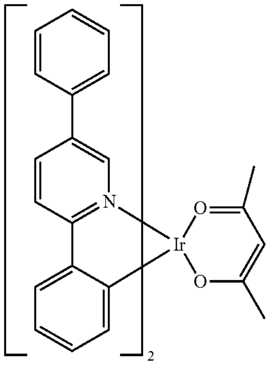
D-15
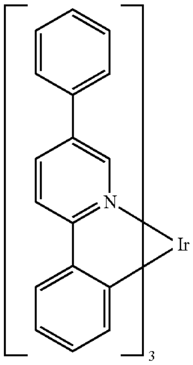
D-16
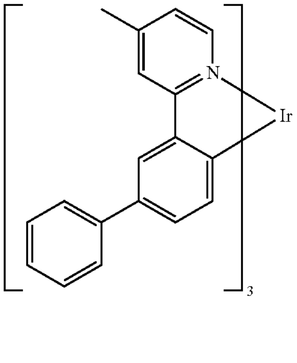
-continued
D-17
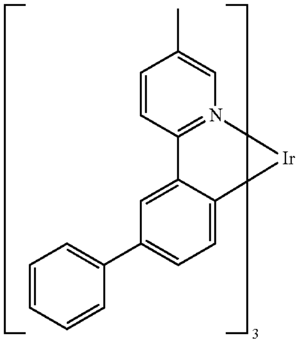
D-18
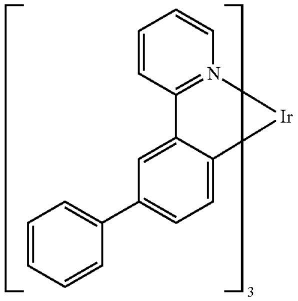
D-19
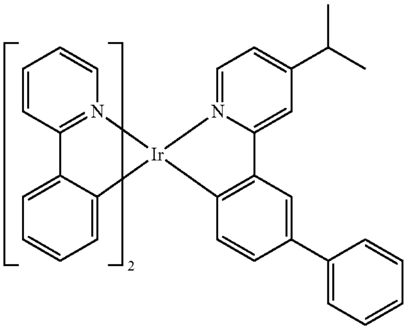
D-20
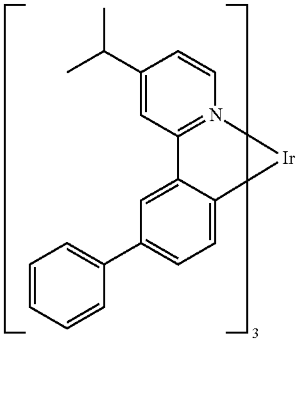

-continued
D-21
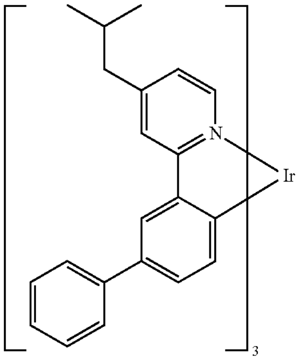
D-22
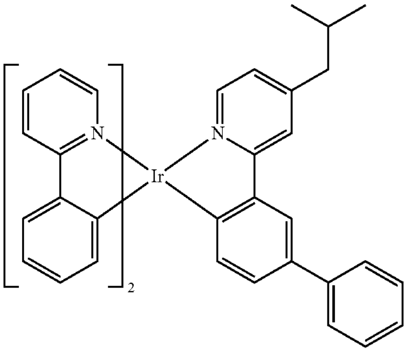
D-23
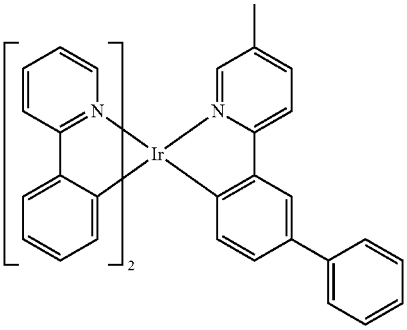
D-24
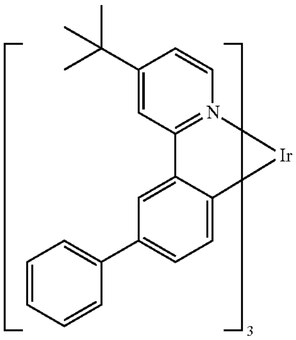
-continued
D-25
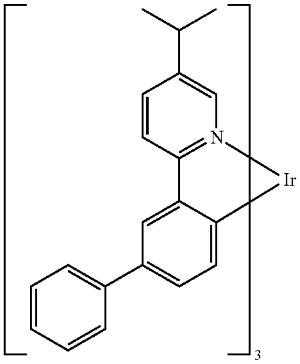
D-26
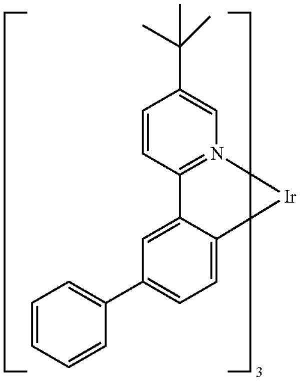
D-27
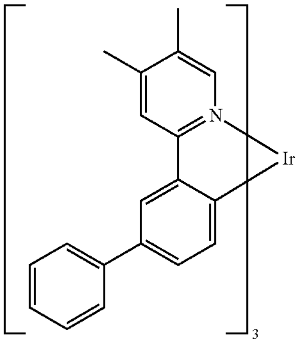
D-28
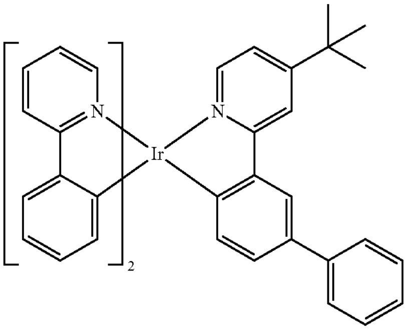

-continued
D-29
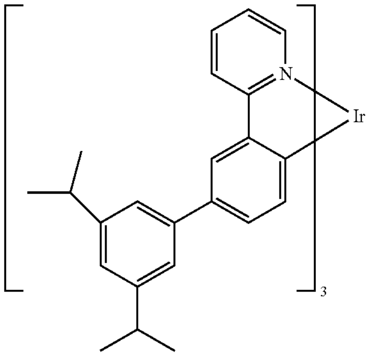
D-30
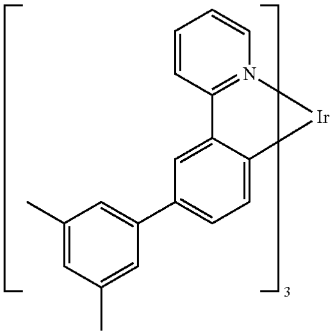
D-31
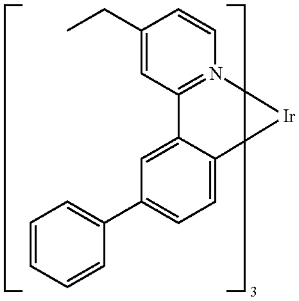
D-32
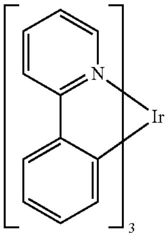
D-33
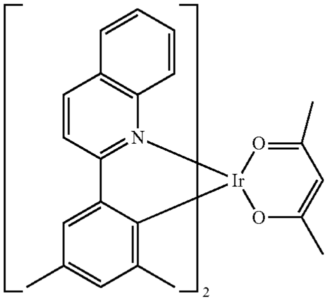
-continued
D-34
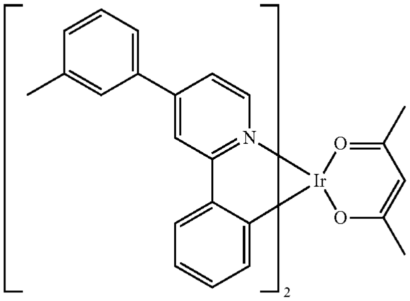
D-35
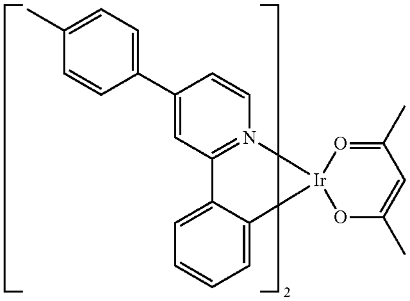
D-36
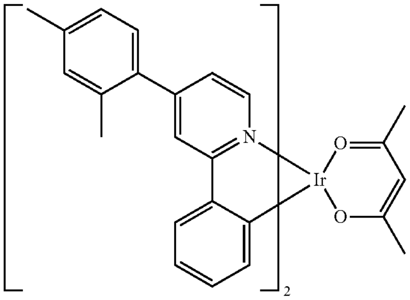
D-37
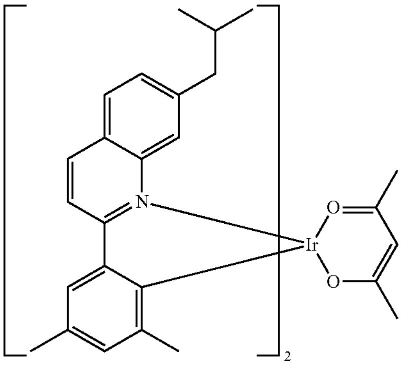
D-38
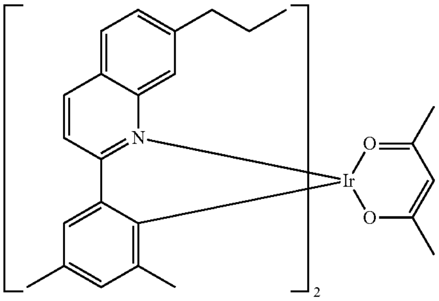

-continued
D-39
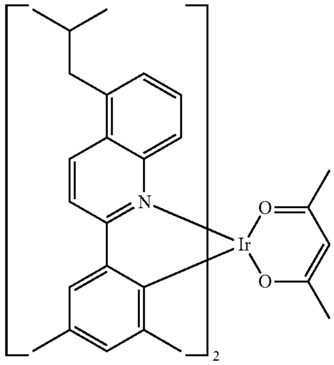
D-40
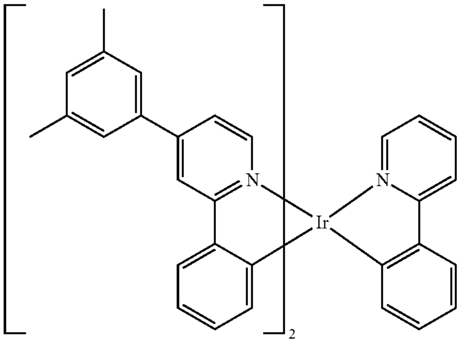
D-41
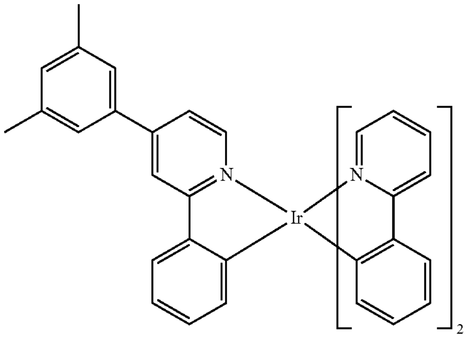
D-42
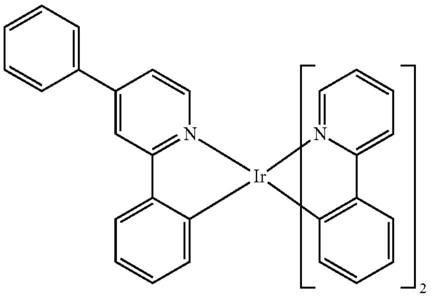
-continued
D-43
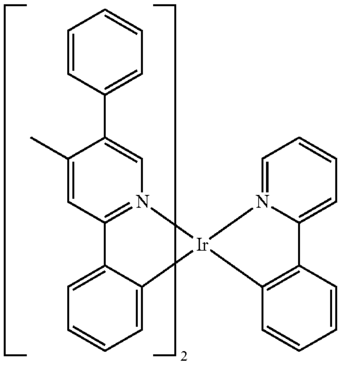
D-44
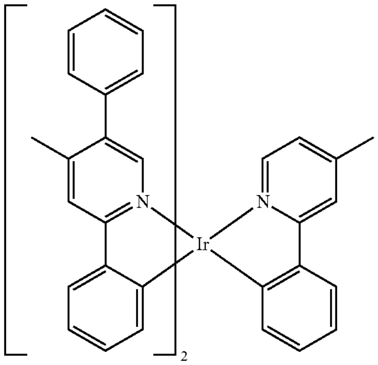
D-45
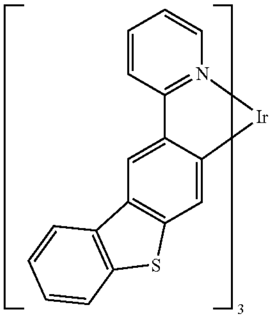
D-46
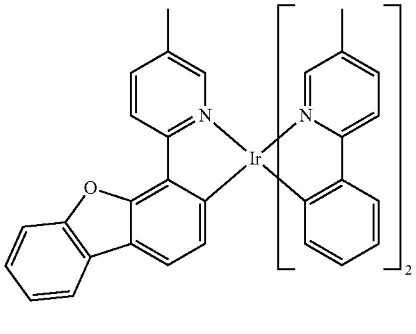

D-47
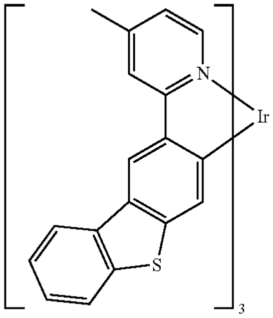
D-48
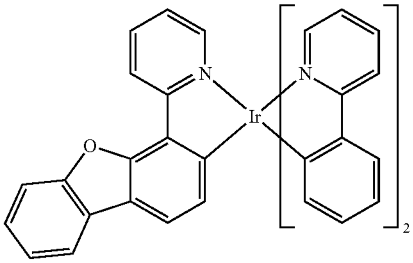
D-49
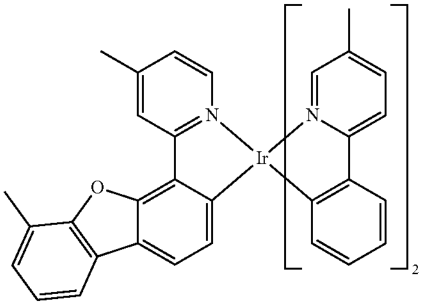
D-50
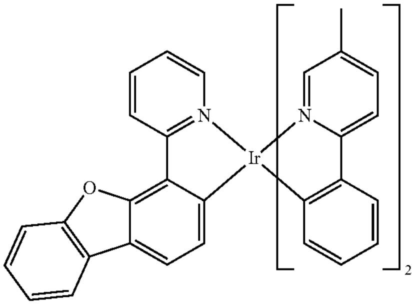
D-51
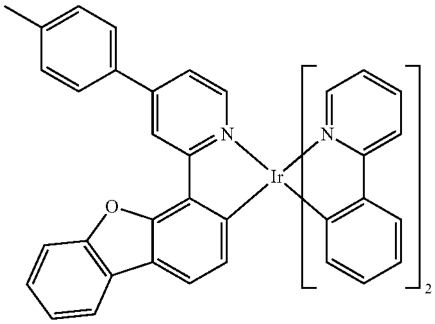
D-52
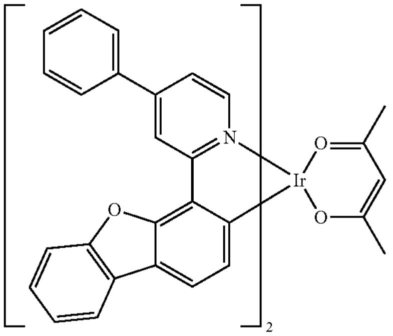
D-53
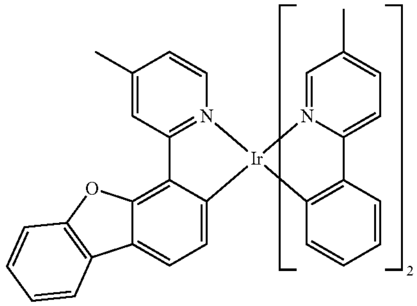
D-54
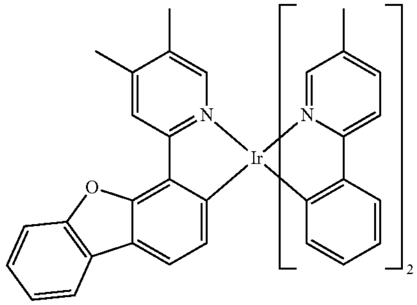
D-55
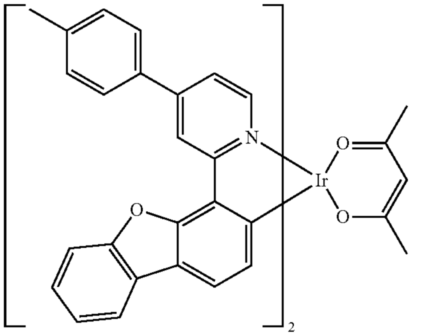
D-56
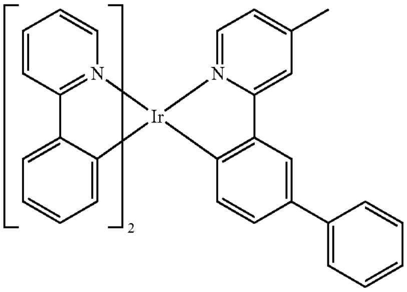

-continued
D-57
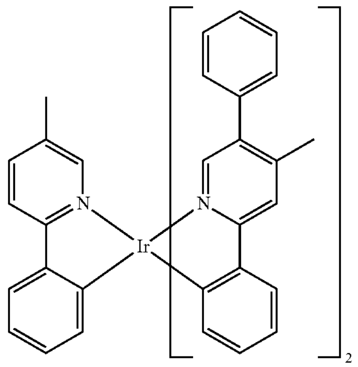
D-58
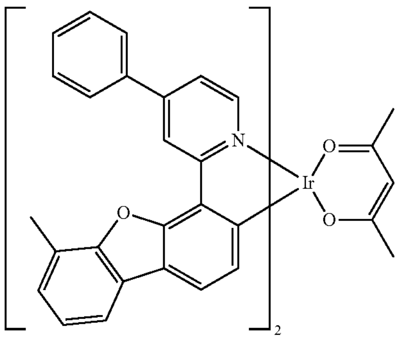
D-59
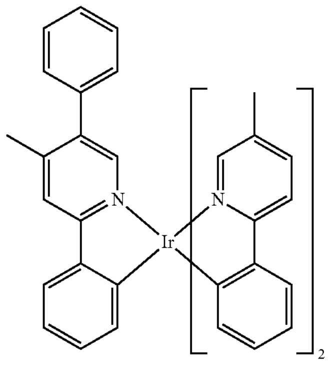
D-60
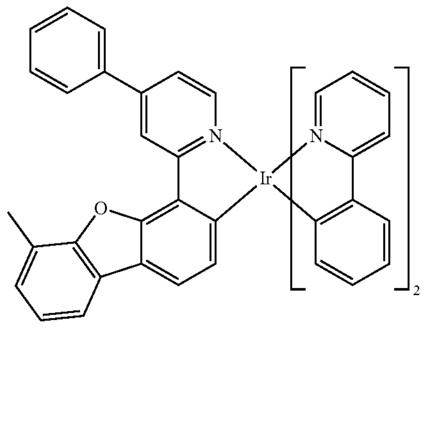
-continued
D-61
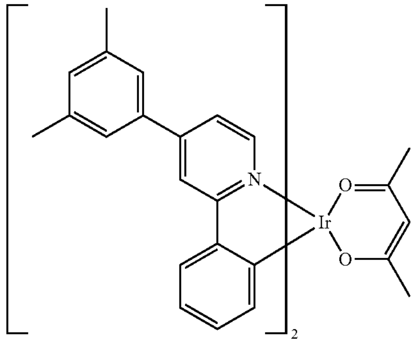
D-62
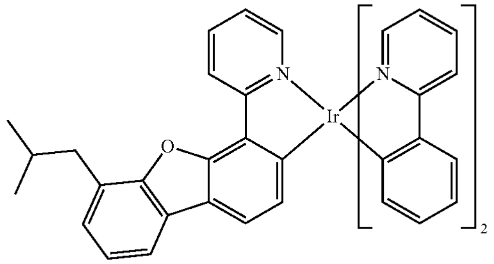
D-63
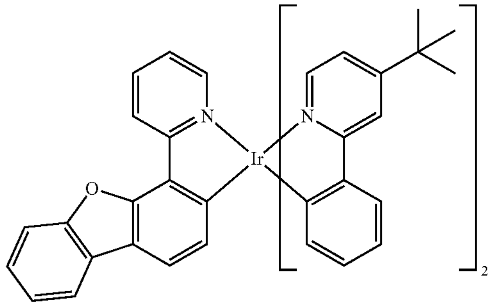
D-64
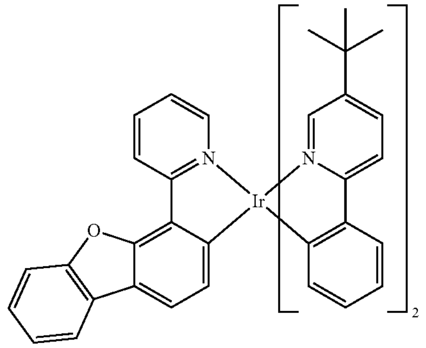
D-65
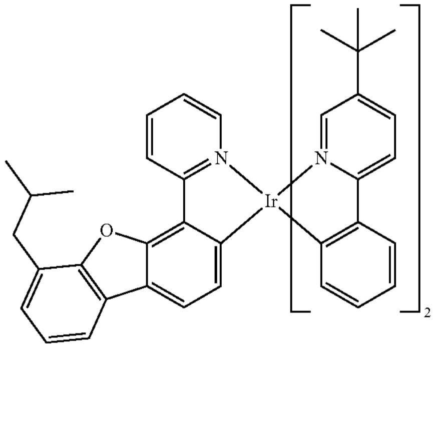

-continued
D-66
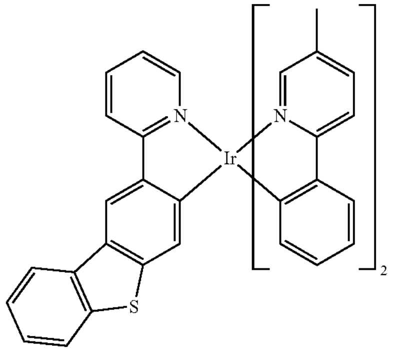
D-67
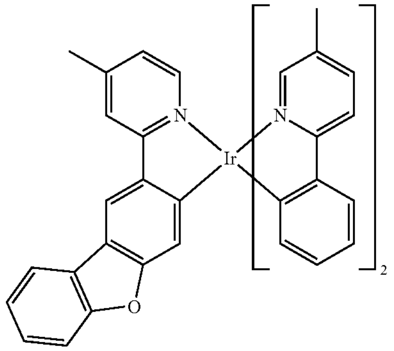
D-68
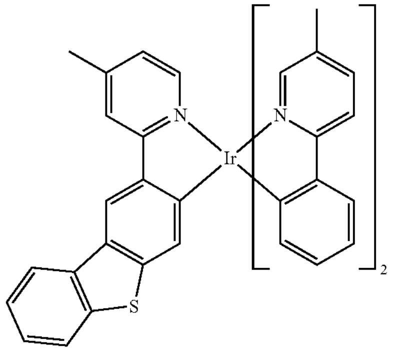
D-69
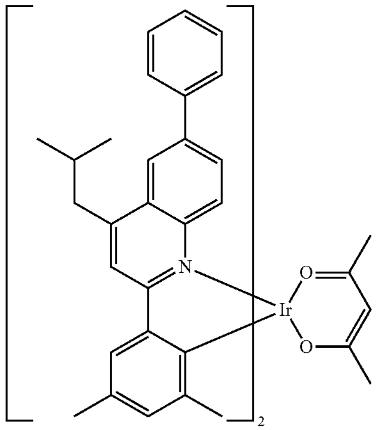
-continued
D-70
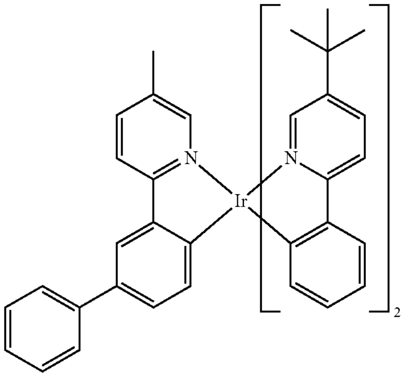
D-71
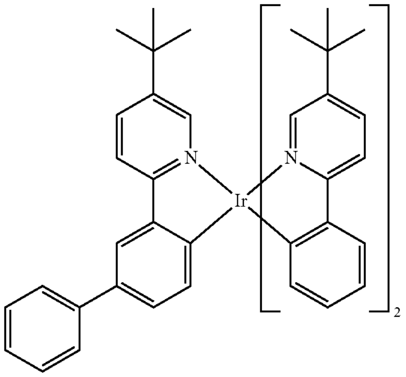
D-72
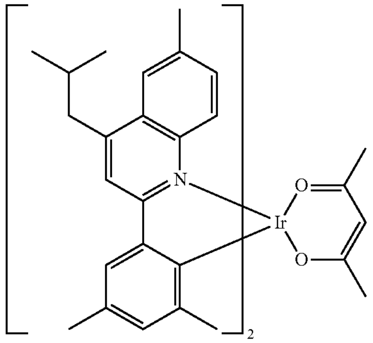
D-73
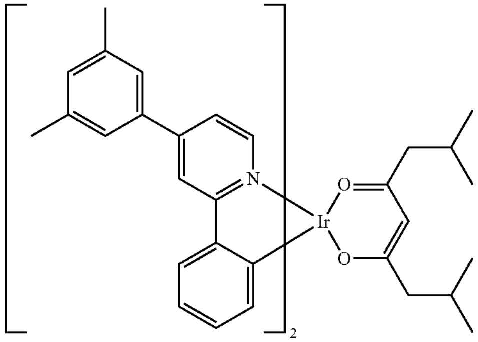

D-74
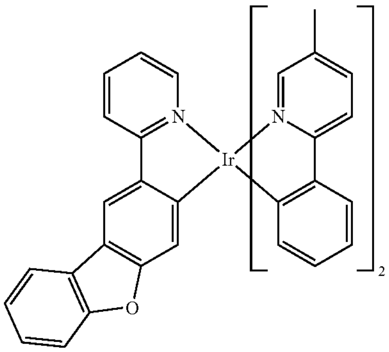
D-75
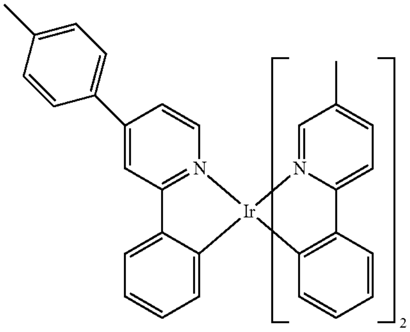
D-76
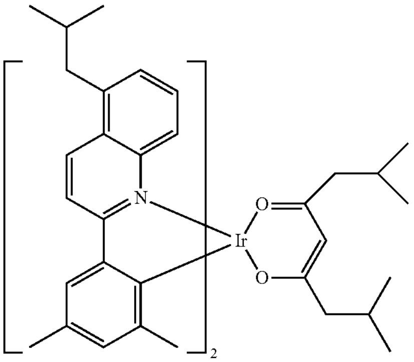
D-77
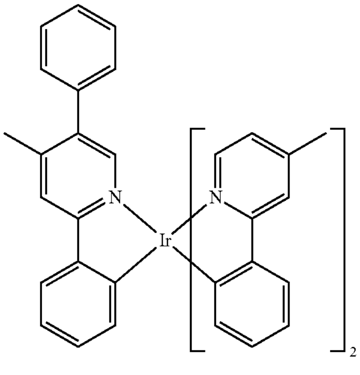
D-78
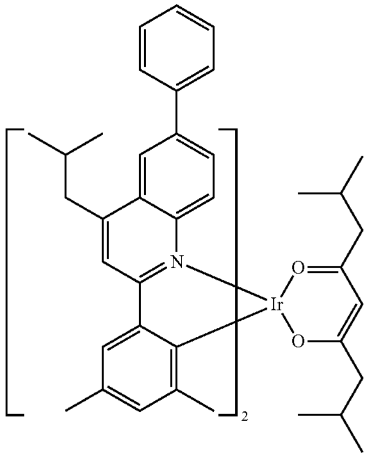
D-79
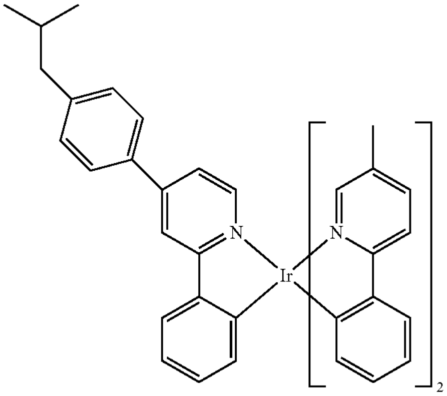
D-80
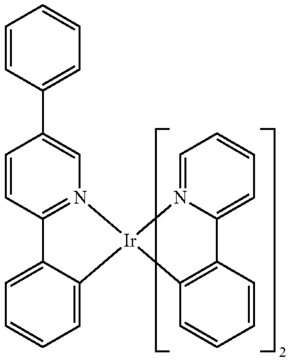
D-81
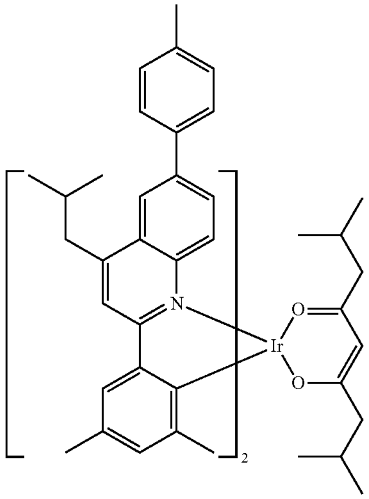

-continued
D-82
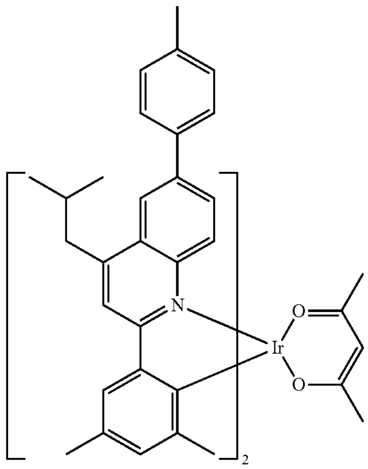
D-83
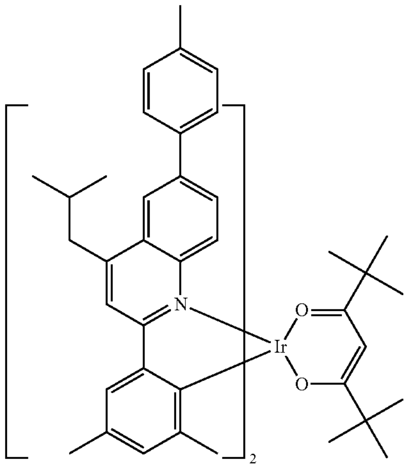
D-84
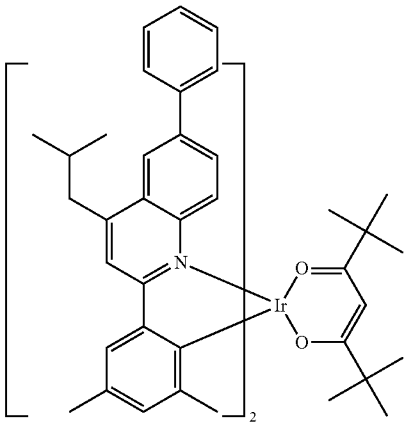
-continued
D-85
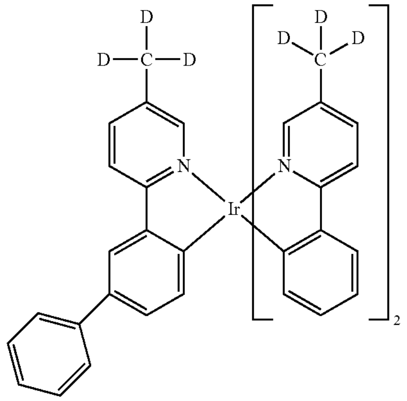
D-86
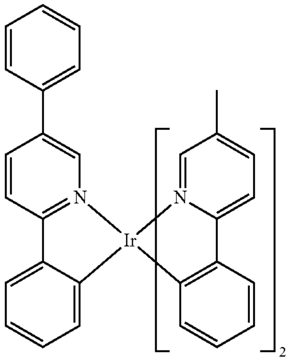
D-87
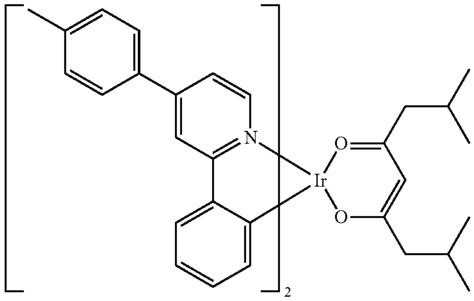
D-88
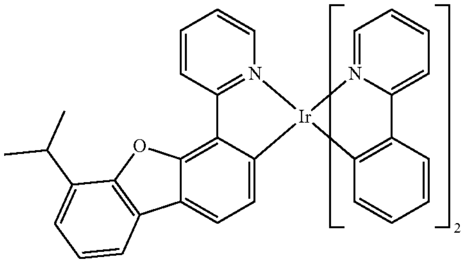
D-89
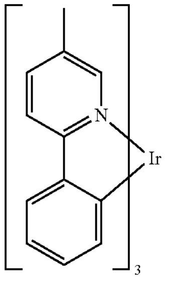

-continued
D-90
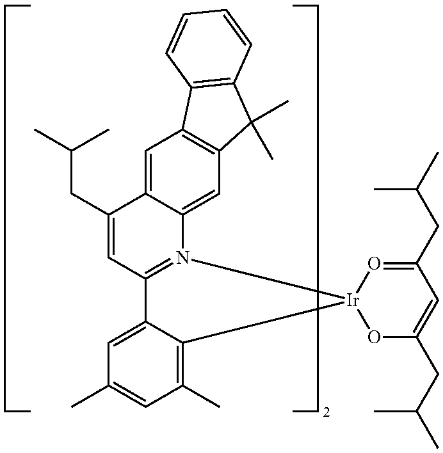
D-91
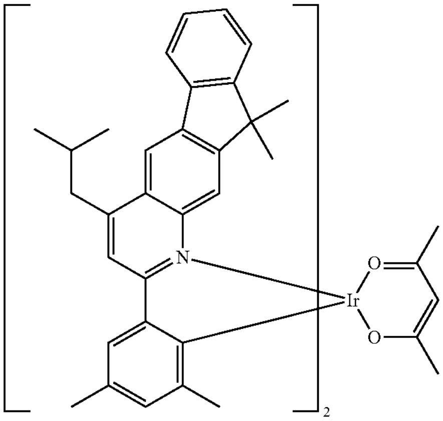
D-92
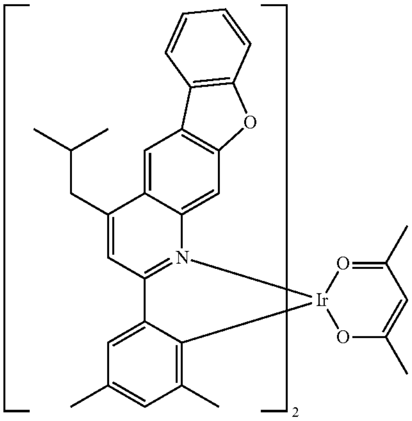
-continued
D-93
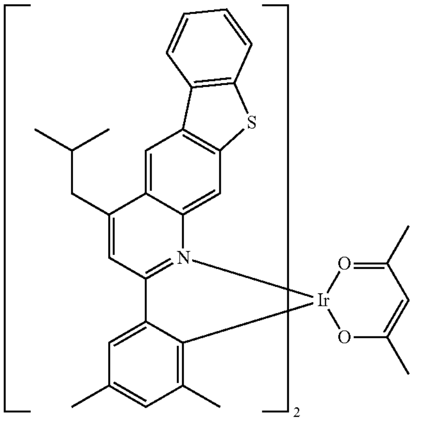
D-94
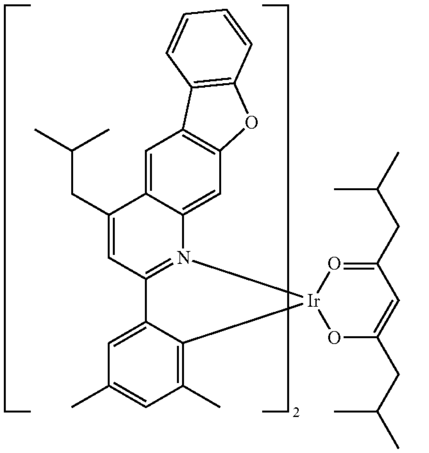
D-95
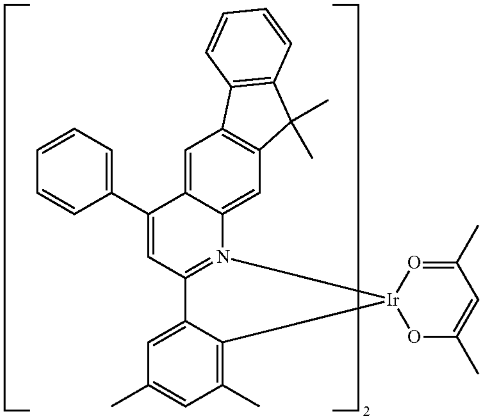

-continued
D-96
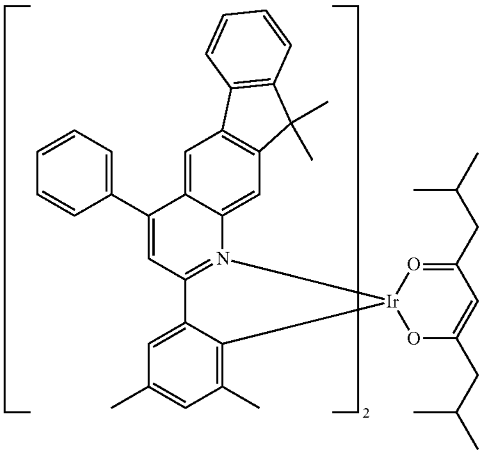
D-97
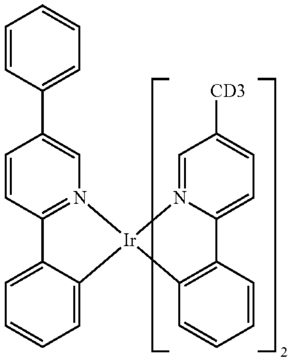
D-98
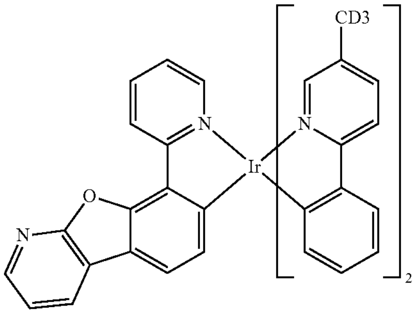
D-99
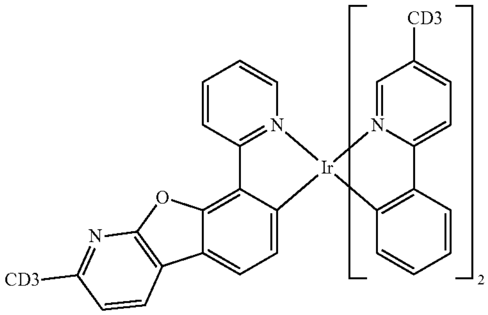
-continued
D-100
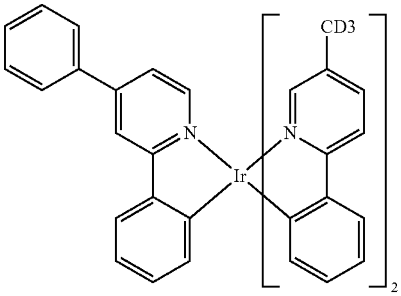
D-101
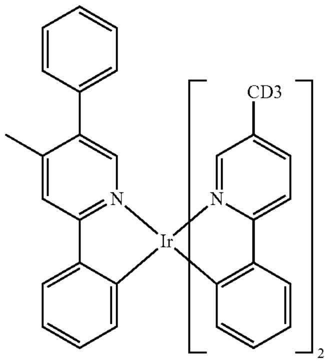
D-102
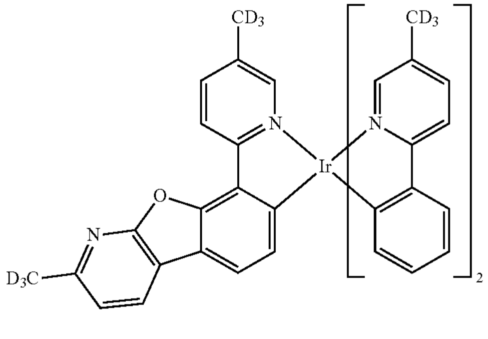
D-103
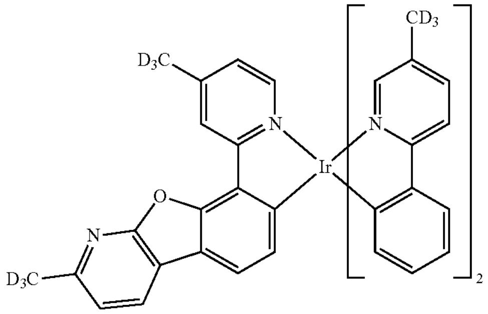

-continued
D-104
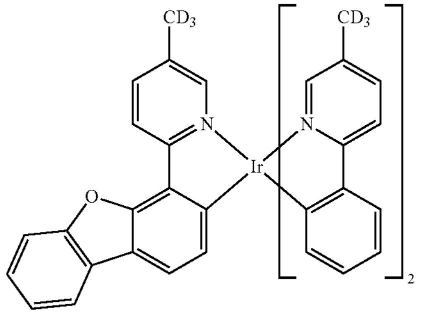
D-105
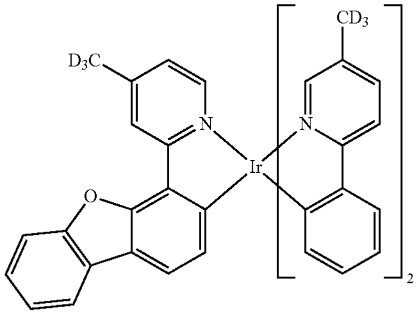
D-106
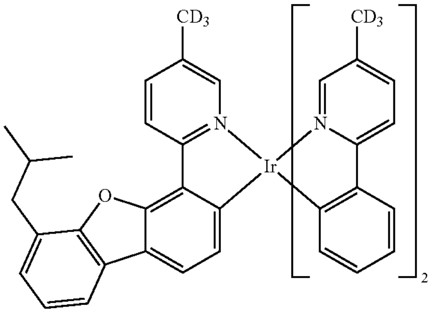
D-107
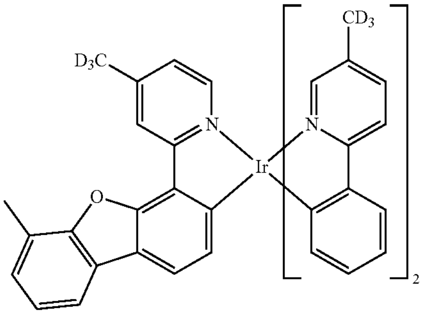
D-108
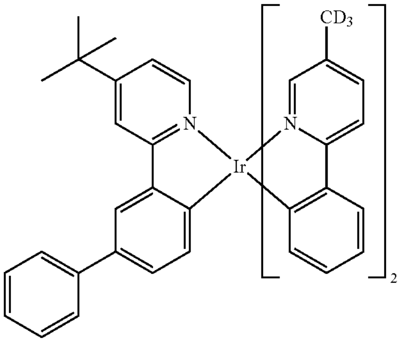
-continued
D-109
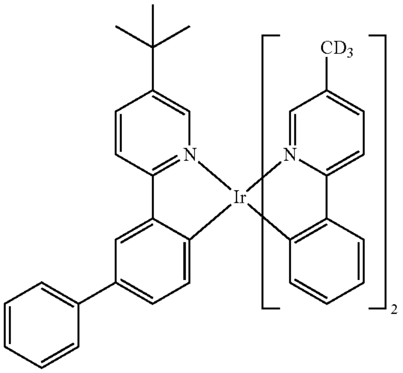
D-110
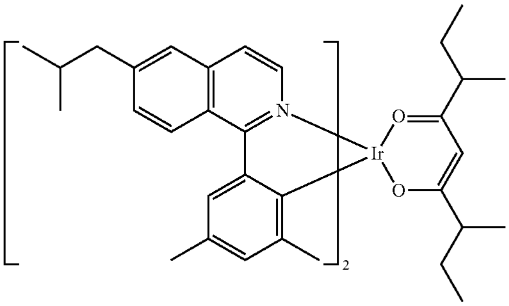
D-111
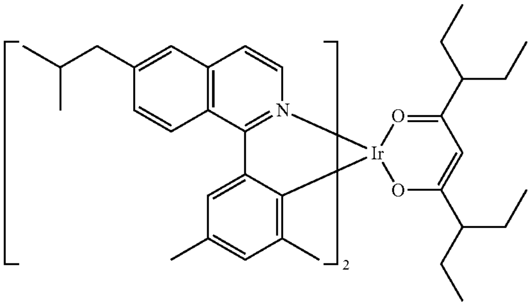
D-112
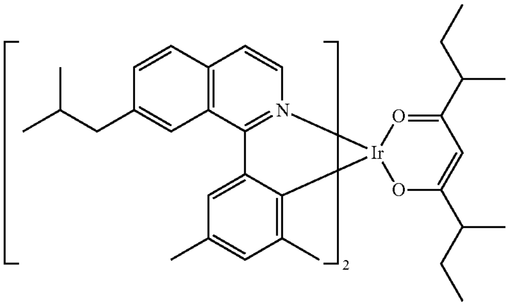

-continued
D-113
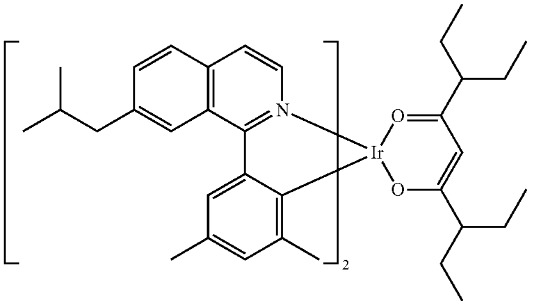
D-114
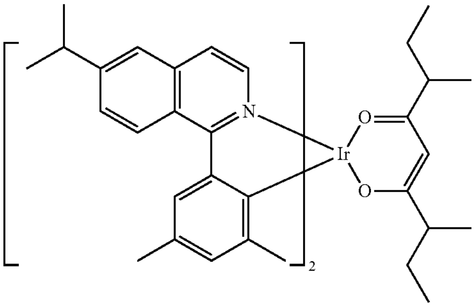
D-115
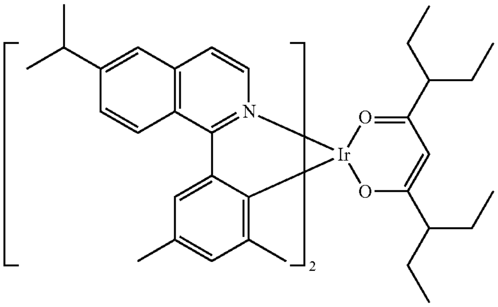
D-116
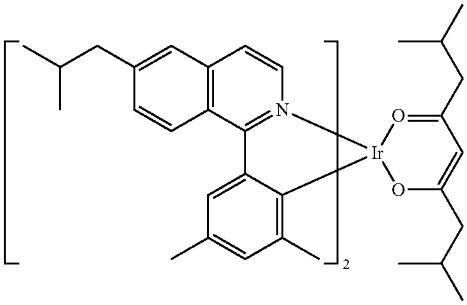
D-117
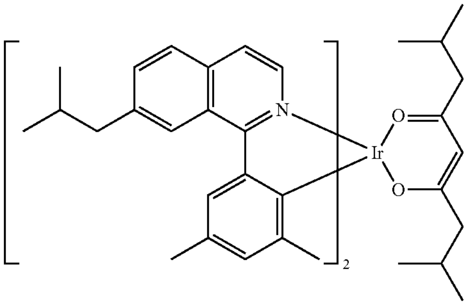
-continued
D-118
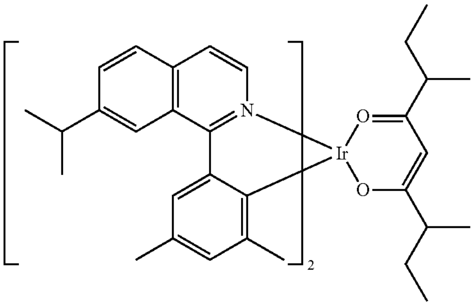
D-119
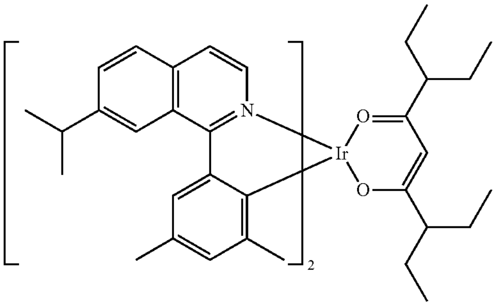
Hereinafter, the preparation method of the compound of the present disclosure, and the properties thereof will be explained in detail with reference to the representative compounds of the present disclosure. However, the present disclosure is not limited to the following examples.
Example 1: Preparation of Compound C1-4
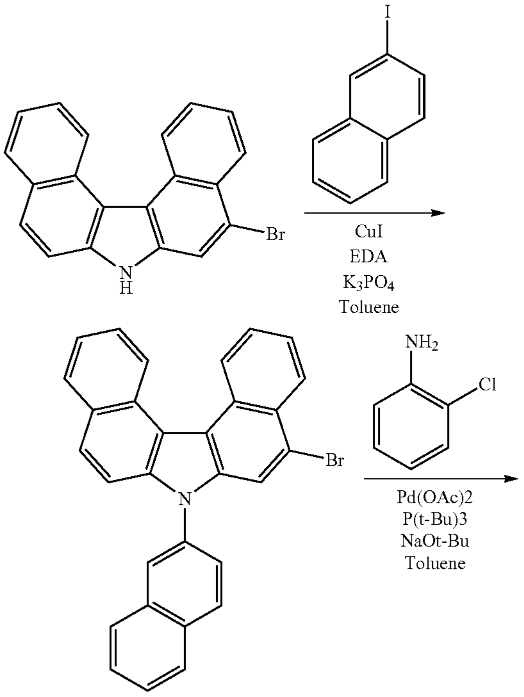
1-1

-continued

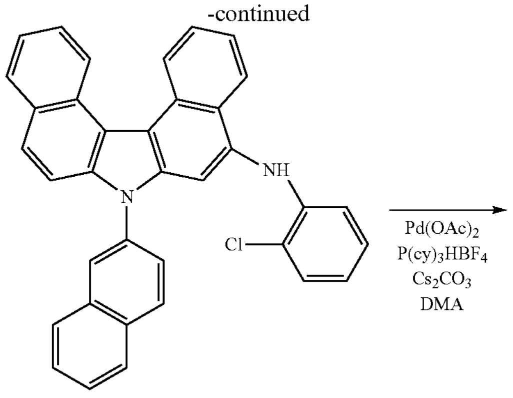

1-2

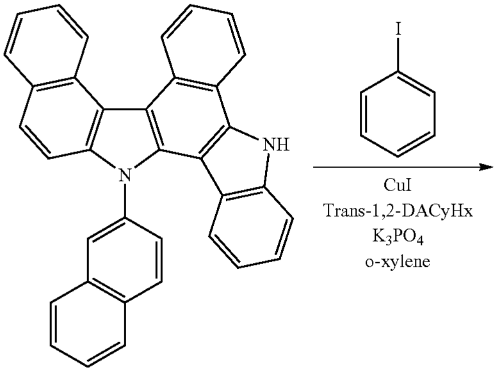

1-3

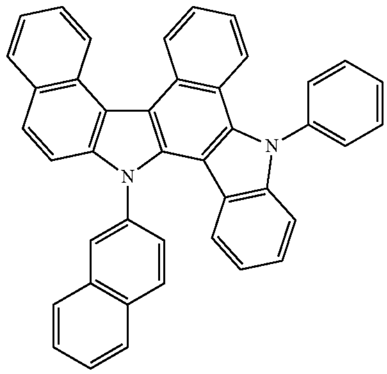

C1-4

Synthesis of Compound 1-1

8.5 g of 5-bromo-7H-dibenzo[c,g]carbazole (0.025 mol), 10.7 g of 2-iodo-naphthalene (0.042 mol), 1.49 g of ethylenediamine (EDA) (0.025 mol), 13.1 g of $K_3PO_4$ (0.062 mol), and 2.3 g of CuI (0.012 mol) were placed in 124 mL of toluene, and the mixture was stirred under reflux for one day. After completion of the reaction, the reaction mixture was cooled to room temperature and extracted with methylene chloride (MC). Thereafter, the extracted organic layer was distilled under reduced pressure and then purified by column chromatography with MC/Hex to obtain 7.6 g of compound 1-1 (yield: 58%).

Synthesis of Compound 1-2

7.5 g of compound 1-1 (0.016 mol), 2.4 g of 2-chlorobenzeneamine (0.019 mol), 0.36 g of $Pd(OAc)_2$ (0.002 mol), 0.15 g of $P(t\text{-}Bu)_3$ (0.003 mol), and 3.8 g of NaOt-Bu (0.04 mol) were placed in 80 mL of toluene, and the mixture was stirred at 100° C. for one day. After completion of the reaction, the reaction mixture was cooled to room temperature and extracted with distilled water and EA. The extracted organic layer was distilled under reduced pressure, and then purified by column chromatography with MC/Hex to obtain 3.6 g of compound 1-2 (yield: 43%).

Synthesis of Compound 1-3

5.8 g of compound 1-2 (0.011 mol), 0.82 g of $P(Cy)_3HBF_4$ (0.002 mol), 0.25 g of $Pd(OAc)_2$ (0.001 mol), and 10.9 g of $Cs_2CO_3$ (0.033 mol) were placed in 44.4 mL of DMA, and the mixture was stirred under reflux for one day. After completion of the reaction, the reaction mixture was cooled to room temperature and extracted with distilled water and MC. The extracted organic layer was distilled under reduced pressure, and then purified by column chromatography with MC/Hex to obtain 4.2 g of compound 1-3 (yield: 76%).

Synthesis of Compound 1-4

4.2 g of compound 1-3 (0.009 mol), 1.9 mL of iodobenzene (0.017 mol), 0.8 g of CuI (0.004 mol), 2 mL of 1,2-diaminocyclohexane (0.018 mol), and 3.7 g of $K_3PO_4$ (0.017 mol) were placed in 44 mL of o-xylene, and the mixture was stirred under reflux for one day. After extracting with MC, the reaction mixture was distilled under reduced pressure. Thereafter, the residue was purified by column chromatography with MC/Hex to obtain 1.2 g of compound C1-4 (yield: 24%).

$^1H$ NMR (600 MHz, DMSO,δ) 9.19-9.07 (d, 1H), 9.01-9.00 (d, 1H), 8.37 (s, 1H), 8.35-8.34 (d, 1H), 8.23-8.22 (d, 1H), 8.15-8.14 (d, 1H), 8.06-8.05 (d, 1H), 7.94-7.92 (m, 2H), 7.78-7.56 (m, 12H), 7.30-7.27 (t, 1H), 7.11-7.09 (t, 1H), 7.05-7.04 (d, 1H), 6.41-6.39 (t, 1H), 5.88-5.86 (d, 1H)

| | MW | M.P. |
|---|---|---|
| C1-4 | 558.7 | 272.6° C. |

Example 2: Preparation of Compound C1-11

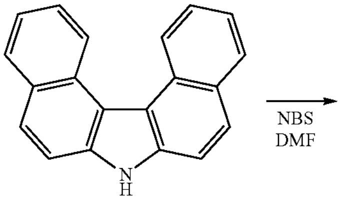

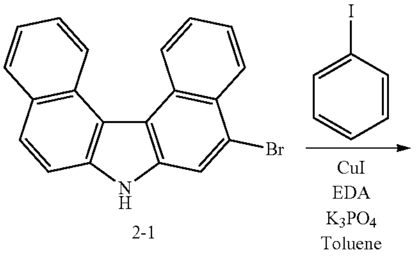

2-1

-continued

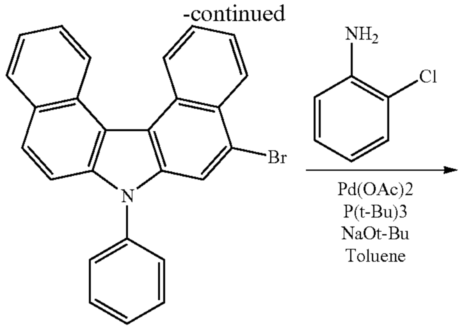

2-2

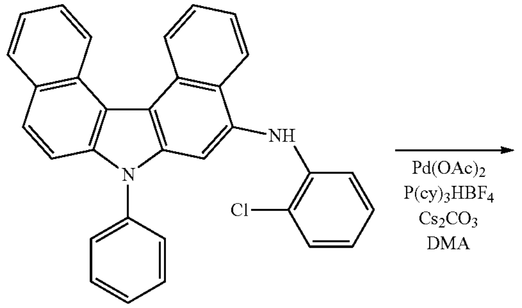

2-3

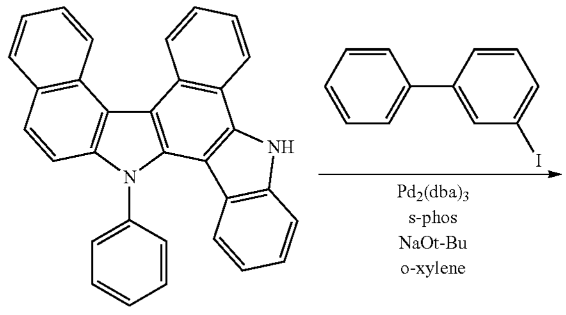

2-4

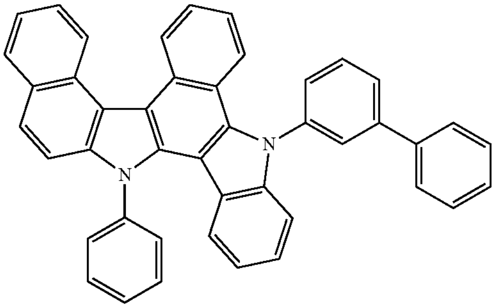

C1-11

Synthesis of Compound 2-1

100 g of 7H-dibenzo[c,g]carbazole (374 mmol) was dissolved in 1.8 L of DMF, and the mixture was cooled and stirred at 0° C. 60 g of N-bromosuccinimide (336 mmol) was dissolved in 200 mL of DMF, and the mixture was added dropwise for 2.5 hours. The mixture was stirred at room temperature for 2 hours. After completion of the reaction, the reaction mixture was washed with $Na_2S_2O_3$ aqueous solution and water. The organic layer was extracted with ethyl acetate, and the residual moisture was removed by using $MgSO_4$. The residue was dried and purified by silica filter to obtain 106 g of compound 2-1 (yield: 82%).

Synthesis of Compound 2-2

15 g of compound 2-1 (43.32 mmol), 17.6 g of iodobenzene (86.65 mmol), 2.6 g of EDA (43.32 mmol), 23 g of $K_3PO_4$ (108.3 mmol), and 4.1 g of CuI (21.66 mmol) were placed in 216 mL of toluene, and the mixture was stirred under reflux for one day. After completion of the reaction, the reaction mixture was cooled to room temperature and extracted with MC. Thereafter, the extracted organic layer was distilled under reduced pressure, and then purified by column chromatography with MC/Hex to obtain 9 g of compound 2-2 (yield: 50%).

Synthesis of Compound 2-3

9 g of compound 2-2 (21.31 mmol), 4 g of 2-chlorobenzeneamine (31.96 mmol), 0.47 g of $Pd(OAc)_2$ (2.131 mmol), 0.86 g of $P(t\text{-}Bu)_3$ (4.262 mmol), and 5.1 g of NaOt-Bu (53.27 mmol) were placed in 108 mL of toluene, and the mixture was stirred at 140° C. for one day. After completion of the reaction, the reaction mixture was cooled to room temperature and extracted with distilled water and EA. The extracted organic layer was distilled under reduced pressure, and then purified by column chromatography with MC/Hex to obtain 7.5 g of compound 2-3 (yield: 75%).

Synthesis of Compound 2-4

7.5 g of compound 2-3 (16.02 mmol), 1.17 g of $P(Cy)_3HBF_4$ (3.204 mmol), 0.36 g of $Pd(OAc)_2$ (1.602 mmol), and 15.65 g of $Cs_2CO_3$ (48.06 mmol) were placed in 80 mL of DMA, and the mixture was stirred under reflux for one day. After completion of the reaction, the reaction mixture was cooled to room temperature and extracted with distilled water and MC. The extracted organic layer was distilled under reduced pressure, and then purified by column chromatography with MC/Hex to obtain 4 g of compound 2-4 (yield: 58%).

Synthesis of Compound C1-11

4 g of compound 2-4 (9.25 mmol), 3.1 g of 3-iodo-1,1'-biphenyl (11.1 mmol), 0.42 g of $Pd_2(dba)_3$ (0.46 mmol), 0.38 g of s-phos (0.92 mmol), and 2.2 g of NaOt-Bu (23.13 mmol) were placed in 46 mL of o-xylene, and the mixture was stirred under reflux for one day. The reaction mixture was extracted with MC, and then distilled under reduced pressure. Thereafter, the residue was purified by column chromatography with MC/Hex to obtain 1.2 g of compound C1-11 (yield: 23%).

$^1H$ NMR (600 MHz,DMSO,δ) 9.17-915 (d, 1H), 9.00-8.98 (d, 1H), 8.15-8.13 (d, 1H), 8.07-8.06 (d, 1H), 7.98 (m, 1H), 7.95-7.94 (d, 1H), 7.88-7.86 (t, 1H), 7.82-7.80 (m, 7H), 7.71-7.67 (m, 2H), 7.65-7.61 (m, 2H), 7.60-7.55 (m, 2H), 7.49-7.47 (t, 2H), 7.42-7.39 (t, 1H), 7.30-7.27 (t, 1H), 7.26-7.23 (t, 1H), 7.20-7.19 (d, 1H), 6.80-6.77 (t, 1H), 5.97-5.95 (d, 1H)

| | MW | M.P. |
|---|---|---|
| C1-11 | 584.7 | 249.6° C. |

Example 3: Preparation of Compound C1-1

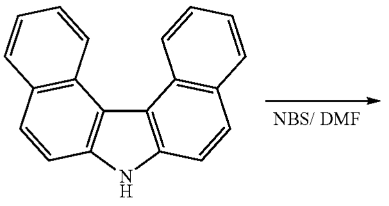

-continued

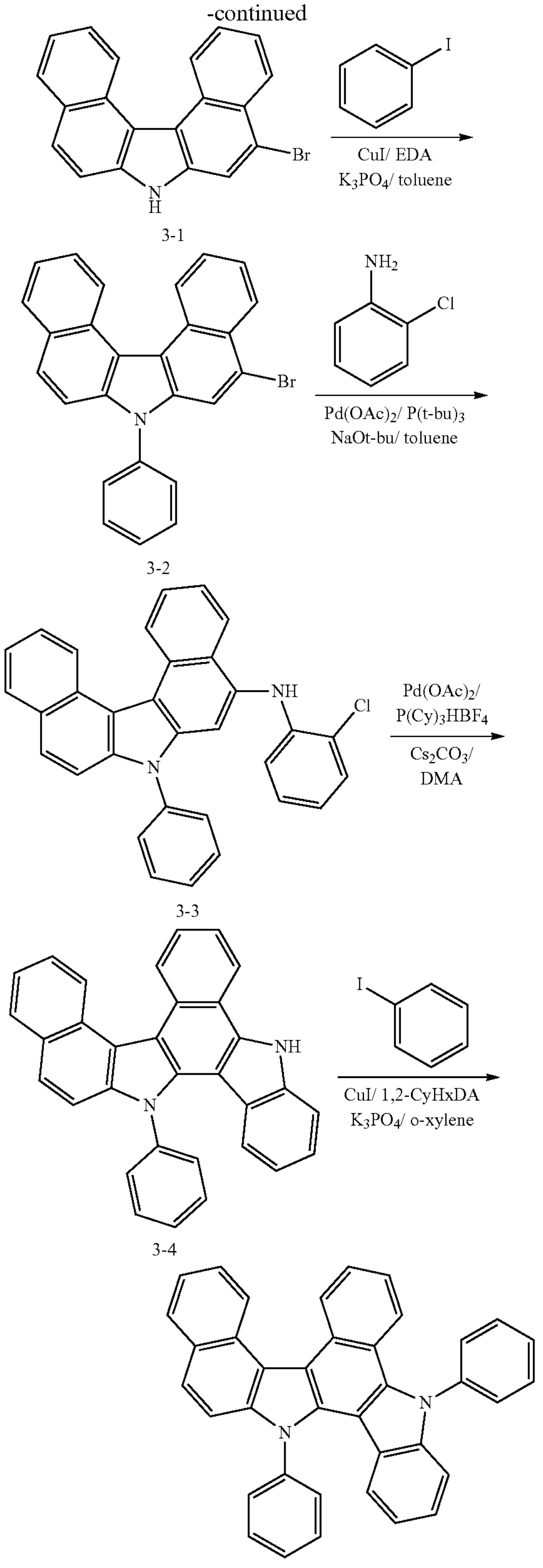

Synthesis of Compound 3-1

In a flask, 60 g of 7H-dibenzo[c,g]carbazole (224 mmol) was dissolved in 900 mL of DMF, and the mixture was cooled and stirred at 0° C. 36 g of NBS (202 mmol) was dissolved in 220 mL of DMF, and the mixture was added dropwise for 2.5 hours. The mixture was stirred at room temperature for 2 hours. After completion of the reaction, the reaction mixture was washed with $Na_2S_2O_3$ aqueous solution and water. The organic layer was extracted with ethyl acetate, and the residual moisture was removed by using $MgSO_4$. The residue was dried and purified by silica filter to obtain 79 g of compound 3-1 (yield: 79%).

Synthesis of Compound 3-2

76 g of compound 3-1 (5-bromo-7H-dibenzo[c,g]carbazole) (220 mmol), 90 g of iodobenzene (439 mmol), 20.90 g of CuI (110 mmol), 13 g of ethylenediamine (110 mmol), and 139 g of $K_3PO_4$ (659 mmol) were placed in 1.1 L of toluene, and the mixture was stirred under reflux for 2.5 hours. After adding MeOH, the resultant solid was filtered under reduced pressure. Thereafter, the residue was purified by column chromatography to obtain 55.1 g of compound 3-2 (yield: 60%).

Synthesis of Compound 3-3

54.6 g of compound 3-2 (129 mmol), 20 g of 2-chloroaniline (155 mmol), 2.9 g of $Pd(OAc)_2$ (13 mmol), 5.2 g of $P(t\text{-}Bu)_3$ (26 mmol), and 31 g of NaOt-Bu (323 mmol) were placed in 650 mL of toluene, and the mixture was stirred under reflux for 4 hours. The reaction mixture was cooled to room temperature, and $NH_4Cl(aq)$ was added. The reaction mixture was extracted with EA, and then dried with magnesium sulfate. The extracted organic layer was distilled under reduced pressure, and then purified by column chromatography to obtain 47.9 g of compound 3-3 (yield: 79%).

Synthesis of Compound 3-4

48 g of compound 3-3 (103 mmol), 2.3 g of $Pd(OAc)_2$ (10 mmol), 7.6 g of ligand (tricyclohexylphosphonium tetrafluoroborate) (21 mmol), and 100 g of $Cs_2CO_3$ (308 mmol) were placed in 400 mL of DMA, and the mixture was stirred under reflux for 1 hour. The reaction mixture was cooled to room temperature, and $NH_4Cl(aq)$ was added. The reaction mixture was extracted with MC, and then dried with magnesium sulfate. The extracted organic layer was distilled under reduced pressure, and then purified by column chromatography to obtain 44 g of compound 3-4 (yield: 79%).

Synthesis of Compound C1-1

5 g of compound 3-4 (12 mmol), 3.5 g of iodobenzene (17 mmol), 1.1 g of CuI (6 mmol), 2.6 g of 1,2-diaminocyclohexane (23 mmol), and 4.9 g of $K_3PO_4$ (23 mmol) were placed in 60 mL of o-xylene, and the mixture was stirred under reflux for one day. The reaction mixture was cooled to room temperature, and filtered through celite with MC. The filtrate was distilled under reduced pressure, and then purified by column chromatography with MC/Hex to obtain 1.3 g of compound C1-1 (yield: 22%).

H NMR (600 MHz,DMSO,δ) 9.16-9.15 (d, 1H), 8.99-8.98 (d, 1H), 8.14-8.13 (d, 1H), 7.94-7.93 (d, 1H), 7.94-7.68 (m, 9H), 7.65-7.61 (m, 3H), 7.60-7.54 (m, 3H), 7.25-7.21 (m, 2H), 7.08-7.07 (d, 1H), 6.78-6.76 (m, 1H) 5.95-5.94 (d, 1H)

| | MW | M.P. |
|---|---|---|
| C1-1 | 508.62 | 184° C. |

Example 4: Preparation of Compound C2-1

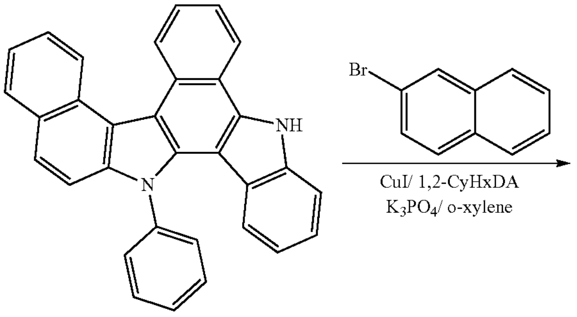

4-1

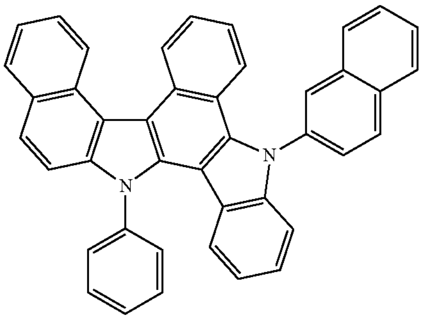

C2-1

7 g of compound 4-1 (16 mmol), 6.7 g of 2-bromonaphthalene (32 mmol), 1.5 g of CuI (8 mmol), 3.7 g of 1,2-diaminocyclohexane (32 mmol), and 10.3 g of $K_3PO_4$ (49 mmol) were placed in 80 mL of o-xylene, and the mixture was stirred under reflux for one day. The reaction mixture was cooled to room temperature, and filtered through celite with MC. The filtrate was distilled under reduced pressure, and then purified by column chromatography with MC/Hex to obtain 1.3 g of compound C2-1 (yield: 22%).

$^1$H NMR (600 MHz, DMSO,δ) 9.17-9.15 (d, 1H), 9.00-8.99 (d, 1H), 8.31-8.30 (m, 2H), 8.20-8.18 (d, 1H), 8.15-8.14 (d, 1H), 8.11-8.10 (d, 1H), 7.95-7.94 (d, 1H), 7.83-7.79 (m, 5H), 7.73-7.69 (m, 4H), 7.60-7.57 (m, 4H), 7.21-7.18 (m, 2H), 7.14-7.13 (d, 1H), 6.78-6.77 (t, 1H) 5.98-5.96 (d, 1H)

| | MW | M.P. |
|---|---|---|
| C2-1 | 558.68 | 263° C. |

Example 5: Preparation of Compound C1-13

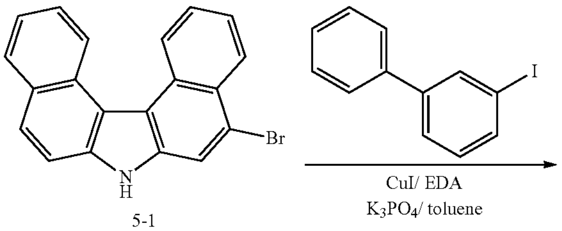

5-1

-continued

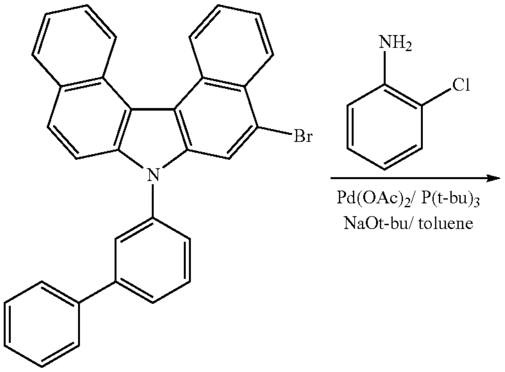

5-2

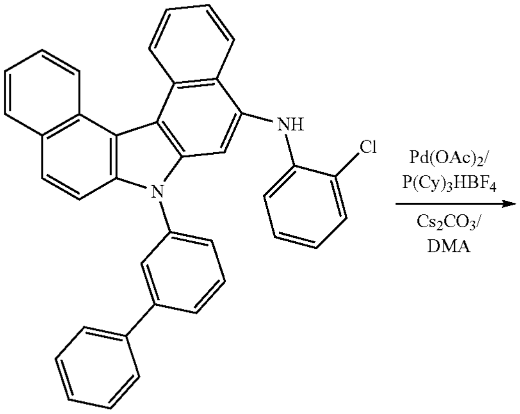

5-3

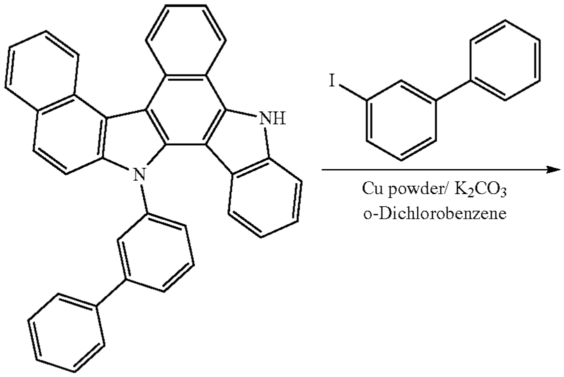

5-4

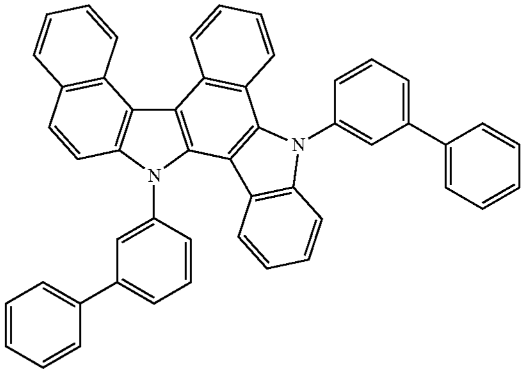

C1-13

Synthesis of Compound 5-2

15 g of compound 5-1 (5-bromo-7H-dibenzo[c,g]carbazole) (220 mmol), 18 g of 3-iodo-1,1'-biphenyl (65 mmol), 4.1 g of CuI (22 mmol), 2.6 g of ethylenediamine (43 mmol), and 23 g of $K_3PO_4$ (108 mmol) were placed in 216 mL of toluene, and the mixture was stirred under reflux for 4 hours. After adding MeOH, the resultant solid was filtered under reduced pressure. Thereafter, the filtrate was purified by column chromatography to obtain 16 g of compound 5-2 (74%).

Synthesis of Compound 5-3

15 g of compound 5-2 (30 mmol), 7.7 g of 2-chloroaniline (60 mmol), 0.67 g of $Pd(OAc)_2$ (3 mmol), 1.2 g of $P(t\text{-}Bu)_3$ (6 mmol), and 7.2 g of NaOt-Bu (75 mmol) were placed in 150 mL of toluene, and the mixture was stirred under reflux for 2 hours. The reaction mixture was cooled to room temperature, and $NH_4Cl$(aq) was added. Thereafter, the reaction mixture was extracted with EA, and then dried with magnesium sulfate. The extracted organic layer was distilled under reduced pressure, and then purified by column chromatography to obtain 10.1 g of compound 5-3 (62%).

Synthesis of Compound 5-4

10 g of compound 5-3 (18 mmol), 0.41 g of $Pd(OAc)_2$ (1.8 mmol), 1.35 g of ligand (tricyclohexylphosphonium tetrafluoroborate) (3.7 mmol), and 18 g of $Cs_2CO_3$ (55 mmol) were placed in 92 mL of DMA, and the mixture was stirred under reflux for 1 hour. The reaction mixture was cooled to room temperature, and $NH_4Cl$(aq) was added. The reaction mixture was extracted with MC, and then dried with magnesium sulfate. The extracted organic layer was distilled under reduced pressure, and then purified by column chromatography to obtain 7.1 g of compound 5-4 (76%).

Synthesis of Compound C1-13

6.7 g of compound 5-4 (13 mmol), 7.4 g of 3-iodo-1,1'-biphenyl (26 mmol), 0.42 g of Cu powder (7 mmol), and 3.6 g of $K_2CO_3$ (26 mmol) were placed in 70 mL of o-dichlorobenzene, and the mixture was stirred under reflux for one day. The reaction mixture was cooled to room temperature, and filtered through celite with MC. The filtrate was distilled under reduced pressure, and then purified by column chromatography with MC/Hex to obtain 3.1 g of compound C1-13 (36%).

H NMR (600 MHz,DMSO,δ) 9.18-9.17 (d, 1H), 9.01-9.00 (d, 1H), 8.16-8.15 (d, 1H), 8.11-8.09 (d, 1H), 8.06-8.05 (m, 2H), 8.00-7.79 (m, 7H), 7.73-7.57 (m, 8H), 7.48-7.38 (m, 6H), 7.30-7.28 (t, 1H), 7.22-7.18 (m, 2H), 6.80-6.78 (t, 1H), 6.07-6.06 (d, 1H)

| | MW | M.P. |
|---|---|---|
| C1-13 | 660.82 | 259° C. |

Example 6: Preparation of Compound C1-65

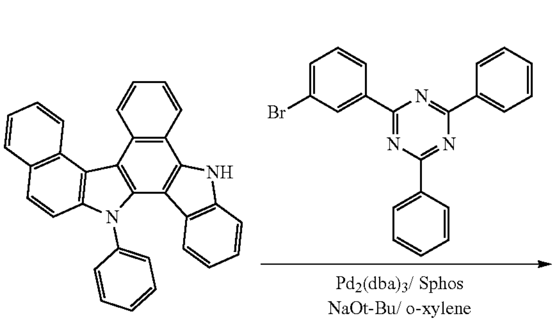

6-4

-continued

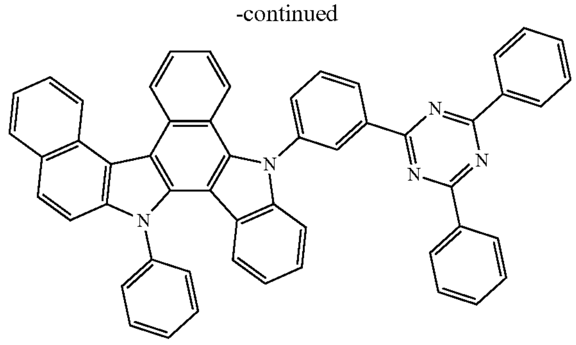

C1-65

5.0 g of compound 6-4 (12 mmol), 6.7 g of 2-(3-bromophenyl)-4,6-diphenyl-1,3,5-triazine (17 mmol), 0.52 g of $Pd_2(dba)_3$ (0.58 mmol), 0.48 g of S-phos (1 mmol), and 31 g of NaOt-Bu (29 mmol) were placed in 60 mL of o-xylene, and the mixture was stirred under reflux for 4 hours. The reaction mixture was cooled to room temperature, and MeOH was added. The resultant solid was filtered under reduced pressure, and purified by column chromatography to obtain 3.0 g of compound C1-65 (35%).

$^1$H NMR (600 MHz, $CDCl_3$,δ) 9.20-9.18 (d, 1H), 9.13-9.12 (d, 2H), 8.14-8.13 (d, 1H), 9.02-9.01 (d, 1H), 8.84-8.83 (d, 1H), 8.16-8.15 (d, 1H), 7.97-7.95 (m, 3H), 7.83-7.80 (m, 5H), 7.77-7.57 (d, 11H), 7.34-7.32 (m, 1H), 7.28-7.25 (m, 2H), 6.83-6.81 (m, 1H), 5.99-5.97 (d, 1H)

| | MW | M.P. |
|---|---|---|
| C1-65 | 739.88 | 345° C. |

Example 7: Preparation of Compound C1-61

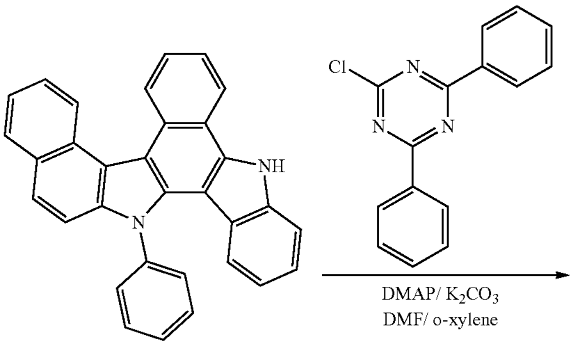

7-4

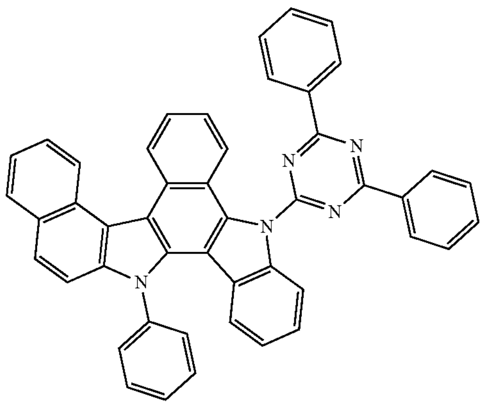

C1-61

5.0 g of compound 7-4 (12 mmol), 4.6 g of 2-chloro-4,6-diphenyl-1,3,5-triazine (17 mmol), 0.71 g of DMAP (6 mmol), and 4.0 g of $K_2CO_3$ (29 mmol) were placed in 80 mL of DMF and 60 mL of o-xylene, and the mixture was stirred under reflux for one day. The reaction mixture was cooled to room temperature, and MeOH was added. The resultant solid was filtered under reduced pressure, and purified by column chromatography to obtain 2.6 g of compound C1-61 (34%).

$^1H$ NMR (600 MHz, $CDCl_3$,δ) 9.22-9.21 (d, 1H), 9.17-9.16 (d, 1H), 8.66-8.65 (d, 1H), 8.56-8.55 (d, 4H), 8.19-817 (d, 1H), 8.01-8.00 (m, 1H), 7.83-7.79 (m, 6H), 7.74-7.57 (m, 10H), 7.45-7.38 (m, 2H), 6.92-6.91 (m, 1H), 5.97-5.95 (m, 1H)

| | MW | M.P. |
|---|---|---|
| C1-61 | 663.78 | 311° C. |

Example 8: Preparation of Compound C1-69

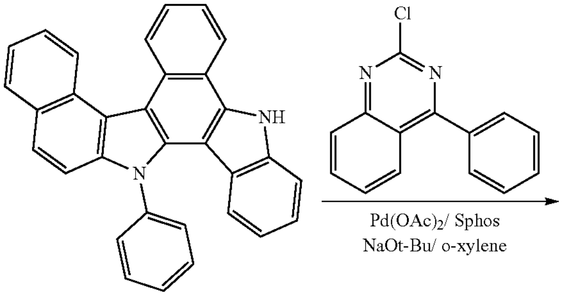

8-4

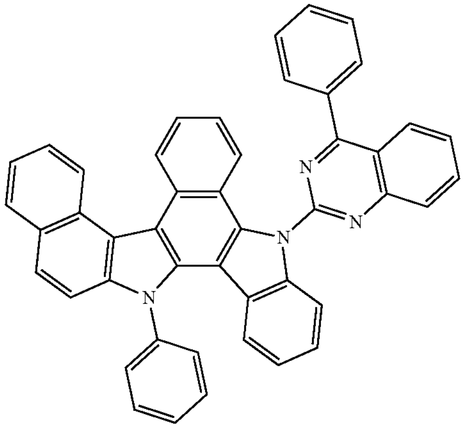

C1-69

5.0 g of compound 8-4 (12 mmol), 5.0 g of 2-chloro-4-phenylquinazoline (21 mmol), 0.52 g of $Pd(OAc)_2$ (0.81 mmol), 0.71 g of Sphos (2 mmol), and 1.1 g of NaOt-Bu (12 mmol) were placed in 100 mL of o-xylene, and the mixture was stirred under reflux for 5 hours. The reaction mixture was cooled to room temperature, and MeOH was added. The resultant solid was filtered under reduced pressure, and purified by column chromatography to obtain 1.4 g of compound C1-69 (19%).

$^1H$ NMR (600 MHz, $CDCl_3$,δ) 9.18-9.17 (d, 1H), 9.07-9.06 (d, 1H), 8.26-8.23 (m, 2H), 8.19-8.15 (m, 2H), 8.06-8.04 (m, 1H), 7.97-7.96 (m, 1H), 7.91-7.88 (m, 1H), 7.83-7.78 (m, 7H), 7.74-7.71 (m, 1H), 7.68-7.55 (m, 5H), 7.45-7.44 (m, 1H), 7.35-7.29 (m, 2H), 6.86-6.83 (t, 1H), 5.94-5.93 (d, 1H)

| | MW | M.P. |
|---|---|---|
| C1-69 | 636.76 | 297° C. |

Example 9: Preparation of Compound C2-52

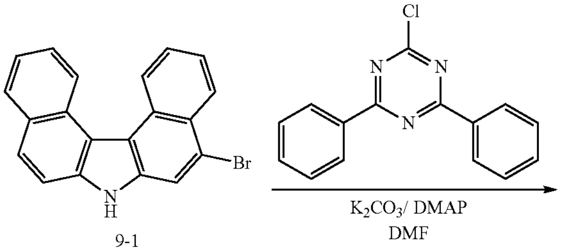

9-1

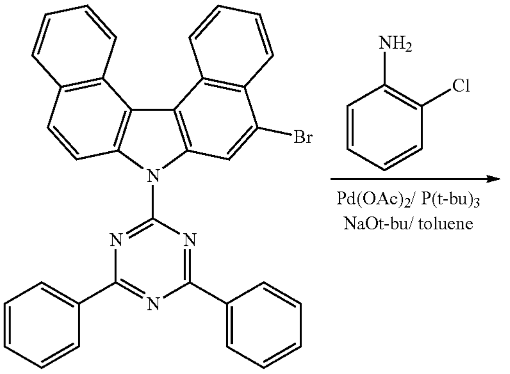

9-2

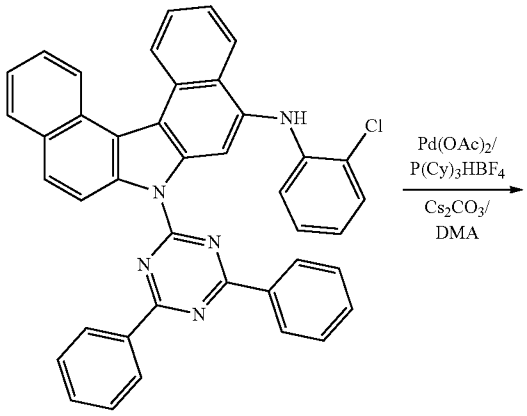

9-3

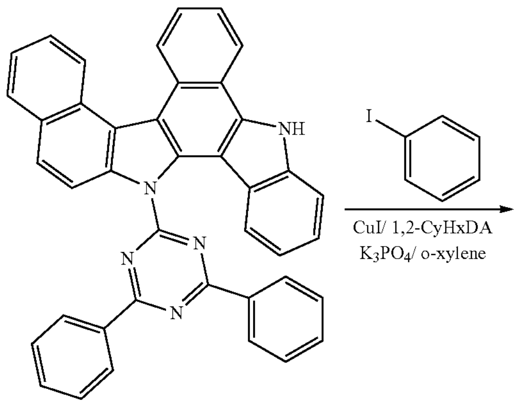

9-4

-continued

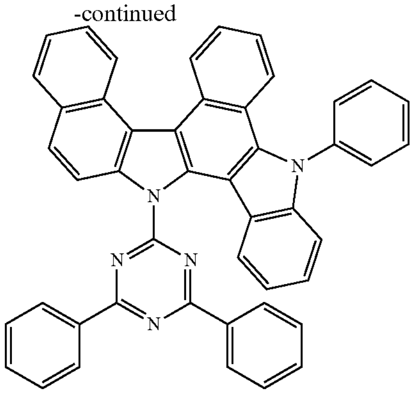

C2-52

Synthesis of Compound 9-2

20 g of compound 1-1 (5-bromo-7H-dibenzo[c,g]carbazole) (58 mmol), 18.6 g of 2-chloro-4,6-diphenyl-1,3,5-triazine (69 mmol), 3.5 g of DMAP (29 mmol), and 20 g of $K_2CO_3$ (145 mmol) were placed in 290 mL of DMF, and the mixture was stirred at 100° C. for 1.5 hours. After adding MeOH, the resultant solid was filtered under reduced pressure. Thereafter, the residue was purified by column chromatography to obtain 26 g of compound 9-2 (78%).

Synthesis of Compound 9-3

18.0 g of compound 9-2 (31 mmol), 4.8 g of 2-chloroaniline (37 mmol), 0.7 g of $Pd(OAc)_2$ (3 mmol), 1.3 g of $P(t\text{-}Bu)_3$ (6 mmol), and 7.5 g of NaOt-Bu (78 mmol) were placed in 150 mL of toluene, and the mixture was stirred under reflux for 2 hours. The reaction mixture was cooled to room temperature, and MeOH was added. The resultant solid was filtered under reduced pressure, and purified by column chromatography to obtain 18.0 g of compound 9-3 (93%).

Synthesis of Compound 9-4

17.5 g of compound 9-3 (28 mmol), 0.7 g of $Pd(OAc)_2$ (3 mmol), 2.1 g of ligand (tricyclohexylphosphonium tetrafluoroborate) (6 mmol), and 27.4 g of $Cs_2CO_3$ (84 mmol) were placed in 112 mL of DMA, and the mixture was stirred under reflux for 2 hours. The reaction mixture was cooled to room temperature, and $NH_4Cl$(aq) was added. The reaction mixture was extracted with MC, and then dried with magnesium sulfate. The extracted organic layer was distilled under reduced pressure, and then purified by column chromatography to obtain 6.1 g of compound 9-4 (37%).

Synthesis of Compound C2-52

5.6 g of compound 9-4 (10 mmol), 2.9 g of iodobenzene (14 mmol), 0.9 g of CuI (5 mmol), 2.2 g of 1,2-diaminocyclohexane (19 mmol), and 4.0 g of $K_3PO_4$ (19 mmol) were placed in 95 mL of o-xylene, and the mixture was stirred for one day. The reaction mixture was cooled to room temperature, and MeOH was added. The resultant solid was filtered under reduced pressure, and purified by column chromatography to obtain 1.0 g of compound C2-52 (16%).

$^1$H NMR (600 MHz,DMSO,δ) 9.12-9.10 (d, 1H), 9.08-9.06 (d, 1H), 8.96-8.95 (d, 1H), 8.40-8.38 (m, 4H), 8.22-8.18 (m, 2H), 7.85-7.83 (m, 2H), 7.80-7.79 (d, 1H), 7.78-7.74 (m, 3H), 7.73-7.64 (m, 5H), 7.57-7.55 (m, 4H), 7.42-7.40 (t, 1H), 7.20-7.19 (t, 1H), 7.15-7.14 (d, 1H) 6.92-6.89 (t, 1H), 6.87-6.86 (d, 1H)

| | MW | M.P. |
|---|---|---|
| C2-61 | 663.78 | 327° C. |

Hereinafter, the driving voltage, the luminous efficiency and the lifespan properties of an OLED including the compound represented by formula 1 will be explained. However, the following examples merely illustrate the properties of an OLED according to the present disclosure in detail, but the present disclosure is not limited to the following examples.

Comparative Example 1: Producing a Red Light-Emitting OLED not According to the Present Disclosure An OLED not according to the present disclosure was produced as follows: A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropanol. The ITO substrate was mounted on a substrate holder of a vacuum vapor deposition apparatus. Compound HI-1 was introduced into a cell of the vacuum vapor deposition apparatus, and then the pressure in the chamber of the apparatus was then controlled to $10^{-7}$ torr. Thereafter, an electric current was applied to the cell to evaporate the above-introduced material, thereby forming a first hole injection layer having a thickness of 80 nm on the ITO substrate. Next, compound HI-2 was introduced into another cell of the vacuum vapor deposition apparatus and was evaporated by applying an electric current to the cell, thereby forming a second hole injection layer having a thickness of 5 nm on the first hole injection layer. Compound HT-1 was then introduced into another cell of the vacuum vapor deposition apparatus and was evaporated by applying an electric current to the cell, thereby forming a first hole transport layer having a thickness of 10 nm on the second hole injection layer. Compound HT-3 was then introduced into another cell of the vacuum vapor deposition apparatus and was evaporated by applying an electric current to the cell, thereby forming a second hole transport layer having a thickness of 60 nm on the first hole transport layer. After forming the hole injection layers and the hole transport layers, a light-emitting layer was formed thereon as follows: Compound C was introduced into one cell of the vacuum vapor depositing apparatus as a host, and compound D-39 was introduced into another cell as a dopant. The two materials were evaporated at a different rate and the dopant was deposited in a doping amount of 3 wt % based on the total amount of the host and dopant to form a light-emitting layer having a thickness of 40 nm on the second hole transport layer. Compound ET-1:compound EI-1 as an electron transport material was then deposited on the light-emitting layer at a weight ratio of 50:50 to form an electron transport layer having a thickness of 35 nm. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the compounds used for producing the OLED were purified by vacuum sublimation at $10^{-6}$ torr.

Device Example 1: Producing a Red Light-Emitting OLED Comprising a Compound According to the Present Disclosure An OLED was produced in the same manner as in Comparative Example 1, except that compound C1-61 was used as a host.

Device Examples 2 to 5: Producing a Red Light-Emitting OLED Comprising a Compound According to the Present Disclosure OLEDs were produced in the same manner as in Comparative Example 1, except that compound HT-2 instead of compound HT-3 was used in the second hole transport layer, and the compound as shown in Table 1 below was used as a host.

The measurement results of the driving voltage based on 50 mA/cm$^2$ of the OLED produced by Comparative Example 1 and Device Examples 1 to 5 are shown in Table 1 below.

TABLE 1

| | Second Hole Transport Layer | Host | Driving Voltage (V) | Driving Voltage Reduction Rate Compared to Comparative Example 1 (%) |
|---|---|---|---|---|
| Comparative Example 1 | HT-3 | C | 6.5 | — |
| Device Example 1 | HT-3 | C1-61 | 5.5 | 15.4 |
| Device Example 2 | HT-2 | C1-61 | 5.4 | 16.9 |
| Device Example 3 | HT-2 | C2-52 | 4.8 | 26.2 |
| Device Example 4 | HT-2 | C1-65 | 4.7 | 27.7 |
| Device Example 5 | HT-2 | C1-69 | 5.2 | 20.0 |

Device Examples 6 to 10: Producing an OLED Comprising a Compound According to the Present Disclosure OLEDs were produced in the same manner as in Comparative Example 1, except that compound HT-2 was used in the second hole transport layer, the first and second hosts, not a single host, shown in Tables 2 and 3 were introduced into different cells so as to have a weight ratio of 50:50, and the dopant was deposited in a doping amount of 3 wt % based on the total amount of the hosts and the dopant to form a light-emitting layer having a thickness of 40 nm on the second hole transport layer.

Comparative Examples 2 and 3: Producing an OLED Comprising Only a Second Host

OLEDs were produced in the same manner as in Comparative Example 1, except that compound HT-2 was used in the second hole transport layer, and only the second host shown in Table 2 or 3 was used as a host.

After producing OLEDs, the driving voltage and power efficiency at 5,000 nits were measured. The lifespan (T98), the time taken to be reduced from 100% to 98% of the luminance, based on a luminance of 5,000 nits of the produced OLEDs are shown in Tables 2 and 3 below.

TABLE 2

| | Second Hole Transport Layer | First Host | Second Host | Driving Voltage (V) | Power Efficiency (lm/W) | Power Efficiency Increase Rate Compared to Comparative Example 2 (%) | Lifespan (T98, hr) |
|---|---|---|---|---|---|---|---|
| Comparative Example 2 | HT-2 | — | H-207 | 4.3 | 11.8 | — | 11 |
| Device Example 6 | HT-2 | C1-4 | H-207 | 3.8 | 18.9 | 60.2 | 160 |
| Device Example 7 | HT-2 | C1-1 | H-207 | 3.9 | 18.8 | 59.3 | 140 |
| Device Example 8 | HT-2 | C2-1 | H-207 | 3.9 | 18.6 | 57.6 | 42 |
| Device Example 9 | HT-2 | C1-11 | H-207 | 3.9 | 18.9 | 60.2 | 153 |

TABLE 3

| | Second Hole Transport Layer | First Host | Second Host | Driving Voltage (V) | Power Efficiency (lm/W) | Power Efficiency Increase Rate Compared to Comparative Example 3 (%) | Lifespan (T98, hr) |
|---|---|---|---|---|---|---|---|
| Comparative Example 3 | HT-2 | — | H-201 | 5.0 | 12.4 | — | 4 |
| Device Example 10 | HT-2 | C1-13 | H-201 | 3.8 | 21.1 | 70.2 | 24 |

From Device Examples 1 to 5 above, it is confirmed that the OLED produced by using the organic electroluminescent compound of the present disclosure as a host has a driving voltage lower by 15% or more as compared to the OLED produced by using a conventional compound as a host. From this, it can be seen that the same battery may be used longer, since the use of the organic electroluminescent compound of the present disclosure in a consumer electronic product requiring low power, in particular, a portable display such as a cellular phone, has a lower power consumption than that in the case of using a conventional compound as a host.

In addition, from Device Examples 6 to 10 above, it can be seen that the OLEDs in which the organic electroluminescent compound of the present disclosure (the first host material) and the second host material of the present disclosure are codeposited, are superior in driving voltage, power efficiency, and lifespan to an OLED using only the second host material of the present disclosure.

The compounds used in the Comparative Examples and Device Examples are shown in Table 4 below.

TABLE 4
| | | |
|---|---|---|
| Hole Injection Layer/ Hole Transport Layer | 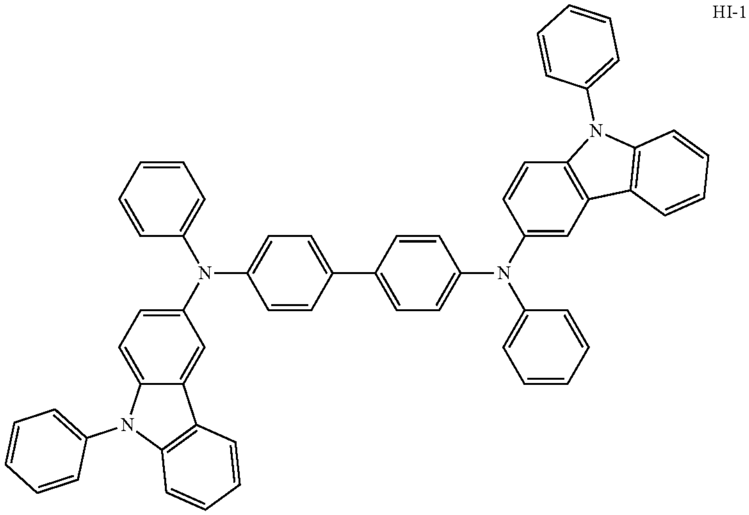 | HI-1 |
| | 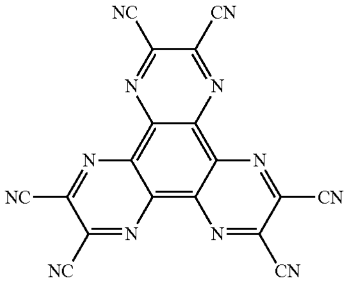 | HI-2 |
| | 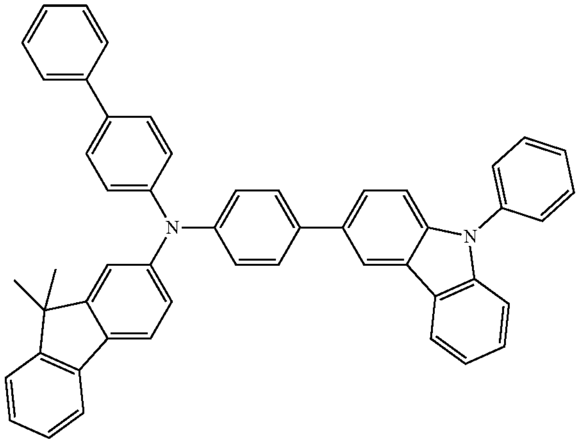 | HT-1 |

TABLE 4-continued
| | | |
|---|---|---|
| | 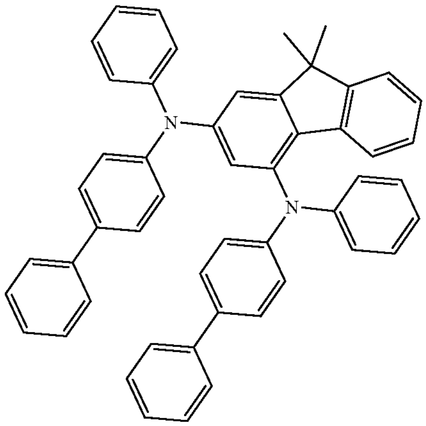 [SMILES: CC1(C)c2ccccc2-c2c(N(c3ccccc3)c3ccc(-c4ccccc4)cc3)cc(N(c3ccccc3)c3ccc(-c4ccccc4)cc3)cc21] | HT-2 |
| | 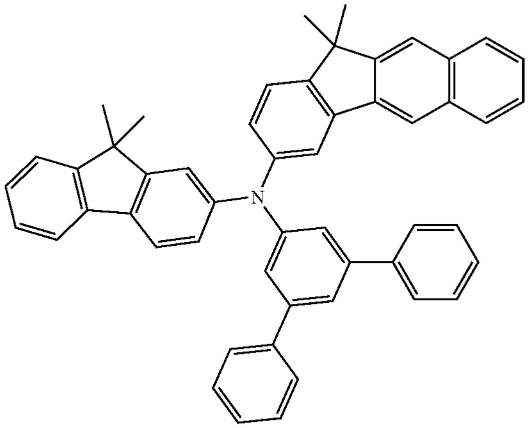 [SMILES: CC1(C)c2ccccc2-c2ccc(N(c3cc(-c4ccccc4)cc(-c4ccccc4)c3)c3ccc4c(c3)-c3cc5ccccc5cc3C4(C)C)cc21] | HT-3 |
| Light-Emitting Layer | 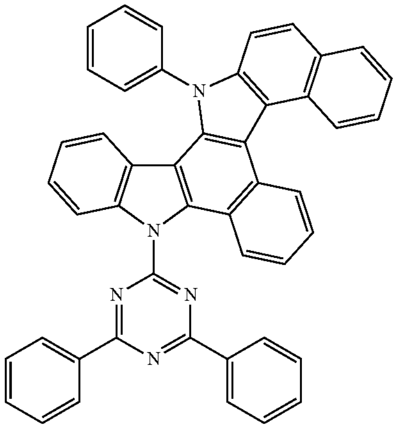 [SMILES: c1ccc(-c2nc(-c3ccccc3)nc(-n3c4ccccc4c4c3c3ccccc3c3c5c6ccccc6ccc5n(-c5ccccc5)c34)n2)cc1] | C1-61 |

TABLE 4-continued
C2-52
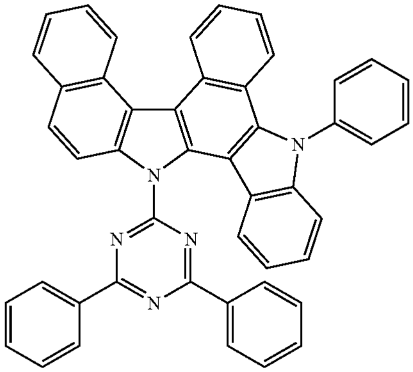 [SMILES: c1ccc(-c2nc(-c3ccccc3)nc(-n3c4ccc5ccccc5c4c4c5ccccc5c5c(c6ccccc6n5-c5ccccc5)c43)n2)cc1]
C1-65
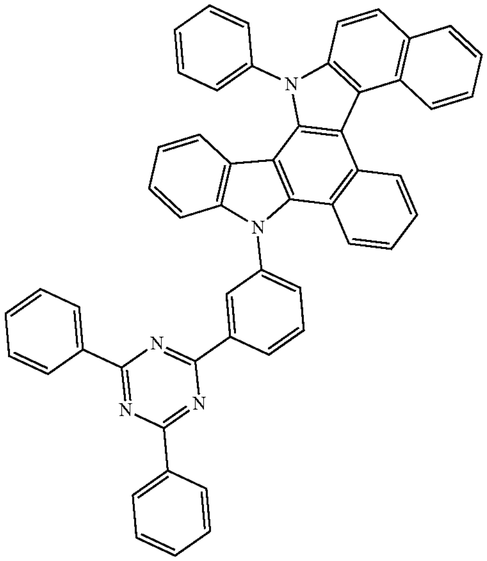 [SMILES: c1ccc(-c2nc(-c3ccccc3)nc(-c3cccc(-n4c5ccccc5c5c4c4ccccc4c4c6c7ccccc7ccc6n(-c6ccccc6)c45)c3)n2)cc1]
C1-69
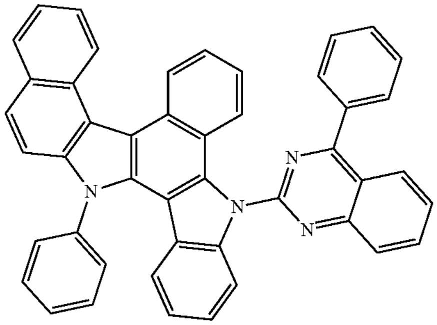 [SMILES: c1ccc(-c2nc(-n3c4ccccc4c4c3c3ccccc3c3c5c6ccccc6ccc5n(-c5ccccc5)c34)nc3ccccc23)cc1]
D-39
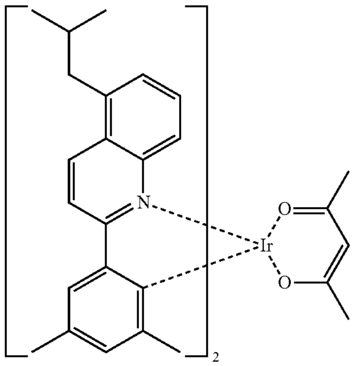

TABLE 4-continued
| | | |
|---|---|---|
| | 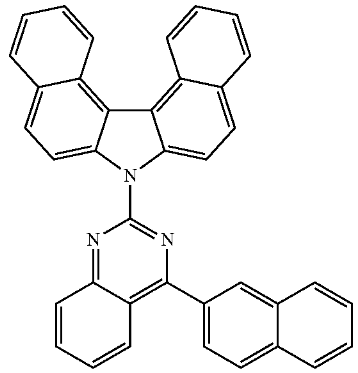 [SMILES: c1ccc2cc(-c3nc(-n4c5ccc6ccccc6c5c5c6ccccc6ccc54)nc4ccccc34)ccc2c1] | C |
| Light-Emitting Layer | 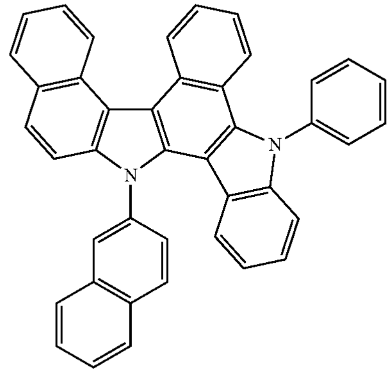 [SMILES: c1ccc(-n2c3ccccc3c3c2c2ccccc2c2c4c5ccccc5ccc4n(-c4ccc5ccccc5c4)c23)cc1] | C1-4 |
| | 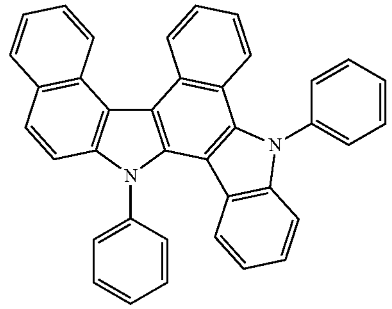 [SMILES: c1ccc(-n2c3ccccc3c3c2c2ccccc2c2c4c5ccccc5ccc4n(-c4ccccc4)c23)cc1] | C1-1 |
| | 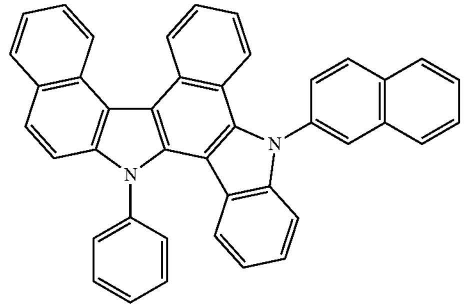 [SMILES: c1ccc(-n2c3ccc4ccccc4c3c3c4ccccc4c4c(c5ccccc5n4-c4ccc5ccccc5c4)c32)cc1] | C2-1 |

TABLE 4-continued
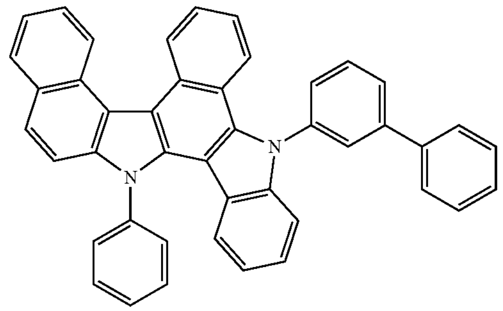 [SMILES: c1ccc(-c2cccc(-n3c4ccccc4c4c3c3ccccc3c3c5c6ccccc6ccc5n(-c5ccccc5)c34)c2)cc1]
C1-11
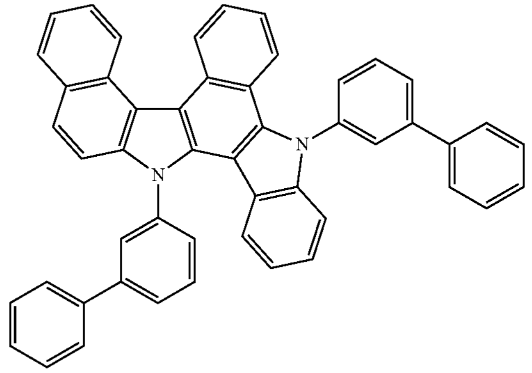 [SMILES: c1ccc(-c2cccc(-n3c4ccccc4c4c3c3ccccc3c3c5c6ccccc6ccc5n(-c5cccc(-c6ccccc6)c5)c34)c2)cc1]
C1-13
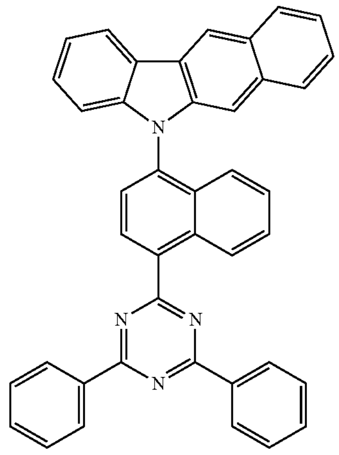 [SMILES: c1ccc(-c2nc(-c3ccccc3)nc(-c3ccc(-n4c5ccccc5c5cc6ccccc6cc54)c4ccccc34)n2)cc1]
H-207

TABLE 4-continued

| | | |
|---|---|---|
| | 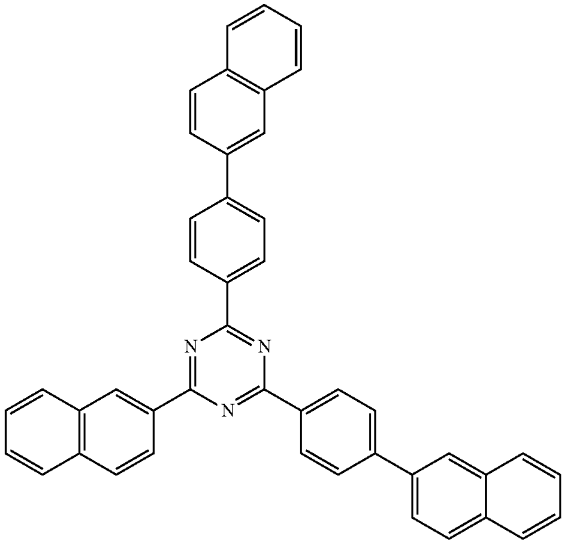 [SMILES: c1ccc2cc(-c3ccc(-c4nc(-c5ccc(-c6ccc7ccccc7c6)cc5)nc(-c5ccc6ccccc6c5)n4)cc3)ccc2c1] | H-201 |
| Electron Transport Layer/ Electron Injection Layer | 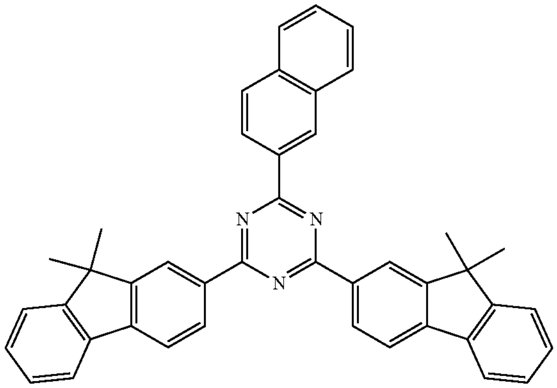 [SMILES: CC1(C)c2ccccc2-c2ccc(-c3nc(-c4ccc5c(c4)C(C)(C)c4ccccc4-5)nc(-c4ccc5ccccc5c4)n3)cc21] | ET-1 |
| | 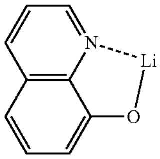 | EI-1 |

The invention claimed is:

1. An organic electroluminescent compound represented by the following formula 1:

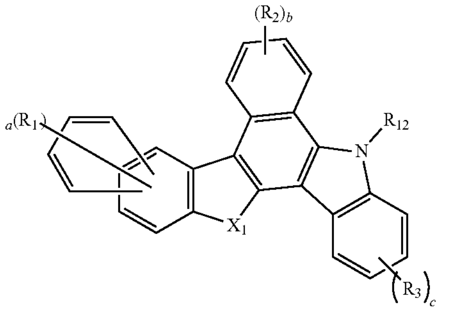

(1)

wherein $X_1$ represents $NR_{11}$;

$R_{11}$ and $R_{12}$, each independently, are represented by -L-Ar;

$R_1$ to $R_3$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or may be linked to an adjacent substituent to form a substituted or unsubstituted (3- to 30-membered) mono- or polycyclic ring;

Ar represents a substituted or unsubstituted (C6-C30)aryl, or a substituted or unsubstituted (3- to 30-membered) heteroaryl wherein the (3- to 30-membered)heteroaryl group is selected from the group consisting of furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyrazinyl, pyrimidinyl, pyridazinyl, benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl and dihydroacridinyl;

L represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene; and a represents an integer of 1 to 6, b and c, each independently, represent an integer of 1 to 4, where if a to c, each independently, are an integer of 2 or more, each of $R_1$ to $R_3$ may be the same or different.

2. The organic electroluminescent compound according to claim 1, wherein the substituents of the substituted (C1-C30)alkyl(ene), the substituted (C6-C30)aryl(ene), the substituted (3- to 30-membered)heteroaryl(ene), the substituted (C3-C30)cycloalkyl(ene), the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-C30)arylamino, and the substituted (3- to 30-membered) mono- or polycyclic ring in L, Ar, $R_1$ to $R_3$, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered) heteroaryl unsubstituted or substituted with a (C6-C30)aryl; a (C6-C30)aryl unsubstituted or substituted with a (5- to 30-membered)heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30) alkyl(C6-C30)arylboronyl; a (C6-C30)aryl(C1-C30)alkyl; and a (C1-C30)alkyl(C6-C30)aryl.

3. The organic electroluminescent compound according to claim 1, wherein formula 1 is represented by the following formula 2:

(2)

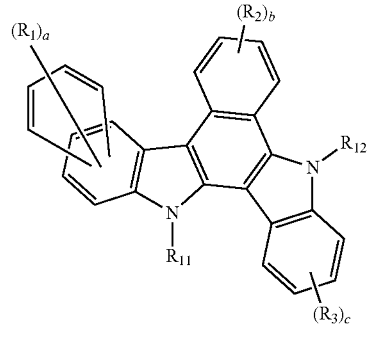

wherein $R_{11}$ and $R_{12}$, each independently, are represented by -L-Ar;

L represents a single bond, an unsubstituted (C6-C25) arylene, or an unsubstituted (5- to 25-membered)heteroarylene;

Ar represents a (C6-C25)aryl unsubstituted or substituted with a (C1-C10)alkyl or a cyano, or a (5- to 25-membered)heteroaryl unsubstituted or substituted with a (C6-C25)aryl wherein the (5- to 25-membered)heteroaryl group is selected from the group consisting of furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyrazinyl, pyrimidinyl, pyridazinyl, benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl and dihydroacridinyl;

$R_1$ to $R_3$, each independently, represent an unsubstituted (C6-C25)aryl; and a, b, and c, each independently, represent 0 or 1.

4. The organic electroluminescent compound according to claim 1, wherein formula 1 is represented by any one of the following formulas 4 to 6:

(4)

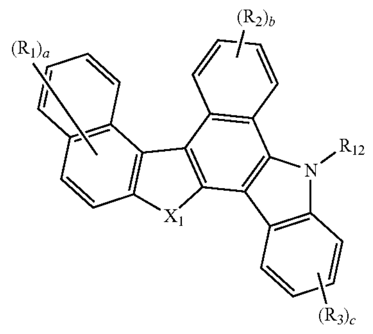

(5)

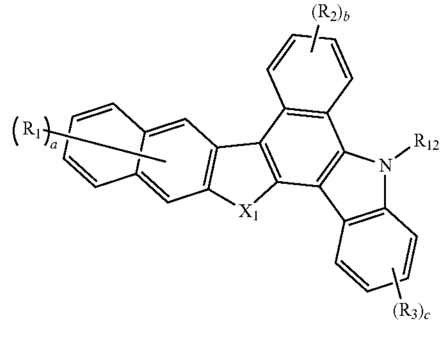

-continued (6)

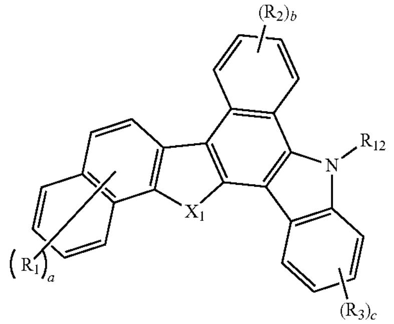

wherein $X_1$, $R_{11}$, and $R_{12}$ are as defined in claim 1;

L represents a single bond, an unsubstituted (C6-C18) arylene, or an unsubstituted (5- to 20-membered)heteroarylene;

Ar represents a (C6-C18)aryl unsubstituted or substituted with a (C1-C6)alkyl or a cyano, or a (5- to 20-membered)heteroaryl unsubstituted or substituted with a (C6-C18)aryl wherein the (5- to 20-membered)heteroaryl group is selected from the group consisting of furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyrazinyl, pyrimidinyl, pyridazinyl, benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl and dihydroacridinyl;

$R_1$ to $R_3$, each independently, represent an unsubstituted (C6-C18)aryl; and a, b, and c, each independently, represent 0 or 1.

5. The organic electroluminescent compound according to claim 1, wherein formula 1 is represented by any one of the following formulas 7 to 11:

(7)

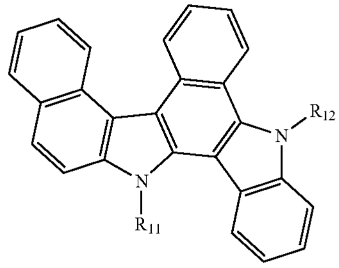

-continued (8)

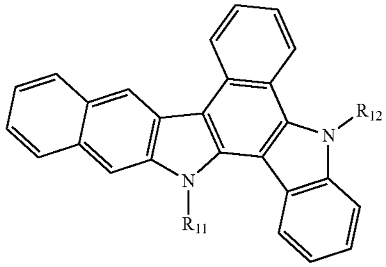

(9)

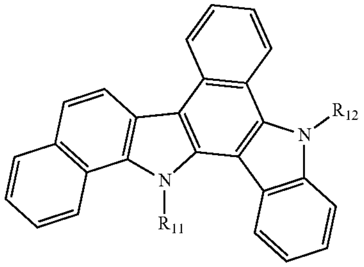

(10)

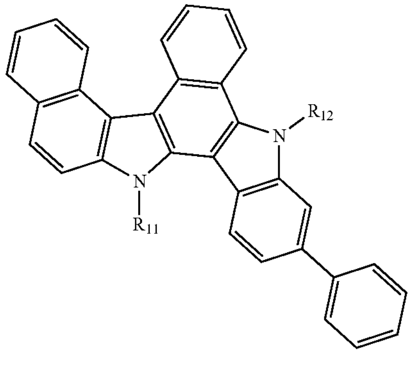

(11)

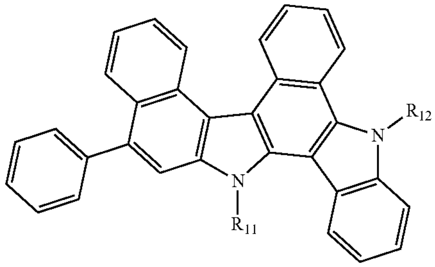

wherein, $R_{11}$ and $R_{12}$ are as defined in claim 1.

6. The organic electroluminescent compound according to claim 5, wherein the compound represented by formula 1 is any one selected from the following compounds C1-1 to C1-96, C2-1 to C2-54, C2-56 to C2-58, C2-60 to C2-62, C2-64 to C2-66, C2-68 to C2-70, C2-72 to C2-74, C2-76 to C2-78, C2-80 to C2-82, C2-84 to C2-86, C3-1 to C3-66, C4-1 to C4-33, C4-35 to C4-37, C4-39 to C4-41, C4-43 to C4-45, C4-47 to C4-49, C4-51 to C4-53, C4-55 to C4-57, C4-59 to C4-61, C4-63 to C4-65, C5-1 to C5-66, C6-1 to C6-33, C6-35 to C6-37, C6-39 to C6-41, C6-43 to C6-45, C6-47 to C6-49, C6-51 to C6-53, C6-55 to C6-57, C6-59 to C6-61 and C6-63 to C6-65:

| Compound | Formula | $R_{11}$ | $R_{12}$ | Compound | Formula | $R_{11}$ | $R_{12}$ |
|---|---|---|---|---|---|---|---|
| C1-1 | 7 | $R_{aa}$ | $R_{aa}$ | C1-2 | 7 | $R_{ab}$ | $R_{aa}$ |
| C1-3 | 7 | $R_{ac}$ | $R_{aa}$ | C1-4 | 7 | $R_{ad}$ | $R_{aa}$ |
| C1-5 | 7 | $R_{ae}$ | $R_{aa}$ | C1-6 | 7 | $R_{aa}$ | $R_{ab}$ |
| C1-7 | 7 | $R_{ab}$ | $R_{ab}$ | C1-8 | 7 | $R_{ac}$ | $R_{ab}$ |
| C1-9 | 7 | $R_{ad}$ | $R_{ab}$ | C1-10 | 7 | $R_{ae}$ | $R_{ab}$ |
| C1-11 | 7 | $R_{aa}$ | $R_{ac}$ | C1-12 | 7 | $R_{ab}$ | $R_{ac}$ |
| C1-13 | 7 | $R_{ac}$ | $R_{ac}$ | C1-14 | 7 | $R_{ad}$ | $R_{ac}$ |
| C1-15 | 7 | $R_{ae}$ | $R_{ac}$ | C1-16 | 7 | $R_{aa}$ | $R_{af}$ |
| C1-17 | 7 | $R_{ab}$ | $R_{af}$ | C1-18 | 7 | $R_{ac}$ | $R_{af}$ |
| C1-19 | 7 | $R_{ad}$ | $R_{af}$ | C1-20 | 7 | $R_{ae}$ | $R_{af}$ |
| C1-21 | 7 | $R_{aa}$ | $R_{ag}$ | C1-22 | 7 | $R_{ab}$ | $R_{ag}$ |
| C1-23 | 7 | $R_{ac}$ | $R_{ag}$ | C1-24 | 7 | $R_{ad}$ | $R_{ag}$ |
| C1-25 | 7 | $R_{ae}$ | $R_{ag}$ | C1-26 | 7 | $R_{aa}$ | $R_{ah}$ |
| C1-27 | 7 | $R_{ab}$ | $R_{ah}$ | C1-28 | 7 | $R_{ac}$ | $R_{ah}$ |
| C1-29 | 7 | $R_{ad}$ | $R_{ah}$ | C1-30 | 7 | $R_{ae}$ | $R_{ah}$ |
| C1-31 | 7 | $R_{aa}$ | $R_{ai}$ | C1-32 | 7 | $R_{ab}$ | $R_{ai}$ |
| C1-33 | 7 | $R_{ac}$ | $R_{ai}$ | C1-34 | 7 | $R_{ad}$ | $R_{ai}$ |
| C1-35 | 7 | $R_{ae}$ | $R_{ai}$ | C1-36 | 7 | $R_{aa}$ | $R_{aj}$ |
| C1-37 | 7 | $R_{ab}$ | $R_{aj}$ | C1-38 | 7 | $R_{ac}$ | $R_{aj}$ |
| C1-39 | 7 | $R_{ad}$ | $R_{aj}$ | C1-40 | 7 | $R_{ae}$ | $R_{aj}$ |
| C1-41 | 7 | $R_{aa}$ | $R_{ak}$ | C1-42 | 7 | $R_{ab}$ | $R_{ak}$ |
| C1-43 | 7 | $R_{ac}$ | $R_{ak}$ | C1-44 | 7 | $R_{ad}$ | $R_{ak}$ |
| C1-45 | 7 | $R_{ae}$ | $R_{ak}$ | C1-46 | 7 | $R_{aa}$ | $R_{al}$ |
| C1-47 | 7 | $R_{ab}$ | $R_{al}$ | C1-48 | 7 | $R_{ac}$ | $R_{al}$ |
| C1-49 | 7 | $R_{ad}$ | $R_{al}$ | C1-50 | 7 | $R_{ae}$ | $R_{al}$ |
| C1-51 | 7 | $R_{aa}$ | $R_{am}$ | C1-52 | 7 | $R_{ab}$ | $R_{am}$ |
| C1-53 | 7 | $R_{ac}$ | $R_{am}$ | C1-54 | 7 | $R_{ad}$ | $R_{am}$ |
| C1-55 | 7 | $R_{ae}$ | $R_{am}$ | C1-56 | 7 | $R_{aa}$ | $R_{an}$ |
| C1-57 | 7 | $R_{ab}$ | $R_{an}$ | C1-58 | 7 | $R_{ac}$ | $R_{an}$ |
| C1-59 | 7 | $R_{ad}$ | $R_{an}$ | C1-60 | 7 | $R_{ae}$ | $R_{an}$ |
| C1-61 | 7 | $R_{aa}$ | $R_{ao}$ | C1-62 | 7 | $R_{ab}$ | $R_{ao}$ |
| C1-63 | 7 | $R_{ak}$ | $R_{ao}$ | C1-64 | 7 | $R_{an}$ | $R_{ao}$ |
| C1-65 | 7 | $R_{aa}$ | $R_{ap}$ | C1-66 | 7 | $R_{ab}$ | $R_{ap}$ |
| C1-67 | 7 | $R_{ak}$ | $R_{ap}$ | C1-68 | 7 | $R_{an}$ | $R_{ap}$ |
| C1-69 | 7 | $R_{aa}$ | $R_{aq}$ | C1-70 | 7 | $R_{ab}$ | $R_{aq}$ |
| C1-71 | 7 | $R_{ak}$ | $R_{aq}$ | C1-72 | 7 | $R_{an}$ | $R_{aq}$ |
| C1-73 | 7 | $R_{aa}$ | $R_{ar}$ | C1-74 | 7 | $R_{ab}$ | $R_{ar}$ |
| C1-75 | 7 | $R_{ak}$ | $R_{ar}$ | C1-76 | 7 | $R_{an}$ | $R_{ar}$ |
| C1-77 | 7 | $R_{aa}$ | $R_{as}$ | C1-78 | 7 | $R_{ab}$ | $R_{as}$ |
| C1-79 | 7 | $R_{ak}$ | $R_{as}$ | C1-80 | 7 | $R_{an}$ | $R_{as}$ |
| C1-81 | 7 | $R_{aa}$ | $R_{at}$ | C1-82 | 7 | $R_{ab}$ | $R_{at}$ |
| C1-83 | 7 | $R_{ak}$ | $R_{at}$ | C1-84 | 7 | $R_{an}$ | $R_{at}$ |
| C1-85 | 7 | $R_{aa}$ | $R_{au}$ | C1-86 | 7 | $R_{ab}$ | $R_{au}$ |
| C1-87 | 7 | $R_{ak}$ | $R_{au}$ | C1-88 | 7 | $R_{an}$ | $R_{au}$ |
| C1-89 | 7 | $R_{aa}$ | $R_{av}$ | C1-90 | 7 | $R_{ab}$ | $R_{av}$ |
| C1-91 | 7 | $R_{ak}$ | $R_{av}$ | C1-92 | 7 | $R_{an}$ | $R_{av}$ |
| C1-93 | 7 | $R_{aa}$ | $R_{aw}$ | C1-94 | 7 | $R_{ab}$ | $R_{aw}$ |
| C1-95 | 7 | $R_{ak}$ | $R_{aw}$ | C1-96 | 7 | $R_{an}$ | $R_{aw}$ |
| C2-1 | 7 | $R_{aa}$ | $R_{ad}$ | C2-2 | 7 | $R_{aa}$ | $R_{ae}$ |
| C2-3 | 7 | $R_{ab}$ | $R_{ad}$ | C2-4 | 7 | $R_{ab}$ | $R_{ae}$ |
| C2-5 | 7 | $R_{ac}$ | $R_{ad}$ | C2-6 | 7 | $R_{ac}$ | $R_{ae}$ |
| C2-7 | 7 | $R_{af}$ | $R_{aa}$ | C2-8 | 7 | $R_{af}$ | $R_{ab}$ |
| C2-9 | 7 | $R_{af}$ | $R_{ac}$ | C2-10 | 7 | $R_{af}$ | $R_{ad}$ |
| C2-11 | 7 | $R_{af}$ | $R_{ae}$ | C2-12 | 7 | $R_{ag}$ | $R_{aa}$ |
| C2-13 | 7 | $R_{ag}$ | $R_{ab}$ | C2-14 | 7 | $R_{ag}$ | $R_{ac}$ |
| C2-15 | 7 | $R_{ag}$ | $R_{ad}$ | C2-16 | 7 | $R_{ag}$ | $R_{ae}$ |
| C2-17 | 7 | $R_{ah}$ | $R_{aa}$ | C2-18 | 7 | $R_{ah}$ | $R_{ab}$ |
| C2-19 | 7 | $R_{ah}$ | $R_{ac}$ | C2-20 | 7 | $R_{ah}$ | $R_{ad}$ |
| C2-21 | 7 | $R_{ah}$ | $R_{ae}$ | C2-22 | 7 | $R_{ai}$ | $R_{aa}$ |
| C2-23 | 7 | $R_{ai}$ | $R_{ab}$ | C2-24 | 7 | $R_{ai}$ | $R_{ac}$ |
| C2-25 | 7 | $R_{ai}$ | $R_{ad}$ | C2-26 | 7 | $R_{ai}$ | $R_{ae}$ |
| C2-27 | 7 | $R_{aj}$ | $R_{aa}$ | C2-28 | 7 | $R_{aj}$ | $R_{ab}$ |
| C2-29 | 7 | $R_{aj}$ | $R_{ac}$ | C2-30 | 7 | $R_{aj}$ | $R_{ad}$ |
| C2-31 | 7 | $R_{aj}$ | $R_{ae}$ | C2-32 | 7 | $R_{ak}$ | $R_{aa}$ |
| C2-33 | 7 | $R_{ak}$ | $R_{ab}$ | C2-34 | 7 | $R_{ak}$ | $R_{ac}$ |
| C2-35 | 7 | $R_{ak}$ | $R_{ad}$ | C2-36 | 7 | $R_{ak}$ | $R_{ae}$ |
| C2-37 | 7 | $R_{al}$ | $R_{aa}$ | C2-38 | 7 | $R_{al}$ | $R_{ab}$ |
| C2-39 | 7 | $R_{al}$ | $R_{ac}$ | C2-40 | 7 | $R_{al}$ | $R_{ad}$ |
| C2-41 | 7 | $R_{al}$ | $R_{ae}$ | C2-42 | 7 | $R_{am}$ | $R_{aa}$ |
| C2-43 | 7 | $R_{am}$ | $R_{ab}$ | C2-44 | 7 | $R_{am}$ | $R_{ac}$ |
| C2-45 | 7 | $R_{am}$ | $R_{ad}$ | C2-46 | 7 | $R_{am}$ | $R_{ae}$ |
| C2-47 | 7 | $R_{an}$ | $R_{aa}$ | C2-48 | 7 | $R_{an}$ | $R_{ab}$ |
| C2-49 | 7 | $R_{an}$ | $R_{ac}$ | C2-50 | 7 | $R_{an}$ | $R_{ad}$ |
| C2-51 | 7 | $R_{an}$ | $R_{ae}$ | C2-52 | 7 | $R_{ao}$ | $R_{aa}$ |
| C2-53 | 7 | $R_{ao}$ | $R_{ad}$ | C2-54 | 7 | $R_{ao}$ | $R_{ae}$ |
| | | | | C2-56 | 7 | $R_{ap}$ | $R_{aa}$ |
| C2-57 | 7 | $R_{ap}$ | $R_{ad}$ | C2-58 | 7 | $R_{ap}$ | $R_{ae}$ |
| | | | | C2-60 | 7 | $R_{aq}$ | $R_{aa}$ |

-continued

| Compound | Formula | $R_{11}$ | $R_{12}$ | Compound | Formula | $R_{11}$ | $R_{12}$ |
|---|---|---|---|---|---|---|---|
| C2-61 | 7 | $R_{aq}$ | $R_{ad}$ | C2-62 | 7 | $R_{aq}$ | $R_{ae}$ |
| | | | | C2-64 | 7 | $R_{ar}$ | $R_{aa}$ |
| C2-65 | 7 | $R_{ar}$ | $R_{ad}$ | C2-66 | 7 | $R_{ar}$ | $R_{ae}$ |
| | | | | C2-68 | 7 | $R_{as}$ | $R_{aa}$ |
| C2-69 | 7 | $R_{as}$ | $R_{ad}$ | C2-70 | 7 | $R_{as}$ | $R_{ae}$ |
| | | | | C2-72 | 7 | $R_{at}$ | $R_{aa}$ |
| C2-73 | 7 | $R_{at}$ | $R_{ad}$ | C2-74 | 7 | $R_{at}$ | $R_{ae}$ |
| | | | | C2-76 | 7 | $R_{au}$ | $R_{aa}$ |
| C2-77 | 7 | $R_{au}$ | $R_{ad}$ | C2-78 | 7 | $R_{au}$ | $R_{ae}$ |
| | | | | C2-80 | 7 | $R_{av}$ | $R_{aa}$ |
| C2-81 | 7 | $R_{av}$ | $R_{ad}$ | C2-82 | 7 | $R_{av}$ | $R_{ae}$ |
| | | | | C2-84 | 7 | $R_{aw}$ | $R_{aa}$ |
| C2-85 | 7 | $R_{aw}$ | $R_{ad}$ | C2-86 | 7 | $R_{aw}$ | $R_{ae}$ |
| | | | | — | — | — | — |
| C3-1 | 8 | $R_{aa}$ | $R_{aa}$ | C3-2 | 8 | $R_{ac}$ | $R_{aa}$ |
| C3-3 | 8 | $R_{ad}$ | $R_{aa}$ | C3-4 | 8 | $R_{ay}$ | $R_{aa}$ |
| C3-5 | 8 | $R_{am}$ | $R_{aa}$ | C3-6 | 8 | $R_{aa}$ | $R_{ab}$ |
| C3-7 | 8 | $R_{ac}$ | $R_{ab}$ | C3-8 | 8 | $R_{ad}$ | $R_{ab}$ |
| C3-9 | 8 | $R_{ay}$ | $R_{ab}$ | C3-10 | 8 | $R_{am}$ | $R_{ab}$ |
| C3-11 | 8 | $R_{aa}$ | $R_{ac}$ | C3-12 | 8 | $R_{ac}$ | $R_{ac}$ |
| C3-13 | 8 | $R_{ad}$ | $R_{ac}$ | C3-14 | 8 | $R_{ay}$ | $R_{ac}$ |
| C3-15 | 8 | $R_{am}$ | $R_{ac}$ | C3-16 | 8 | $R_{aa}$ | $R_{ak}$ |
| C3-17 | 8 | $R_{ac}$ | $R_{ak}$ | C3-18 | 8 | $R_{ad}$ | $R_{ak}$ |
| C3-19 | 8 | $R_{ay}$ | $R_{ak}$ | C3-20 | 8 | $R_{am}$ | $R_{ak}$ |
| C3-21 | 8 | $R_{aa}$ | $R_{az}$ | C3-22 | 8 | $R_{ac}$ | $R_{az}$ |
| C3-23 | 8 | $R_{ad}$ | $R_{az}$ | C3-24 | 8 | $R_{ay}$ | $R_{az}$ |
| C3-25 | 8 | $R_{am}$ | $R_{az}$ | C3-26 | 8 | $R_{aa}$ | $R_{ae}$ |
| C3-27 | 8 | $R_{ac}$ | $R_{ae}$ | C3-28 | 8 | $R_{ad}$ | $R_{ae}$ |
| C3-29 | 8 | $R_{ay}$ | $R_{ae}$ | C3-30 | 8 | $R_{am}$ | $R_{ae}$ |
| C3-31 | 8 | $R_{aa}$ | $R_{ao}$ | C3-32 | 8 | $R_{ab}$ | $R_{ao}$ |
| C3-33 | 8 | $R_{ak}$ | $R_{ao}$ | C3-34 | 8 | $R_{an}$ | $R_{ao}$ |
| C3-35 | 8 | $R_{aa}$ | $R_{ap}$ | C3-36 | 8 | $R_{ab}$ | $R_{ap}$ |
| C3-37 | 8 | $R_{ak}$ | $R_{ap}$ | C3-38 | 8 | $R_{an}$ | $R_{ap}$ |
| C3-39 | 8 | $R_{aa}$ | $R_{aq}$ | C3-40 | 8 | $R_{ab}$ | $R_{aq}$ |
| C3-41 | 8 | $R_{ak}$ | $R_{aq}$ | C3-42 | 8 | $R_{an}$ | $R_{aq}$ |
| C3-43 | 8 | $R_{aa}$ | $R_{ar}$ | C3-44 | 8 | $R_{ab}$ | $R_{ar}$ |
| C3-45 | 8 | $R_{ak}$ | $R_{ar}$ | C3-46 | 8 | $R_{an}$ | $R_{ar}$ |
| C3-47 | 8 | $R_{aa}$ | $R_{as}$ | C3-48 | 8 | $R_{ab}$ | $R_{as}$ |
| C3-49 | 8 | $R_{ak}$ | $R_{as}$ | C3-50 | 8 | $R_{an}$ | $R_{as}$ |
| C3-51 | 8 | $R_{aa}$ | $R_{at}$ | C3-52 | 8 | $R_{ab}$ | $R_{at}$ |
| C3-53 | 8 | $R_{ak}$ | $R_{at}$ | C3-54 | 8 | $R_{an}$ | $R_{at}$ |
| C3-55 | 8 | $R_{aa}$ | $R_{au}$ | C3-56 | 8 | $R_{ab}$ | $R_{au}$ |
| C3-57 | 8 | $R_{ak}$ | $R_{au}$ | C3-58 | 8 | $R_{an}$ | $R_{au}$ |
| C3-59 | 8 | $R_{aa}$ | $R_{av}$ | C3-60 | 8 | $R_{ab}$ | $R_{av}$ |
| C3-61 | 8 | $R_{ak}$ | $R_{av}$ | C3-62 | 8 | $R_{an}$ | $R_{av}$ |
| C3-63 | 8 | $R_{aa}$ | $R_{aw}$ | C3-64 | 8 | $R_{ab}$ | $R_{aw}$ |
| C3-65 | 8 | $R_{ak}$ | $R_{aw}$ | C3-66 | 8 | $R_{an}$ | $R_{aw}$ |
| C4-1 | 9 | $R_{aa}$ | $R_{aa}$ | C4-2 | 9 | $R_{ab}$ | $R_{aa}$ |
| C4-3 | 9 | $R_{ad}$ | $R_{aa}$ | C4-4 | 9 | $R_{ay}$ | $R_{aa}$ |
| C4-5 | 9 | $R_{am}$ | $R_{aa}$ | C4-6 | 9 | $R_{aa}$ | $R_{ab}$ |
| C4-7 | 9 | $R_{ab}$ | $R_{ab}$ | C4-8 | 9 | $R_{ad}$ | $R_{ab}$ |
| C4-9 | 9 | $R_{ay}$ | $R_{ab}$ | C4-10 | 9 | $R_{am}$ | $R_{ab}$ |
| C4-11 | 9 | $R_{aa}$ | $R_{ac}$ | C4-12 | 9 | $R_{ab}$ | $R_{ac}$ |
| C4-13 | 9 | $R_{ad}$ | $R_{ac}$ | C4-14 | 9 | $R_{ay}$ | $R_{ac}$ |
| C4-15 | 9 | $R_{am}$ | $R_{ac}$ | C4-16 | 9 | $R_{aa}$ | $R_{ak}$ |
| C4-17 | 9 | $R_{ab}$ | $R_{ak}$ | C4-18 | 9 | $R_{ad}$ | $R_{ak}$ |
| C4-19 | 9 | $R_{ay}$ | $R_{ak}$ | C4-20 | 9 | $R_{am}$ | $R_{ak}$ |
| C4-21 | 9 | $R_{aa}$ | $R_{az}$ | C4-22 | 9 | $R_{ab}$ | $R_{az}$ |
| C4-23 | 9 | $R_{ad}$ | $R_{az}$ | C4-24 | 9 | $R_{ay}$ | $R_{az}$ |
| C4-25 | 9 | $R_{am}$ | $R_{az}$ | C4-26 | 9 | $R_{aa}$ | $R_{ae}$ |
| C4-27 | 9 | $R_{ab}$ | $R_{ae}$ | C4-28 | 9 | $R_{ad}$ | $R_{ae}$ |
| C4-29 | 9 | $R_{ay}$ | $R_{ae}$ | C4-30 | 9 | $R_{am}$ | $R_{ae}$ |
| C4-31 | 9 | $R_{aa}$ | $R_{ao}$ | C4-32 | 9 | $R_{ad}$ | $R_{ao}$ |
| C4-33 | 9 | $R_{ae}$ | $R_{ao}$ | | | | |
| C4-35 | 9 | $R_{aa}$ | $R_{ap}$ | C4-36 | 9 | $R_{ad}$ | $R_{ap}$ |
| C4-37 | 9 | $R_{ae}$ | $R_{ap}$ | | | | |
| C4-39 | 9 | $R_{aa}$ | $R_{aq}$ | C4-40 | 9 | $R_{ad}$ | $R_{aq}$ |
| C4-41 | 9 | $R_{ae}$ | $R_{aq}$ | | | | |
| C4-43 | 9 | $R_{aa}$ | $R_{ar}$ | C4-44 | 9 | $R_{ad}$ | $R_{ar}$ |
| C4-45 | 9 | $R_{ae}$ | $R_{ar}$ | | | | |
| C4-47 | 9 | $R_{aa}$ | $R_{as}$ | C4-48 | 9 | $R_{ad}$ | $R_{as}$ |
| C4-49 | 9 | $R_{ae}$ | $R_{as}$ | | | | |
| C4-51 | 9 | $R_{aa}$ | $R_{at}$ | C4-52 | 9 | $R_{ad}$ | $R_{at}$ |
| C4-53 | 9 | $R_{ae}$ | $R_{at}$ | | | | |
| C4-55 | 9 | $R_{aa}$ | $R_{au}$ | C4-56 | 9 | $R_{ad}$ | $R_{au}$ |
| C4-57 | 9 | $R_{ae}$ | $R_{au}$ | | | | |

-continued

| Compound | Formula | $R_{11}$ | $R_{12}$ | Compound | Formula | $R_{11}$ | $R_{12}$ |
|---|---|---|---|---|---|---|---|
| C4-59 | 9 | $R_{aa}$ | $R_{av}$ | C4-60 | 9 | $R_{ad}$ | $R_{av}$ |
| C4-61 | 9 | $R_{ae}$ | $R_{av}$ | | | | |
| C4-63 | 9 | $R_{aa}$ | $R_{aw}$ | C4-64 | 9 | $R_{ad}$ | $R_{aw}$ |
| C4-65 | 9 | $R_{ae}$ | $R_{aw}$ | | | | |
| C5-1 | 10 | $R_{aa}$ | $R_{aa}$ | C5-2 | 10 | $R_{ab}$ | $R_{aa}$ |
| C5-3 | 10 | $R_{ad}$ | $R_{aa}$ | C5-4 | 10 | $R_{ay}$ | $R_{aa}$ |
| C5-5 | 10 | $R_{am}$ | $R_{aa}$ | C5-6 | 10 | $R_{aa}$ | $R_{ab}$ |
| C5-7 | 10 | $R_{ab}$ | $R_{ab}$ | C5-8 | 10 | $R_{ad}$ | $R_{ab}$ |
| C5-9 | 10 | $R_{ay}$ | $R_{ab}$ | C5-10 | 10 | $R_{am}$ | $R_{ab}$ |
| C5-11 | 10 | $R_{aa}$ | $R_{ac}$ | C5-12 | 10 | $R_{ab}$ | $R_{ac}$ |
| C5-13 | 10 | $R_{ad}$ | $R_{ac}$ | C5-14 | 10 | $R_{ay}$ | $R_{ac}$ |
| C5-15 | 10 | $R_{am}$ | $R_{ac}$ | C5-16 | 10 | $R_{aa}$ | $R_{ak}$ |
| C5-17 | 10 | $R_{ab}$ | $R_{ak}$ | C5-18 | 10 | $R_{ad}$ | $R_{ak}$ |
| C5-19 | 10 | $R_{ay}$ | $R_{ak}$ | C5-20 | 10 | $R_{am}$ | $R_{ak}$ |
| C5-21 | 10 | $R_{aa}$ | $R_{an}$ | C5-22 | 10 | $R_{ab}$ | $R_{an}$ |
| C5-23 | 10 | $R_{ad}$ | $R_{an}$ | C5-24 | 10 | $R_{ay}$ | $R_{an}$ |
| C5-25 | 10 | $R_{am}$ | $R_{an}$ | C5-26 | 10 | $R_{aa}$ | $R_{ae}$ |
| C5-27 | 10 | $R_{ab}$ | $R_{ae}$ | C5-28 | 10 | $R_{ad}$ | $R_{ae}$ |
| C5-29 | 10 | $R_{ay}$ | $R_{ae}$ | C5-30 | 10 | $R_{am}$ | $R_{ae}$ |
| C5-31 | 10 | $R_{aa}$ | $R_{ao}$ | C5-32 | 10 | $R_{ab}$ | $R_{ao}$ |
| C5-33 | 10 | $R_{ak}$ | $R_{ao}$ | C5-34 | 10 | $R_{an}$ | $R_{ao}$ |
| C5-35 | 10 | $R_{aa}$ | $R_{ap}$ | C5-36 | 10 | $R_{ab}$ | $R_{ap}$ |
| C5-37 | 10 | $R_{ak}$ | $R_{ap}$ | C5-38 | 10 | $R_{an}$ | $R_{ap}$ |
| C5-39 | 10 | $R_{aa}$ | $R_{aq}$ | C5-40 | 10 | $R_{ab}$ | $R_{aq}$ |
| C5-41 | 10 | $R_{ak}$ | $R_{aq}$ | C5-42 | 10 | $R_{an}$ | $R_{aq}$ |
| C5-43 | 10 | $R_{aa}$ | $R_{ar}$ | C5-44 | 10 | $R_{ab}$ | $R_{ar}$ |
| C5-45 | 10 | $R_{ak}$ | $R_{ar}$ | C5-46 | 10 | $R_{an}$ | $R_{ar}$ |
| C5-47 | 10 | $R_{aa}$ | $R_{as}$ | C5-48 | 10 | $R_{ab}$ | $R_{as}$ |
| C5-49 | 10 | $R_{ak}$ | $R_{as}$ | C5-50 | 10 | $R_{an}$ | $R_{as}$ |
| C5-51 | 10 | $R_{aa}$ | $R_{at}$ | C5-52 | 10 | $R_{ab}$ | $R_{at}$ |
| C5-53 | 10 | $R_{ak}$ | $R_{at}$ | C5-54 | 10 | $R_{an}$ | $R_{at}$ |
| C5-55 | 10 | $R_{aa}$ | $R_{au}$ | C5-56 | 10 | $R_{ab}$ | $R_{au}$ |
| C5-57 | 10 | $R_{ak}$ | $R_{au}$ | C5-58 | 10 | $R_{an}$ | $R_{au}$ |
| C5-59 | 10 | $R_{aa}$ | $R_{av}$ | C5-60 | 10 | $R_{ab}$ | $R_{av}$ |
| C5-61 | 10 | $R_{ak}$ | $R_{av}$ | C5-62 | 10 | $R_{an}$ | $R_{av}$ |
| C5-63 | 10 | $R_{aa}$ | $R_{aw}$ | C5-64 | 10 | $R_{ab}$ | $R_{aw}$ |
| C5-65 | 10 | $R_{ak}$ | $R_{aw}$ | C5-66 | 10 | $R_{an}$ | $R_{aw}$ |
| C6-1 | 11 | $R_{aa}$ | $R_{aa}$ | C6-2 | 11 | $R_{ac}$ | $R_{aa}$ |
| C6-3 | 11 | $R_{ad}$ | $R_{aa}$ | C6-4 | 11 | $R_{ay}$ | $R_{aa}$ |
| C6-5 | 11 | $R_{am}$ | $R_{aa}$ | C6-6 | 11 | $R_{aa}$ | $R_{ab}$ |
| C6-7 | 11 | $R_{ac}$ | $R_{ab}$ | C6-8 | 11 | $R_{ad}$ | $R_{ab}$ |
| C6-9 | 11 | $R_{ay}$ | $R_{ab}$ | C6-10 | 11 | $R_{am}$ | $R_{ab}$ |
| C6-11 | 11 | $R_{aa}$ | $R_{ac}$ | C6-12 | 11 | $R_{ac}$ | $R_{ac}$ |
| C6-13 | 11 | $R_{ad}$ | $R_{ac}$ | C6-14 | 11 | $R_{ay}$ | $R_{ac}$ |
| C6-15 | 11 | $R_{am}$ | $R_{ac}$ | C6-16 | 11 | $R_{aa}$ | $R_{ak}$ |
| C6-17 | 11 | $R_{ac}$ | $R_{ak}$ | C6-18 | 11 | $R_{ad}$ | $R_{ak}$ |
| C6-19 | 11 | $R_{ay}$ | $R_{ak}$ | C6-20 | 11 | $R_{am}$ | $R_{ak}$ |
| C6-21 | 11 | $R_{aa}$ | $R_{az}$ | C6-22 | 11 | $R_{ac}$ | $R_{az}$ |
| C6-23 | 11 | $R_{ad}$ | $R_{az}$ | C6-24 | 11 | $R_{ay}$ | $R_{az}$ |
| C6-25 | 11 | $R_{am}$ | $R_{az}$ | C6-26 | 11 | $R_{aa}$ | $R_{ae}$ |
| C6-27 | 11 | $R_{ac}$ | $R_{ae}$ | C6-28 | 11 | $R_{ad}$ | $R_{ae}$ |
| C6-29 | 11 | $R_{ay}$ | $R_{ae}$ | C6-30 | 11 | $R_{am}$ | $R_{ae}$ |
| C6-31 | 11 | $R_{aa}$ | $R_{ao}$ | C6-32 | 11 | $R_{ad}$ | $R_{ao}$ |
| C6-33 | 11 | $R_{ae}$ | $R_{ao}$ | | | | |
| C6-35 | 11 | $R_{aa}$ | $R_{ap}$ | C6-36 | 11 | $R_{ad}$ | $R_{ap}$ |
| C6-37 | 11 | $R_{ae}$ | $R_{ap}$ | | | | |
| C6-39 | 11 | $R_{aa}$ | $R_{aq}$ | C6-40 | 11 | $R_{ad}$ | $R_{aq}$ |
| C6-41 | 11 | $R_{ae}$ | $R_{aq}$ | | | | |
| C6-43 | 11 | $R_{aa}$ | $R_{ar}$ | C6-44 | 11 | $R_{ad}$ | $R_{ar}$ |
| C6-45 | 11 | $R_{ae}$ | $R_{ar}$ | | | | |
| C6-47 | 11 | $R_{aa}$ | $R_{as}$ | C6-48 | 11 | $R_{ad}$ | $R_{as}$ |
| C6-49 | 11 | $R_{ae}$ | $R_{as}$ | | | | |
| C6-51 | 11 | $R_{aa}$ | $R_{at}$ | C6-52 | 11 | $R_{ad}$ | $R_{at}$ |
| C6-53 | 11 | $R_{ae}$ | $R_{at}$ | | | | |
| C6-55 | 11 | $R_{aa}$ | $R_{au}$ | C6-56 | 11 | $R_{ad}$ | $R_{au}$ |
| C6-57 | 11 | $R_{ae}$ | $R_{au}$ | | | | |
| C6-59 | 11 | $R_{aa}$ | $R_{av}$ | C6-60 | 11 | $R_{ad}$ | $R_{av}$ |
| C6-61 | 11 | $R_{ae}$ | $R_{av}$ | | | | |
| C6-63 | 11 | $R_{aa}$ | $R_{aw}$ | C6-64 | 11 | $R_{ad}$ | $R_{aw}$ |
| C6-65 | 11 | $R_{ae}$ | $R_{aw}$ | | | | |

wherein each of compounds C1-1 to C1-96, C2-1 to C2-54, C2-56 to C2-58, C2-60 to C2-62, C2-64 to C2-66, C2-68 to C2-70, C2-72 to C2-74, C2-76 to C2-78, C2-80 to C2-82, C2-84 to C2-86, C3-1 to C3-66, C4-1 to C4-33, C4-35 to C4-37, C4-39 to C4-41, C4-43 to C4-45, C4-47 to C4-49, C4-51 to C4-53, C4-55 to C4-57, C4-59 to C4-61, C4-63 to C4-65, C5-1 to C5-66, C6-1 to C6-33, C6-35 to C6-37, C6-39 to C6-41, C6-43 to C6-45, C6-47 to C6-49, C6-51 to C6-53, C6-55 to C6-57, C6-59 to C6-61 and C6-63 to C6-65 is represented by any one of formulas 7 to 11, and R and $R_{12}$, each independently, are any one of the following $R_{aa}$ to $R_{aw}$, $R_{ay}$, $R_{az}$ and $R_{ba}$ to $R_{bi}$:

Raa

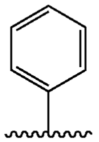

Rab

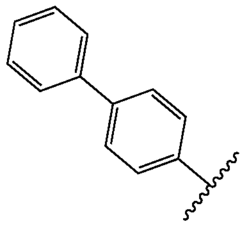

Rac

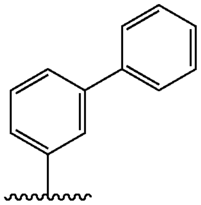

Rad

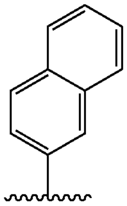

Rae

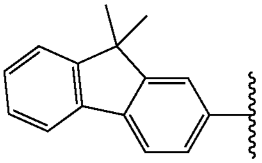

Raf

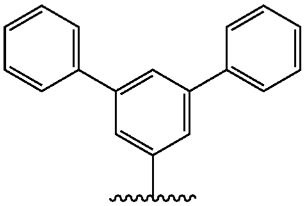

-continued
Rag
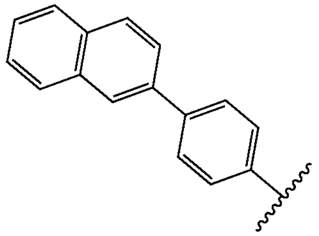
Rah
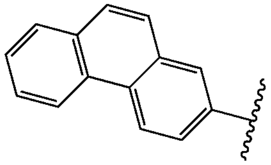
Rai
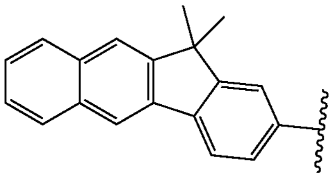
Raj
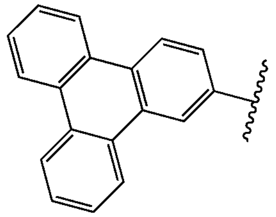
Rak
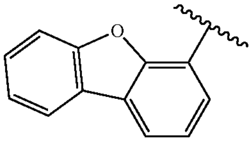
Ral
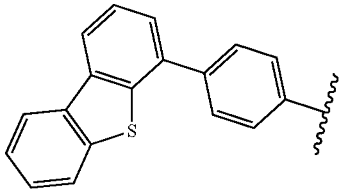
Ram
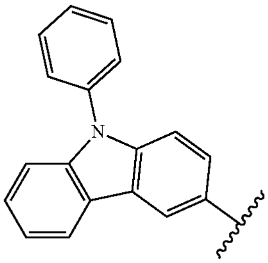
-continued
Ran
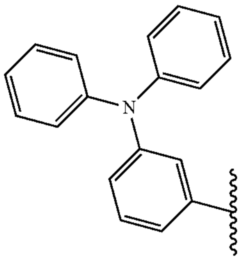
Rao
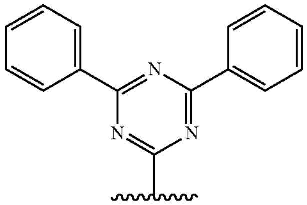
Rap
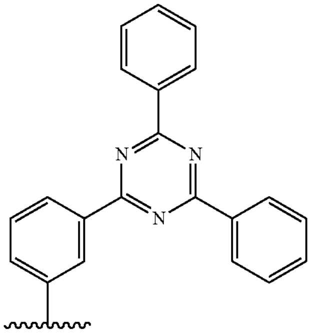
Raq
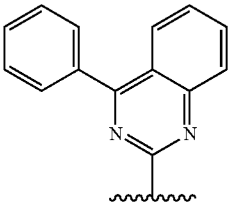
Rar
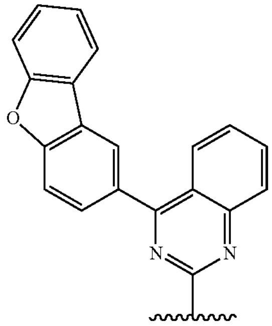
Ras
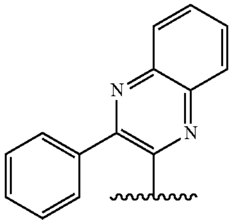

-continued
Rat
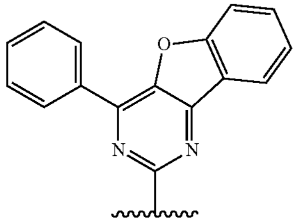
Rau
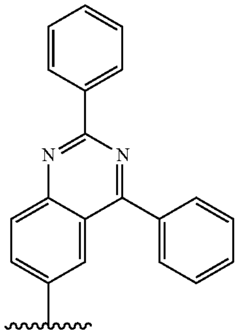
Rav
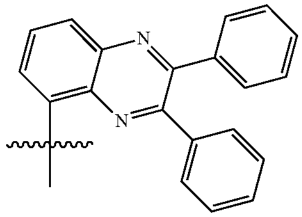
Raw
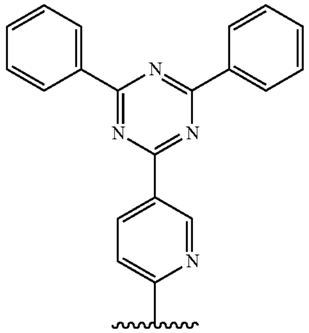
Ray
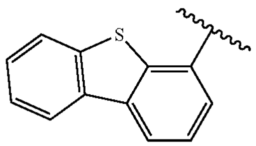
Raz
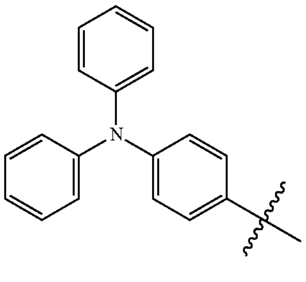
-continued
Rba
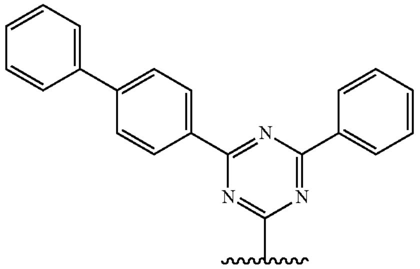
Rbb
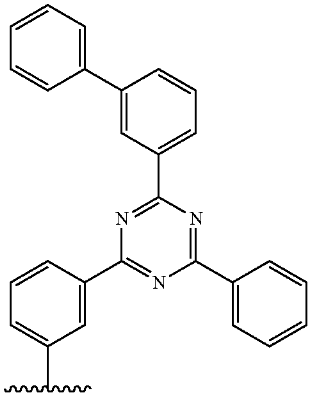
Rbc
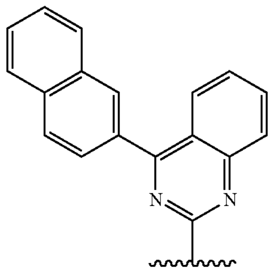
Rbd
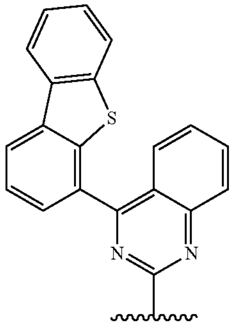
Rbe
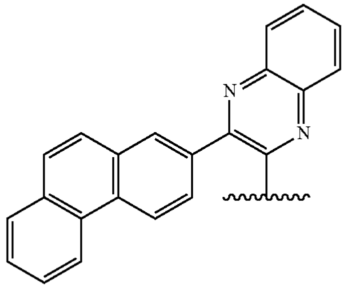

-continued
Rbf
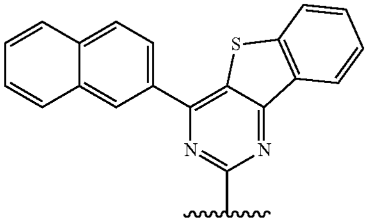
Rbg
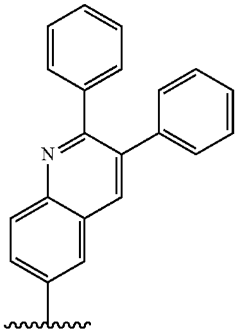
-continued
Rbh
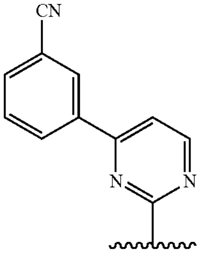
and
Rbi
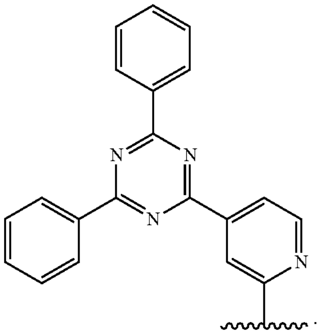
* * * * *